US008334292B1

(12) United States Patent
Chiang

(10) Patent No.: US 8,334,292 B1
(45) Date of Patent: Dec. 18, 2012

(54) PYRIMIDINE COMPOUNDS AND METHODS OF MAKING AND USING SAME

(75) Inventor: Phoebe Chiang, East Lyme, CT (US)

(73) Assignee: Cystic Fibrosis Foundation Therapeutics, Inc., Bethesda, MD (US)

( * ) Notice: Subject to any disclaimer, the term of this patent is extended or adjusted under 35 U.S.C. 154(b) by 0 days.

(21) Appl. No.: 13/159,689

(22) Filed: Jun. 14, 2011

Related U.S. Application Data

(60) Provisional application No. 61/354,348, filed on Jun. 14, 2010.

(51) Int. Cl.
A01N 43/54 (2006.01)
C07D 239/42 (2006.01)
C07D 401/04 (2006.01)

(52) U.S. Cl. ......... 514/256; 544/242; 544/315; 544/316

(58) Field of Classification Search .................. 514/256; 544/242, 315, 316
See application file for complete search history.

(56) References Cited

U.S. PATENT DOCUMENTS

| 2006/0079543 A1 | 4/2006 | Sum et al. |
| 2009/0221597 A1 | 9/2009 | Ruah et al. |
| 2011/0281873 A1 | 11/2011 | Chiang et al. |

FOREIGN PATENT DOCUMENTS

| EP | 0233461 A2 | 8/1987 |
| JP | 2005-145956 A | 6/2005 |
| WO | WO-01/00214 A1 | 1/2001 |
| WO | WO-02/083667 A2 | 10/2002 |
| WO | WO-02/102800 A1 | 12/2002 |
| WO | WO-03/000682 A1 | 1/2003 |
| WO | WO-03/056329 A2 | 7/2003 |
| WO | WO-2004/016597 A2 | 2/2004 |
| WO | WO-2004/089913 A1 | 10/2004 |
| WO | WO-2004/110452 A1 | 12/2004 |
| WO | WO-2004/111014 A1 | 12/2004 |
| WO | WO-2005/040135 A1 | 5/2005 |
| WO | WO-2005/075435 A1 | 8/2005 |
| WO | WO-2006/066172 A1 | 6/2006 |
| WO | WO-2006/127588 A2 | 11/2006 |
| WO | WO-2007/021982 A2 | 2/2007 |
| WO | WO-2007/056341 A1 | 5/2007 |
| WO | WO-2008/092199 A1 | 8/2008 |
| WO | WO-2008/098058 A1 | 8/2008 |
| WO | WO-2009/076593 A1 | 6/2009 |
| WO | WO-2010/068863 A2 | 6/2010 |
| WO | WO-2010/151747 A1 | 12/2010 |
| WO | WO-2011/008931 A2 | 1/2011 |

OTHER PUBLICATIONS

Paul et al. (1993) "Preparation of substituted N-phenyl-4-aryl-2-pyrimidinamines as mediator release inhibitors.," Journal of Medicinal Chemistry, vol. 36(19), pp. 2716-2725. (Abstract only).

Primary Examiner — Paul V. Ward
(74) Attorney, Agent, or Firm — Goodwin Procter LLP

(57) ABSTRACT

Disclosed herein are pyrimidinyl compounds that are contemplated to be modulators of cystic fibrosis transmembrane regulators (CFTR), and methods of making and using same. Also provided are pharmaceutical compositions and methods of treating disorders associated with cystic fibrosis transmembrane regulators, such as airway inflammation, cystic fibrosis, and the like.

20 Claims, No Drawings

PYRIMIDINE COMPOUNDS AND METHODS OF MAKING AND USING SAME

RELATED APPLICATIONS

This application claims the benefit of and priority to U.S. Provisional Patent Application Ser. No. 61/354,348, filed Jun. 14, 2010, the contents of which are hereby incorporated by reference for all purposes.

FIELD OF THE INVENTION

The invention relates to pyrimidine compounds, methods of modulating the activity of the cystic fibrosis transmembrane regulator, and therapeutic uses of the pyrimidine compounds. In particular, the present invention relates to aminopyrimidinyl and related compounds, methods of using such compounds to modulate the activity of the cystic fibrosis transmembrane regulator in a subject and to treat cystic fibrosis.

BACKGROUND

The cystic fibrosis transmembrane regulator (CFTR) is a protein of approximately 1480 amino acids made up of two repeated elements, each having six transmembrane segments and a nucleotide binding domain. Based on its predicted domain structure, CFTR is a member or a class of related proteins which includes the multi-drug resistance (MDR) or P-glycoprotein, bovine adenyl cyclase, the yeast STE6 protein, as well as several bacterial amino acid transport proteins. Proteins in this group, characteristically, are involved in pumping molecules into or out of cells. The CFTR has been postulated to regulate the outward flow of anions from epithelial cells in response to phosphorylation by cyclic AMP-dependent protein kinase or protein kinase C.

Cystic fibrosis (CF) is a lethal, hereditary, autosomal recessive disease which is caused by mutations in the gene coding for the CFTR Cl⁻-channel. By far the most common disease-causing mutation is the deletion of the codon for phenylalanine 508 (ΔF508) in the primary sequence of wild type CFTR. Over 90% of patients carry at least one allele of the ΔF508 CFTR mutant gene. The gene product from this mutant gene is a CFTR Cl⁻-channel that is poorly processed within the cell: most of the mutant protein is incorrectly or incompletely folded and becomes targeted for endoplasmic reticulum-associated degradation (ERAD). The few mutant Cl⁻-channels that pass the quality control or simply escape the ER before they are degraded will mature through the golgi and eventually be incorporated into the plasma membrane. These are thought to represent <5% of the level observed in cells expressing wild type CFTR, resulting in a commensurate low total whole-cell Cl⁻-conductance. In addition to the much lower number of channels in the plasma membrane, the open probability of the individual channel proteins is ~3-fold reduced compared to wild type CFTR.

For over a decade, efforts have been ongoing to identify small molecule drugs that can restore the cell CFTR Cl⁻-conductance to levels high enough to ameliorate the effects of CF. These include correctors of ΔF508 CFTR, compounds that can improve the intracellular processing, and potentiators, compounds which increase the open probability of mutant CFTR channels at the cell surface.

A small molecule, dual-acting potentiator-corrector is expected to be of great benefit for the treatment of most CF patients. To date, it has proven difficult to develop compounds acting solely by correction of the intracellular processing that can sufficiently increase the number of channels in the cell surface to overcome the disease-causing deficiency in Cl⁻-conductance. On the other hand, potentiation, i.e., increase of open probability, of only the mutant channels at the cell surface will not sufficiently restore Cl⁻-conductance for most CF patients. A dual-acting potentiator-corrector molecule would mechanistically combine aspects of both corrector and potentiator compounds: the number of CFTR channels at the surface and the channel open probability are increased in parallel.

SUMMARY

Provided herein are compounds contemplated to be CFTR modulators, and their use as, for example, medicinal agents. Also provided are pharmaceutical compositions comprising at least one disclosed compound, or a pharmaceutically acceptable salt, prodrug or N-oxide thereof, and a pharmaceutically acceptable carrier.

Accordingly, one aspect of the invention provides a compound of Formula I:

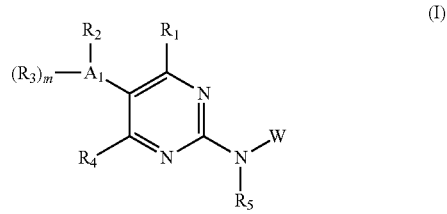

(I)

or a pharmaceutically acceptable salt or N-oxide thereof, wherein the variables are as defined in the detailed description.

Another aspect of the invention provides a compound of Formula II:

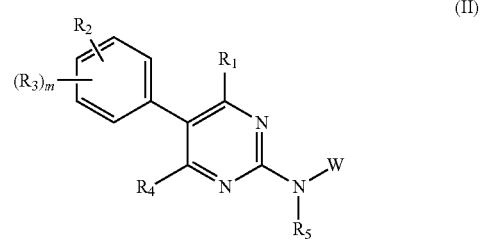

(II)

or a pharmaceutically acceptable salt or N-oxide thereof, wherein the variables are as defined in the detailed description.

Another aspect of the invention provides a compound of Formula III:

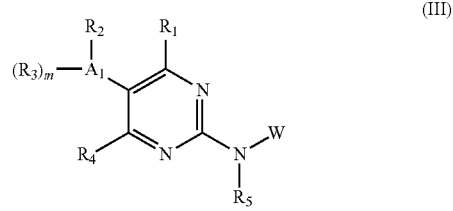

(III)

or a pharmaceutically acceptable salt or N-oxide thereof, wherein the variables are as defined in the detailed description.

Another aspect of the invention provides a compound of Formula IV:

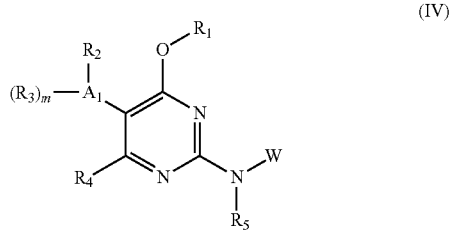

or a pharmaceutically acceptable salt or N-oxide thereof, wherein the variables are as defined in the detailed description.

Also provided herein are methods of treating airway inflammation, such as in cystic fibrosis, comprising administering to a subject in need thereof a therapeutically effective amount of a compound described herein, e.g., a compound of Formula I, IA, II, IIA, III, or IV. Also described herein are compositions that include a compound, e.g., a compound of I, IA, II, IIA, III, or IV, and a pharmaceutically acceptable excipient.

The invention further provides methods of modulating the activity of one or more cystic fibrosis transmembrane regulators comprising, for example, exposing said receptor to a compound described herein, e.g., a compound of Formula I, IA, II, IIA, III, or IV.

Also provided herein are methods of treating a disease associated with expression or activity of one or more cystic fibrosis transmembrane regulators in a subject comprising administering to the subject a therapeutically effective amount of a disclosed compound. For example, provided herein are methods of treating chronic obstructive pulmonary disease, dry eye disease, and Sjögren's syndrome, comprising administering a compound described herein, e.g., a compound of Formula I, IA, II, IIA, III, or IV. Also provided are use of a compound described herein for therapy and/or the manufacture of a medicament for the treatment of disease associated with cystic fibrosis transmembrane regulators.

DETAILED DESCRIPTION

The features and other details of the disclosure will now be more particularly described. Before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

I. DEFINITIONS

"Treating" includes any effect, e.g., lessening, reducing, modulating, or eliminating, that results in the improvement of the condition, disease, disorder and the like.

The term "aldehyde" or "formyl" as used herein refers to the radical —CHO.

The term "alkanoyl" as used herein refers to a radical —O—CO-alkyl.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$alkenyl, $C_2$-$C_{10}$alkenyl, and $C_2$-$C_6$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkoxy" as used herein refers to an alkyl group attached to an oxygen (—O-alkyl-). Exemplary alkoxy groups include, but are not limited to methoxy, ethoxy, etc.

The term "alkyl" as used herein refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkynyl" as used herein refers to an unsaturated straight or branched hydrocarbon having at least one carbon-carbon triple bond, such as a straight or branched group of 2-12, 2-8, or 2-6 carbon atoms, referred to herein as $C_2$-$C_{12}$alkynyl, $C_2$-$C_8$alkynyl, and $C_2$-$C_6$alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc.

The term "amide" or "amido" as used herein refers to a radical of the form —$R_aC(O)N(R_b)$—, —$R_aC(O)N(R_b)R_c$—, —$C(O)NR_bR_c$, or —$C(O)NH_2$, wherein $R_a$, $R_b$ and $R_c$ are each independently selected from alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, and nitro. The amide can be attached to another group through the carbon, the nitrogen, $R_b$, $R_c$, or $R_a$. The amide also may be cyclic, for example $R_b$ and $R_c$, $R_a$ and $R_b$, or $R_a$ and $R_c$ may be joined to form a 3- to 12-membered ring, such as a 3- to 10-membered ring or a 5- to 6-membered ring. The term "carboxamido" refers to the structure —$C(O)NR_bR_c$. In certain embodiments, the carboxamido group is represented by the radical —C(O)NRR', where R and R' may be the same or different and selected from, for example, alkyl, aryl, arylalkyl, cycloalkyl, formyl, haloalkyl, heteroaryl and heterocyclyl.

The term "amidino" as used herein refers to a radical of the form —C(=NR)NR'R" where R, R', and R" can each independently be selected from alkyl, alkenyl, alkynyl, amide, aryl, arylalkyl, cyano, cycloalkyl, haloalkyl, heteroaryl, heterocyclyl, hydroxyl, ketone and nitro.

The term "amine" or "amino" as used herein refers to a radical of the form —$NR_dR_e$, —$N(R_d)R_e$—, or —$R_eN(R_d)R_f$— where $R_d$, $R_e$, and $R_f$ are independently selected from alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, and nitro. The amino can be attached to the parent molecular group through the nitrogen, $R_d$, $R_e$ or $R_f$. The amino also may be cyclic, for example any two of $R_d$, $R_e$ or $R_f$ may be joined together or with the N to form a 3- to 12-membered ring, e.g., morpholino or piperidinyl. The term amino also includes the corresponding quaternary ammonium salt of any amino group, e.g., —[N(Rd)(Re)(Rf)]+. Exemplary amino groups include aminoalkyl groups, wherein at least one of $R_d$, $R_e$, or $R_f$ is an alkyl group.

The term "aryl" as used herein refers to refers to a mono-, bi-, or other multi-carbocyclic, aromatic ring system. Unless specified otherwise, the aromatic ring is optionally substituted at one or more ring positions with substituents independently selected from alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. In certain embodiments, the aryl group is not substituted, i.e., it is unsubstituted.

The term "arylalkyl" (also presented as "aralkyl") as used herein refers to an aryl group having at least one alkyl substituent, e.g. -aryl-alkyl-. Exemplary arylalkyl groups include, but are not limited to, arylalkyls having a monocyclic aromatic ring system, wherein the ring comprises 6 carbon atoms. For example, "phenylalkyl" includes phenyl$C_{1-4}$alkyl, benzyl, 1-phenylethyl, 2-phenylethyl, etc.

The term "azido" as used herein refers to the radical —$N_3$.

The term "carbamate" as used herein refers to a radical of the form —$R_g$OC(O)N($R_h$)—, —$R_g$OC(O)N($R_h$)$R_i$-, or —OC(O)N$R_h$$R_i$, wherein $R_g$, $R_h$ and $R_i$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, sulfide, sulfonyl, and sulfonamide. Exemplary carbamates include, but are not limited to, arylcarbamates or heteroaryl carbamates, e.g., wherein at least one of $R_g$, $R_h$ and $R_i$ are independently selected from aryl or heteroaryl, such as phenyl and pyridinyl.

The term "carbonyl" as used herein refers to the radical —C(O)—.

The term "carboxy" as used herein refers to the radical —COOH or its corresponding salts, e.g. —COONa, etc.

The term "cyano" as used herein refers to the radical —CN.

The term "cycloalkoxy" as used herein refers to a cycloalkyl group attached to an oxygen.

The term "cycloalkyl" as used herein refers to a monovalent saturated or unsaturated cyclic, bicyclic, or bridged cyclic (e.g., adamantyl)hydrocarbon group of 3-10, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclohexenes, cyclopentanes, cyclopentenes, cyclobutanes and cyclopropanes. Unless specified otherwise, cycloalkyl groups are optionally substituted with alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. Cycloalkyl groups can be fused to other cycloalkyl, aryl, or heterocyclyl groups. In certain embodiments, the cycloalkyl group is not substituted, i.e., it is unsubstituted.

The term "ether" refers to a radical having the structure —$R_l$O—$R_m$—, where $R_l$ and $R_m$ can independently be alkyl, aryl, cycloalkyl, heterocyclyl, or ether. The ether can be attached to the parent molecular group through $R_l$ or $R_m$. Exemplary ethers include, but are not limited to, alkoxyalkyl and alkoxyaryl groups. Ether also includes polyethers, e.g., where one or both of $R_l$ and $R_m$ are ethers.

The terms "halo" or "halogen" or "Hal" as used herein refer to F, Cl, Br, or I.

The term "haloalkyl" as used herein refers to an alkyl group substituted with one or more halogen atoms.

The terms "heteroaryl" as used herein refers to a 5-15 membered mono-, bi-, or other multi-cyclic, aromatic ring system containing one or more heteroatoms, for example one to four heteroatoms, such as nitrogen, oxygen, and sulfur. Heteroaryls can also be fused to non-aromatic rings. Unless specified otherwise, the heteroaryl ring is optionally substituted at one or more positions with such substituents as described above, as for example, alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. Illustrative examples of heteroaryl groups include, but are not limited to, acridinyl, benzimidazolyl, benzofuryl, benzothiazolyl, benzothienyl, benzoxazolyl, carbazolyl, carbolinyl, cinnolinyl, furazanyl, furyl, imidazolyl, indazolyl, indolizinyl, indolyl, isobenzofuryl, isoindolyl, isoquinolinyl, isothiazolyl, isoxazolyl, naphthyridinyl, oxadiazolyl, oxazolyl, phenanthridinyl, phenanthrolinyl, phenarsazinyl, phenazinyl, phenothiazinyl, phenoxazinyl, phthalazinyl, pteridinyl, purinyl, pyrazinyl, pyrazolyl, pyrazyl, pyridazinyl, pyridinyl, pyrimidilyl, pyrimidyl, pyrrolyl, quinolinyl, quinolizinyl, quinoxalinyl, quinoxaloyl, quinazolinyl, tetrazolyl, thiadiazolyl, thianthrenyl, thiazolyl, thienyl, thiophenyl, triazinyl, (1,2,3,)- and (1,2,4)-triazolyl, and the like. Exemplary heteroaryl groups include, but are not limited to, a monocyclic aromatic ring, wherein the ring comprises 2 to 5 carbon atoms and 1 to 3 heteroatoms. In certain embodiments, the heteroaryl group is not substituted, i.e., it is unsubstituted.

The terms "heterocyclyl" or "heterocyclic group" are art-recognized and refer to saturated or partially unsaturated 3- to 10-membered ring structures, alternatively 3- to 7-membered rings, whose ring structures include one to four heteroatoms, such as nitrogen, oxygen, and sulfur. Heterocycles may also be mono-, bi-, or other multi-cyclic ring systems. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isoxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. Unless specified otherwise, the heterocyclic ring is optionally substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. In certain embodiments, the heterocyclcyl group is not substituted, i.e., it is unsubstituted.

The term "heterocycloalkyl" is art-recognized and refers to a saturated heterocyclyl group as defined above.

The term "heterocyclylalkoxy" as used herein refers to a heterocyclyl attached to an alkoxy group.

The term "heterocyclyloxyalkyl" refers to a heterocyclyl attached to an oxygen (—O—), which is attached to an alkyl group.

The terms "hydroxy" and "hydroxyl" as used herein refers to the radical —OH.

The term "hydroxyalkyl" as used herein refers to a hydroxy radical attached to an alkyl group.

The term "imino" as used herein refers to the radical —C(=N)—R", where R" can be, for example, alkyl, alkenyl, alkynyl, aryl, arylalkyl, cycloalkyl, ether, haloalkyl, heteroaryl, heterocyclyl, and ketone.

The term "nitro" as used herein refers to the radical —$NO_2$.

The term "phenylene" as used herein refers a multi-radical of benzene, e.g.,

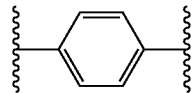

or

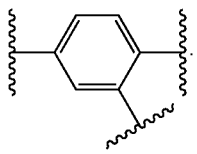

The term "heteroarylene" is art-recognized and refers to a multi-radical of a heteroaryl group.

The term "phosphate" as used herein refers to the radical —OP(O)(OR$_{aa}$)$_2$ or its anions. The term "phosphanato" refers to the radical —P(O)(OR$_{aa}$)$_2$ or its anions. The term "phosphinato" refers to the radical —PR$_{aa}$(O)(OR$_{aa}$) or its anion, where each R$_{aa}$ can be selected from, for example, alkyl, alkenyl, alkynyl, aryl, arylalkyl, cycloalkyl, hydrogen, haloalkyl, heteroaryl, and heterocyclyl.

The term "sulfate" as used herein refers to the radical —OS(O)(OR$_{aa}$)$_2$ or its anions, where R$_{aa}$ is defined above.

The term "sulfonamide" or "sulfonamido" as used herein refers to a radical having the structure —N(R$_r$)—S(O)$_2$—R$_s$— or —S(O)$_2$—N(R$_r$)R$_s$, where R$_r$ and R$_s$ can be, for example, hydrogen, alkyl, aryl, cycloalkyl, and heterocyclyl. Exemplary sulfonamides include alkylsulfonamides (e.g., where R$_s$ is alkyl), arylsulfonamides (e.g., where R$_s$ is aryl), cycloalkyl sulfonamides (e.g., where R$_s$ is cycloalkyl), and heterocyclyl sulfonamides (e.g., where R$_s$ is heterocyclyl), etc.

The term "sulfonyl" as used herein refers to a radical having the structure R$_u$SO$_2$—, where R$_u$ can be alkyl, aryl, cycloalkyl, and heterocyclyl, e.g., alkylsulfonyl. The term "alkylsulfonyl" as used herein refers to an alkyl group attached to a sulfonyl group.

The term "sulfide" as used herein refers to the radical having the structure R$_z$S—, where R$_z$ can be alkoxy, alkyl, alkynyl, amide, amino, aryl, arylalkyl, carbamate, carboxy, cycloalkyl, ester, ether, formyl, haloalkyl, heteroaryl, heterocyclyl, and ketone. The term "alkylsulfide" as used herein refers to an alkyl group attached to a sulfur atom. Exemplary sulfides include "thio," which as used herein refers to an —SH radical.

The term "thiocarbonyl" or "thiocarboxy" as used herein refers to compounds and moieties which contain a carbon connected with a double bond to a sulfur atom.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the invention can be administered to a mammal, such as a human, but can also be other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in whom modulation of cystic fibrosis transmembrane regulators is desired.

"Modulation" includes antagonism (e.g., inhibition), agonism, partial antagonism and/or partial agonism. Modulators may be dual acting corrector/potentiator compounds. In one embodiment, a modulator is a corrector compound. In another embodiment, a modulator is a potentiator compound.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in the prevention of or a decrease in the symptoms associated with a disease associated with cystic fibrosis transmembrane regulators.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well known asymmetric synthetic methods.

Geometric isomers can also exist in the compounds of the present invention. The symbol ========== denotes a bond that may be a single, double or triple bond as described herein. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a polymorph. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in, e.g., the Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms, such as through hydrolysis in blood. For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, if a compound of the invention contains an alcohol functional group, a prodrug can be formed by the replacement of the hydrogen atom of the alcohol group with a group such as $(C_1-C_6)$alkanoyloxymethyl, 1-$((C_1-C_6)$alkanoyloxy)ethyl, 1-methyl-1-$((C_1-C_6)$alkanoyloxy)ethyl $(C_1-C_6)$ alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O$(C_1-C_6)$alkyl)$_2$ or glycosyl (the radical resulting from the removal of a hydroxyl group of the hemiacetal form of a carbohydrate).

If a compound of the invention incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl-natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy$(C_1-C_6)$alkyl, amino$(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino, morpholino, piperidin-1-yl or pyrrolidin-1-yl.

II. PYRIMIDINYL COMPOUNDS & PHARMACEUTICAL COMPOSITIONS

One aspect of the invention provides a compound of Formula I:

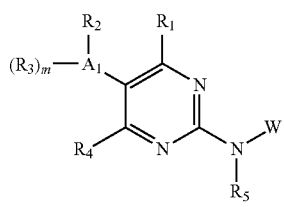

(I)

or a pharmaceutically acceptable salt or N-oxide thereof, wherein:

$R_1$ is —O—$(CR_6R_7)_n$-$A_2$, —N($R_6$)$(CR_6R_7)_n$-$A_2$, —S—$(CR_6R_7)_n$-$A_2$, or heterocycloalkyl, wherein said heterocycloalkyl is optionally substituted with one or more substituents independently selected from the group consisting of halogen, $C_1$-$C_6$alkyl, $C_3$-$C_6$cycloalkyl, $C_2$-$C_4$alkenyl, $C_2$-$C_4$alkynyl, $C_1$-$C_6$alkoxyl, hydroxyl, —CF$_3$, —CH$_2$F, —CHF$_2$, —N($R_8$)$R_9$, —CN, —C(O)$R_{10}$, —CO$_2$$R_8$, —OC(O)$R_9$, —CON($R_8$)$R_9$, —N($R_8$)COR$_{10}$, —N($R_8$)SO$_2$R$_{10}$, —SO$_2$N($R_8$)$R_9$, —N($R_8$)SO$_2$N($R_8$)$R_9$, and —SO$_2$R$_{10}$;

$R_2$ is —O-heterocycloalkyl, —O-heterocycloalkenyl, —Y-heterocycloalkyl, —Y-heterocycloalkenyl, heterocycloalkyl, -heterocycloalkenyl, -cycloalkyl, -cycloalkenyl, —$(CR_6R_7)_n$—$C_1$-$C_6$alkoxyl, —O—$(CR_6R_7)_n$—$C_1$-$C_6$alkoxyl, $C_1$-$C_6$alkoxyl, halogen, —CF$_3$, —CH$_2$F, —CHF$_2$, —OCF$_3$, —OCH$_2$F, hydroxyl, or $C_1$-$C_6$alkyl, wherein said heterocycloalkyl, heterocycloalkyl, cycloalkyl, and cycloalkenyl are optionally substituted with one or more substituents independently selected from the group consisting of halogen, $C_1$-$C_6$alkyl, $C_3$-$C_6$cycloalkyl, $C_2$-$C_4$alkenyl, $C_2$-$C_4$alkynyl, $C_1$-$C_6$alkoxyl, hydroxyl, —CF$_3$, —CH$_2$F, —CHF$_2$, —OCF$_3$, —N($R_8$)$R_9$, —CN, —C(O)$R_{10}$, —CO$_2$$R_8$, —OC(O)$R_9$, —CON($R_8$)$R_9$, —N($R_8$)COR$_{10}$, —N($R_8$)SO$_2$R$_{10}$, —SO$_2$N($R_8$)$R_9$, —N($R_8$)SO$_2$N($R_8$)$R_9$, and —SO$_2$R$_{10}$;

$R_3$ is hydrogen, halogen, $C_1$-$C_6$alkyl, $C_3$-$C_6$cycloalkyl, $C_2$-$C_4$alkenyl, $C_2$-$C_4$alkynyl, $C_1$-$C_6$alkoxyl, hydroxyl, —CF$_3$, —CH$_2$F, —CHF$_2$, —OCF$_3$, —OCH$_2$F, —N($R_8$)$R_9$, —CN, —C(O)$R_{10}$, —CO$_2$$R_8$, —CON($R_8$)$R_9$, —N($R_8$)COR$_{10}$, —N($R_8$)SO$_2$R$_{10}$, —SO$_2$N($R_8$)$R_9$, or —SO$_2$R$_{10}$;

$R_4$ is hydrogen, halogen, $C_1$-$C_4$alkyl, cyclopropyl, —CN, or —CF$_3$ $R_5$ is hydrogen or $C_1$-$C_4$alkyl;

$R_6$ and $R_7$ each represent independently for each occurrence hydrogen or alkyl, or when $R_6$ and $R_7$ are attached to the same atom, $R_6$ and $R_7$ are optionally taken together with the atom to which they are attached to form a 3-6 membered cycloalkyl or heterocycloalkyl group;

$R_8$ and $R_9$ each represent independently for each occurrence hydrogen, alkyl, cycloalkyl, heterocycloalkyl, aryl, heteroaryl, aralkyl, or heteroaralkyl; or when $R_8$ and $R_9$ are attached to the same atom, $R_8$ and $R_9$ are optionally taken together with the atom to which they are attached to form a 3-6 membered cycloalkyl or heterocycloalkyl group;

$R_{10}$ represents independently for each occurrence alkyl, cycloalkyl, heterocycloalkyl, aryl, heteroaryl, aralkyl, or heteroaralkyl;

$A_1$ is phenylene or a monocyclic heteroarylene group;

$A_2$ is a heterocycloalkyl group containing at least one nitrogen or sulfur atom, and wherein said heterocycloalkyl group is optionally substituted with one or more substituents independently selected from the group consisting of halogen, $C_1$-$C_6$alkyl, $C_2$-$C_4$alkenyl, $C_2$-$C_4$alkynyl, $C_1$-$C_6$alkoxyl, $C_3$-$C_6$cycloalkyl, hydroxyl, —CF$_3$, —CH$_2$F, —CHF$_2$, —N($R_8$)$R_9$, —CN, —C(O)$R_{10}$, —CO$_2$$R_8$, —OC(O)$R_9$, —CON($R_8$)$R_9$, —N($R_8$)COR$_{10}$, —N($R_8$)SO$_2$R$_{10}$, —SO$_2$N($R_8$)$R_9$, —N($R_8$)SO$_2$N($R_8$)$R_9$, and —SO$_2$R$_{10}$;

W is $C_1$-$C_6$alkyl or $C_4$-$C_{10}$cycloalkyl, each of which are optionally substituted with one, two, or three substituents independently selected from the group consisting of $C_1$-$C_6$alkyl, $C_1$-$C_6$haloalkyl, cycloalkyl, —OC$_1$-$C_6$alkyl, —O-cycloalkyl, —OH, —CF$_3$, and fluoro;

Y is —N($R_8$)—, —S—, —S(O)—, or —S(O)$_2$—;

m is 1 or 2; and n is 0, 1, 2, 3, or 4.

In certain embodiments, $R_1$ is —O—$(CR_6R_7)_n$-$A_2$ or a heterocycloalkyl group optionally substituted with one or more substituents independently selected from the group consisting of halogen, $C_1$-$C_6$alkyl, $C_3$-$C_6$cycloalkyl, —C(O)$R_{10}$, —CO$_2$$R_8$, —OC(O)$R_9$, —CON($R_8$)$R_9$, —N($R_8$)COR$_{10}$, —N($R_8$)SO$_2$R$_{10}$, —SO$_2$N($R_8$)$R_9$, —N($R_8$)SO$_2$N($R_8$)$R_9$, and —SO$_2$R$_{10}$. In certain embodiments, $R_1$ is —O—$(CR_6R_7)_n$-$A_2$.

In certain embodiments, $A_2$ is a heterocycloalkyl group containing at least one nitrogen or sulfur atom, and wherein said heterocycloalkyl group is optionally substituted with one or more substituents independently selected from the group consisting of halogen, $C_1$-$C_6$alkyl, $C_3$-$C_6$cycloalkyl, —C(O)$R_{10}$, —CO$_2$$R_8$, —OC(O)$R_9$, —CON($R_8$)$R_9$, —N($R_8$)COR$_{10}$, —N($R_8$)SO$_2$R$_{10}$, —SO$_2$N($R_8$)$R_9$, —N($R_8$)SO$_2$N($R_8$)$R_9$, and —SO$_2$R$_{10}$. In certain embodiments, $A_2$ is a heterocycloalkyl group containing at least one nitrogen or sulfur atom, and wherein said heterocycloalkyl group is substituted with one or more substituents independently selected from the group consisting of —CON($R_8$)$R_9$, —SO$_2$N($R_8$)$R_9$, and —SO$_2$R$_{10}$. In certain embodiments, $A_2$ is a 3-6 membered heterocycloalkyl group containing at least one nitrogen, and wherein said heterocycloalkyl group is substituted with —SO$_2$R$_{10}$. In certain embodiments, $A_2$ is an azetidinyl, pyrrolidinyl, piperidinyl or morpholinyl, each of which is substituted with —CON($R_8$)$R_9$, —SO$_2$N($R_8$)$R_9$, or —SO$_2$R$_{10}$. In certain embodiments, A$_2$ is azetidinyl substituted with —CON($R_8$)$R_9$, —SO$_2$N($R_8$)$R_9$, or —SO$_2$R$_{10}$.

In certain other embodiments, A$_2$ is a heterocycloalkyl group containing at least one nitrogen or sulfur atom, and wherein said heterocycloalkyl group is substituted with one or more substituents independently selected from the group consisting of —CO$_2$R$_8$, —CON($R_8$)$R_9$, —SO$_2$N($R_8$)$R_9$, and —SO$_2$R$_{10}$. In certain embodiments, A$_2$ is a 3-6 membered heterocycloalkyl group containing at least one nitrogen, and wherein said heterocycloalkyl group is substituted with —CO$_2$R$_8$, —SO$_2$N($R_8$)$R_9$, —SO$_2$R$_{10}$. In certain embodiments, A$_2$ is an azetidinyl, pyrrolidinyl, piperidinyl or morpholinyl, each of which is substituted with —CON($R_8$)$R_9$, —CO$_2$R$_8$, —SO$_2$N($R_8$)$R_9$, or —SO$_2$R$_{10}$. In certain embodiments, A$_2$ is azetidinyl, pyrrolidinyl, or piperidinyl, each substituted with —CON($R_8$)$R_9$, —CO$_2$R$_8$, —SO$_2$N($R_8$)$R_9$, or —SO$_2$R$_{10}$.

In certain embodiments, A$_2$ is one of the following:

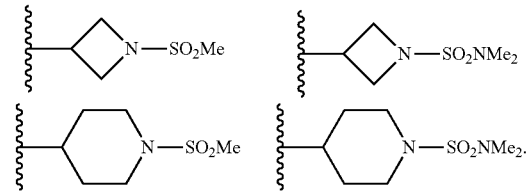

In certain other embodiments, A$_2$ is

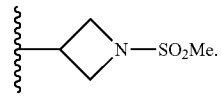

In certain embodiments, n is 0 or 1. In certain other embodiments, n is 0. In certain other embodiments, n is 1. In certain embodiments, m is 1.

In certain embodiments, R$_1$ is a heterocycloalkyl group containing at least one nitrogen or sulfur atom, and wherein said heterocycloalkyl group is optionally substituted with one or more substituents independently selected from the group consisting of halogen, C$_1$-C$_6$alkyl, —C(O)R$_{10}$, —CO$_2$R$_8$, —OC(O)R$_9$, —CON($R_8$)$R_9$, —N($R_8$)COR$_{10}$, —N($R_8$)SO$_2$R$_{10}$, —SO$_2$N($R_8$)$R_9$, —N($R_8$)SO$_2$N($R_8$)$R_9$, and —SO$_2$R$_{10}$. In certain embodiments, R$_1$ is a heterocycloalkyl group optionally substituted with one or more substituents independently selected from the group consisting of halogen, C$_1$-C$_6$alkyl, —CO$_2$R$_8$, —CON($R_8$)$R_9$, —SO$_2$N($R_8$)$R_9$, and —SO$_2$R$_{10}$. In certain embodiments, R$_1$ is a heterocycloalkyl group containing at least one nitrogen or sulfur atom, and wherein said heterocycloalkyl group is optionally substituted with one or more substituents independently selected from the group consisting of halogen and C$_1$-C$_6$alkyl. In certain embodiments, R$_1$ is morpholino, azetidinyl, piperidinyl, or pyrrolidinyl.

In certain embodiments, R$_2$ is —O-heterocycloalkyl or —O—(CR$_6$R$_7$)$_n$—C$_1$-C$_6$alkoxyl; wherein said heterocycloalkyl is optionally substituted with one or more substituents independently selected from the group consisting of halogen, C$_1$-C$_6$alkyl, C$_1$-C$_6$alkoxyl, hydroxyl, —N($R_8$)$R_9$, —C(O)R$_{10}$, —CO$_2$R$_8$, —OC(O)R$_9$, —CON($R_8$)$R_9$, —N($R_8$)COR$_{10}$, —N($R_8$)SO$_2$R$_{10}$, —SO$_2$N($R_8$)$R_9$, —N($R_8$)SO$_2$N($R_8$)$R_9$, and —SO$_2$R$_{10}$. In certain embodiments, R$_2$ is —O-heterocycloalkyl or —O—(CR$_6$R$_7$)$_n$—C$_1$-C$_6$alkoxyl; wherein said heterocycloalkyl is optionally substituted with one or more substituents independently selected from the group consisting of halogen, C$_1$-C$_6$alkyl, —CO$_2$R$_8$, and —CON($R_8$)$R_9$. In certain embodiments, R$_2$ is —O-heterocycloalkyl; wherein said heterocycloalkyl is optionally substituted with one or more substituents independently selected from the group consisting of halogen and C$_1$-C$_6$alkyl. In certain embodiments, R$_2$ is morpholinyl, —O-tetrahydrofuranyl, O-tetrahydropyranyl, —O-pyrrolidinyl, or —O-piperidinyl. In certain embodiments, R$_2$ is —O-tetrahydrofuranyl.

In certain other embodiments, R$_2$ is —O-heterocycloalkyl or —O—(CR$_6$R$_7$)$_n$—C$_1$-C$_6$alkoxyl; wherein said heterocycloalkyl is optionally substituted with one or more substituents independently selected from the group consisting of halogen, C$_1$-C$_6$alkyl, —CO$_2$R$_8$, —CON($R_8$)$R_9$, —SO$_2$N($R_8$)$R_9$, and —SO$_2$R$_{10}$. In certain other embodiments, R$_2$ is —O-heterocycloalkyl; wherein said heterocycloalkyl is optionally substituted with one or more substituents independently selected from the group consisting of —CO$_2$R$_8$, —CON($R_8$)$R_9$, —SO$_2$N($R_8$)$R_9$, and —SO$_2$R$_{10}$. In certain other embodiments, R$_2$ is morpholinyl, —O-tetrahydrofuranyl, O-tetrahydropyranyl, —O-pyrrolidinyl, O-azetidinyl or —O-piperidinyl; wherein said pyrrolidinyl, azetidinyl or piperidinyl each independently is optionally substituted with one or more substituents independently selected from the group consisting of, —CO$_2$R$_8$, —CON($R_8$)$R_9$, —SO$_2$N($R_8$)$R_9$, and —SO$_2$R$_1$ In certain embodiments, R$_3$ is hydrogen, halogen, —OCF$_3$, —OCH$_2$F, —CF$_3$, C$_1$-C$_6$alkyl, or C$_1$-C$_6$alkoxy. In certain embodiments, R$_3$ is hydrogen, halogen, C$_1$-C$_6$alkyl, C$_1$-C$_6$alkoxyl, hydroxyl, —NR$_8$R$_9$, —CN, or —C(O)R$_{10}$. In certain embodiments, R$_3$ is hydrogen, halogen, C$_1$-C$_6$alkyl, or C$_1$-C$_6$alkoxyl. In certain embodiments, R$_3$ is hydrogen, and m is 1.

In certain embodiments, R$_4$ is hydrogen or methyl, and R$_5$ is hydrogen. In certain embodiments, R$_4$ and R$_5$ are hydrogen. In certain embodiments, R$_4$ is methyl, and R$_5$ is hydrogen. In certain embodiments, R$_6$ and R$_7$ each represent independently for each occurrence hydrogen or methyl.

In certain embodiments, R$_8$ and R$_9$ each represent independently for each occurrence hydrogen, methyl, ethyl, n-propyl, isopropyl, butyl, cyclopropyl, cyclobutyl, phenyl, or benzyl, or R$_8$ and R$_9$ are optionally taken together with the atom to which they are attached to form a 3-6 membered cycloalkyl or heterocycloalkyl group. In certain embodiments, R$_8$ and R$_9$ each represent independently for each occurrence hydrogen, methyl, ethyl or cyclopropyl. In certain embodiments, R$_8$ and R$_9$ each represent independently for each occurrence hydrogen, methyl, ethyl, propyl, butyl, cyclopropyl, cyclobutyl, phenyl, or benzyl. In certain embodiments, R$_8$ and R$_9$ each represent independently for each occurrence hydrogen or methyl. In certain embodiments, R$_{10}$ is methyl, ethyl, n-propyl, isopropyl, butyl, cyclopropyl, cyclobutyl, phenyl, or benzyl.

In certain embodiments, A$_1$ is phenylene. In certain embodiments, A$_1$ is a pyridinyl diradical.

In certain embodiments, W is C$_5$-C$_{10}$cycloalkyl optionally substituted with one or two substituents independently selected from the group consisting of C$_1$-C$_6$alkyl and fluoro. In certain embodiments, W is C$_5$-C$_{10}$cycloalkyl optionally substituted with one or two substituents independently selected from the group consisting of C$_1$-C$_6$alkyl, —CF$_3$, and fluoro. In certain embodiments, W is cyclohexyl substituted with one or two substituents independently selected from the group consisting of $C_1$-$C_6$alkyl, —$CF_3$, and fluoro. In certain embodiments, W is selected from the group consisting of cyclobutyl, cycloheptyl, cyclohexyl, 4-methylcyclohexyl, 4-ethylcyclohexyl, 4-trifluoromethylcyclohexyl, 1-methylcyclohexyl, 1,5-dimethylcyclohexyl, cyclopentyl, isopropyl, and bicyclo[2,2,1]heptyl. In certain embodiments, W is selected from the group consisting of cyclobutyl, cyclohexyl, cycloheptyl, 4-methylcyclohexyl, 4-ethylcyclohexyl, 4-trifluoromethylcyclohexyl, cyclopentyl, and —$CH_2$cyclohexyl. In certain embodiments, W is cyclohexyl substituted with one or two $C_1$-$C_6$alkyl. In certain embodiments, W is cyclohexyl substituted with one or two substituents independently selected from the group consisting of methyl, ethyl, n-propyl, isopropyl, n-butyl, sec-butyl, isobutyl, and tert-butyl.

In certain embodiments, the compound is selected from the group consisting of: N,N-dimethyl-3-(2-((1s,4S)-4-methylcyclohexylamino)-5-(4-morpholinophenyl)pyrimidin-4-yloxy)azetidine-1-sulfonamide; N-(cis-4-methylcyclohexyl)-4-(1-(methylsulfonyl)azetidin-3-yloxy)-5-(4-((R)-tetrahydrofuran-3-yloxy)phenyl)pyrimidin-2-amine; N-(cis-4-methylcyclohexyl)-4-(1-(methylsulfonyl)azetidin-3-yloxy)-5-(4-(S)-tetrahydrofuran-3-yloxy)phenyl)pyrimidin-2-amine; methyl 4-(2-((1s,4s)-4-methylcyclohexylamino)-5-(4-morpholinophenyl)pyrimidin-4-yloxy)piperidine-1-carboxylate; N-((1s,4s)-4-methylcyclohexyl)-4-(1-(methylsulfonyl)piperidin-4-yloxy)-5-(4-((S)-tetrahydrofuran-3-yloxy)phenyl)pyrimidin-2-amine; N,N-dimethyl-3-(2-((1s,4s)-4-methylcyclohexylamino)-5-(4-((R)-tetrahydrofuran-3-yloxy)phenyl)pyrimidin-4-yloxy)azetidine-1-sulfonamide; N,N-dimethyl-3-(2-((1s,4S)-4-methylcyclohexylamino)-5-(4-((S)-tetrahydrofuran-3-yloxy)phenyl)pyrimidin-4-yloxy)azetidine-1-sulfonamide; and 4-(1-(cyclopropylsulfonyl)azetidin-3-yloxy)-N-((1s,4s)-4-methylcyclohexyl)-5-(4-((S)-tetrahydrofuran-3-yloxy)phenyl)pyrimidin-2-amine; or a pharmaceutically acceptable salt or N-oxide thereof.

Another aspect of the invention provides a compound of Formula IA:

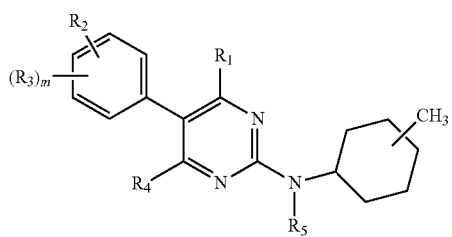

(IA)

or a pharmaceutically acceptable salt or N-oxide thereof, wherein:

$R_1$ is —O—$(CR_6R_7)_n$-$A_2$, or a heterocycloalkyl group containing at least one nitrogen or sulfur atom, and wherein said heterocycloalkyl group is optionally substituted with one or more substituents independently selected from the group consisting of halogen, $C_1$-$C_6$alkyl, $C_1$-$C_6$alkoxyl, —$CO_2R_8$, —$CON(R_8)R_9$, —$N(R_8)COR_{10}$, —$N(R_8)SO_2R_{10}$, —$SO_2N(R_8)R_9$, and —$SO_2R_{10}$;

$R_2$ is —O-heterocycloalkyl, heterocycloalkyl, or —O—$(CR_6R_7)_n$—$C_1$-$C_6$alkoxyl; wherein said heterocycloalkyl is optionally substituted with one or more substituents independently selected from the group consisting of halogen, $C_1$-$C_6$alkyl, $C_1$-$C_6$alkoxyl, —$C(O)R_{10}$, —$CO_2R_8$, —$CON(R_8)R_9$, —$N(R_8)COR_{10}$, and —$N(R_8)SO_2R_{10}$;

$R_3$ is hydrogen, halogen, or methyl;

$R_4$, $R_5$, $R_6$, $R_7$, $R_8$, and $R_9$ each represent independently for each occurrence hydrogen or methyl;

$R_{10}$ represents independently for each occurrence alkyl, cycloalkyl, or heterocycloalkyl;

$A_2$ is a heterocycloalkyl group containing at least one nitrogen or sulfur atom, and wherein said heterocycloalkyl group is optionally substituted with one or more substituents independently selected from the group consisting of $C_1$-$C_6$alkyl, $C_1$-$C_6$alkoxyl, —$C(O)R_{10}$, —$CO_2R_8$, —$OC(O)R_9$, —$CON(R_8)R_9$, —$N(R_8)COR_{10}$, —$N(R_8)SO_2R_{10}$, —$SO_2N(R_8)R_9$, and —$SO_2R_{10}$;

m is 1 or 2; and n is 0, 1, 2, 3, or 4.

In certain embodiments, the definition of the variables for Formula IA correspond to one or more of the embodiments described above for the definitions of the variables associated with Formula I to the extent the definition does not expand the scope of compounds embraced by Formula IA beyond that defined originally.

Another aspect of the invention provides a compound of Formula II:

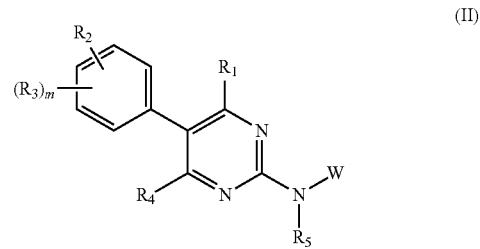

(II)

or a pharmaceutically acceptable salt or N-oxide thereof, wherein:

$R_1$ is a —O—$(CR_6R_7)_n$-heterocycloalkyl group, wherein the heterocycloalkyl group is a 5-7 membered ring containing 1 or 2 ring oxygen or sulfur atoms and the ring is optionally substituted with one or more substituents independently selected from the group consisting of halogen, $C_1$-$C_6$alkyl, $C_2$-$C_4$alkenyl, $C_2$-$C_4$alkynyl, $C_1$-$C_6$alkoxyl, hydroxyl, —$N(R_8)R_9$, —CN, —$C(O)R_{10}$, —$CO_2R_8$, —$OC(O)R_9$, —$CON(R_8)R_9$, —$N(R_8)COR_{10}$, —$N(R_8)SO_2R_{10}$, —$SO_2N(R_8)R_9$, —$N(R_8)SO_2N(R_8)R_9$, and —$SO_2R_{10}$;

$R_2$ is —O—$(CR_6R_7)_n$-heterocycloalkyl, heterocycloalkyl, a 5-6 membered heteroaryl, —O—$(CR_6R_7)_n$—$C_1$-$C_6$alkoxyl, —$(CR_6R_7)_n$-heterocycloalkyl, —C(O)-heterocycloalkyl, —$CON(R_8)R_9$, —$(CR_6R_7)_n$—$N(R_8)R_9$, —$(CR_6R_7)_n$—$N(R_8)COR_{10}$, —$CO_2R_8$, —$N(R_8)CO_2R_{10}$, —$C(O)N(R_8)S(O)_2N(R_8)R_9$, —C(O)N—CN, or —$SO_2N(R_8)C(O)R_{10}$; wherein the heterocycloalkyl groups are optionally substituted with one or more substituents independently selected from the group consisting of halogen, $C_1$-$C_6$alkyl, $C_2$-$C_4$alkenyl, $C_2$-$C_4$alkynyl, $C_1$-$C_6$alkoxyl, hydroxyl, —$N(R_8)R_9$, —CN, —$C(O)R_{10}$, —$CO_2R_8$, —OC(O)$R_9$, —$CON(R_8)R_9$, —$N(R_8)COR_{10}$, —$N(R_8)SO_2R_{10}$, —$SO_2N(R_8)R_9$, —$N(R_8)SO_2N(R_8)R_9$, and —$SO_2R_{10}$; provided that $R_2$ is not morpholinyl;

$R_3$ is hydrogen, halogen, —$CF_3$, —$CH_2F$, —$CHF_2$, —$OCH_2F$, $C_1$-$C_6$alkyl, $C_2$-$C_4$alkenyl, $C_2$-$C_4$alkynyl, methoxy, ethoxy, hydroxyl, —$N(R_8)R_9$, —CN, —$C(O)R_{10}$, —$CO_2R_8$, —$CON(R_8)R_9$, —$N(R_8)COR_{10}$, —$N(R_8)SO_2R_{10}$, —$SO_2N(R_8)R_9$, or —$SO_2R_{10}$;

$R_4$ and $R_5$ each represent independently for each occurrence hydrogen or $C_1$-$C_4$alkyl;

$R_6$ and $R_7$ each represent independently for each occurrence hydrogen or alkyl, or when $R_6$ and $R_7$ are attached to the same atom, $R_6$ and $R_7$ are optionally taken together with the atom to which they are attached to form a 3-6 membered cycloalkyl or heterocycloalkyl group;

$R_8$ and $R_9$ each represent independently for each occurrence hydrogen, alkyl, cycloalkyl, heterocycloalkyl, aryl, heteroaryl, aralkyl, or heteroaralkyl; or when $R_8$ and $R_9$ are attached to the same atom, $R_8$ and $R_9$ are optionally taken together with the atom to which they are attached to form a 3-6 membered cycloalkyl or heterocycloalkyl group;

$R_{10}$ represents independently for each occurrence alkyl, cycloalkyl, heterocycloalkyl, aryl, heteroaryl, aralkyl, or heteroaralkyl;

W is $C_1$-$C_6$alkyl or $C_4$-$C_{10}$cycloalkyl, each of which are optionally substituted with one or two substituents independently selected from the group consisting of $C_1$-$C_6$alkyl, $C_1$-$C_6$haloalkyl, cycloalkyl, —$OC_1$-$C_6$alkyl, —O-cycloalkyl, —OH, and fluoro;

m is 1 or 2; and n is 0, 1, 2, 3, or 4.

In certain embodiments, $R_1$ is a —O—$(CR_6R_7)_n$-heterocycloalkyl group, wherein the heterocycloalkyl group is a 5-7 membered ring containing 1 or 2 ring oxygen or sulfur atoms and the ring is optionally substituted with one or more substituents independently selected from the group consisting of halogen, $C_1$-$C_6$alkyl, $C_1$-$C_6$alkoxyl, hydroxyl, —$N(R_8)R_9$, —$C(O)R_{10}$, —$CO_2R_8$, —$CON(R_8)R_9$, —$N(R_8)COR_{10}$, —$N(R_8)SO_2R_{10}$, —$SO_2N(R_8)R_9$, —$N(R_8)SO_2N(R_8)R_9$, and —$SO_2R_{10}$. In certain embodiments, $R_1$ is a —O—$(CR_6R_7)_n$—$C_5$-$C_7$heterocycloalkyl group containing 1 or 2 ring oxygen or sulfur atoms, and wherein the heterocycloalkyl group is optionally substituted with one or more substituents independently selected from the group consisting of halogen, $C_1$-$C_6$alkyl, $C_1$-$C_6$alkoxyl, —$C(O)R_{10}$, —$CO_2R_8$, —$CONR_8R_9$, —$NR_8COR_{10}$, —$NR_8SO_2R_{10}$, —$SO_2NR_8R_9$, and —$SO_2R_{10}$. In certain embodiments, $R_1$ is a —O—$(CR_6R_7)_n$-heterocycloalkyl group, wherein the heterocycloalkyl group is a 5-7 membered ring containing 1 or 2 ring oxygen or sulfur atoms and the ring is optionally substituted with one or more substituents independently selected from the group consisting of halogen and $C_1$-$C_6$alkyl. In certain embodiments, $R_1$ is —O—$(CR_6R_7)_n$-tetrahydrofuranyl, —O—$(CR_6R_7)_n$-tetrahydropyranyl, —O—$(CR_6R_7)_n$-dioxanyl, or —O—$(CR_6R_7)_n$-oxetanyl. In certain embodiments, $R_1$ is —O—$(CR_6R_7)_n$-tetrahydrofuranyl or —O—$(CR_6R_7)_n$-tetrahydropyranyl.

In certain embodiments, $R_2$ is —O—$(CR_6R_7)_n$-heterocycloalkyl, —O-heterocycloalkyl, or heterocycloalkyl; wherein the heterocycloalkyl groups are optionally substituted with one or more substituents independently selected from the group consisting of halogen, $C_1$-$C_6$alkyl, $C_1$-$C_6$alkoxyl, hydroxyl, —$N(R_8)R_9$, —$C(O)R_{10}$, —$CO_2R_8$, —$OC(O)R_9$, —$CON(R_8)R_9$, —$N(R_8)COR_{10}$, —$N(R_8)SO_2R_{10}$, —$SO_2N(R_8)R_9$, and —$SO_2R_{10}$. In certain embodiments, $R_2$ is —O—$(CR_6R_7)_n$— heterocycloalkyl or —O-heterocycloalkyl; wherein the heterocycloalkyl groups are optionally substituted with one or more substituents independently selected from the group consisting of halogen, $C_1$-$C_6$alkyl, and $C_1$-$C_6$alkoxyl. In certain embodiments, $R_2$ is —O—$(CR_6R_7)_n$-tetrahydrofuranyl, —O—$(CR_6R_7)_n$-tetrahydropyranyl, —O—$(CR_6R_7)_n$-morpholinyl, —O-tetrahydrofuranyl, or —O-tetrahydropyranyl. In certain embodiments, $R_2$ is —O—$(CR_6R_7)_n$-tetrahydrofuranyl, —O—$(CR_6R_7)_n$-tetrahydropyranyl, —O—$(CR_6R_7)_n$-morpholinyl, —O-tetrahydrofuranyl, —O—$(CR_6R_7)_n$-oxetanyl, or —O-tetrahydropyranyl.

In certain embodiments, $R_3$ is hydrogen, halogen, $C_1$-$C_6$alkyl, $C_1$-$C_6$alkoxyl, hydroxyl, —$NR_8R_9$, —CN, or —$C(O)R_{10}$. In certain embodiments, $R_3$ is hydrogen, halogen, $C_1$-$C_6$alkyl, or $C_1$-$C_6$alkoxyl. In certain embodiments, $R_3$ is hydrogen, and m is 1.

In certain embodiments, $R_4$ is hydrogen or methyl, and $R_5$ is hydrogen. In certain embodiments, $R_4$ and $R_5$ are hydrogen. In certain embodiments, $R_4$ is methyl, and $R_5$ is hydrogen. In certain embodiments, $R_6$ and $R_7$ each represent independently for each occurrence hydrogen or methyl.

In certain embodiments, $R_8$ and $R_9$ each represent independently for each occurrence hydrogen, methyl, ethyl, n-propyl, isopropyl, butyl, cyclopropyl, cyclobutyl, phenyl, or benzyl. In certain embodiments, $R_8$ and $R_9$ each represent independently for each occurrence hydrogen, methyl, isopropyl, or cyclopropyl. In certain embodiments, $R_8$ and $R_9$ each represent independently for each occurrence hydrogen or methyl. In certain embodiments, $R_{10}$ is methyl, ethyl, n-propyl, isopropyl, butyl, cyclopropyl, cyclobutyl, phenyl, or benzyl.

In certain embodiments, n is 0. In certain embodiments, n is 1.

In certain embodiments, W is $C_4$-$C_{10}$cycloalkyl optionally substituted with one or two substituents independently selected from the group consisting of $C_1$-$C_6$alkyl, —$CF_3$, and fluoro. In certain embodiments, W is selected from the group consisting of cyclobutyl, cycloheptyl, cyclohexyl, 4-methylcyclohexyl, 4-ethylcyclohexyl, 4-trifluoromethylcyclohexyl, 1-methylcyclohexyl, 1,5-dimethylcyclohexyl, cyclopentyl, isopropyl, and bicyclo[2,2,1]heptyl. In certain embodiments, W is selected from the group consisting of cyclobutyl, cyclohexyl, cycloheptyl, 4-methylcyclohexyl, 4-ethylcyclohexyl, 4-trifluoromethylcyclohexyl, cyclopentyl, and —$CH_2$cyclohexyl. In certain embodiments, W is cyclohexyl substituted with one or two substituents independently selected from the group consisting of $C_1$-$C_6$alkyl, —$CF_3$, and fluoro. In certain embodiments, W is cyclohexyl substituted with one or two $C_1$-$C_6$alkyl. In certain embodiments, W is cyclohexyl substituted with one or two substituents independently selected from the group consisting of methyl, ethyl, n-propyl, isopropyl, n-butyl, sec-butyl, isobutyl, and tert-butyl.

Another aspect of the invention provides a compound of Formula IIA:

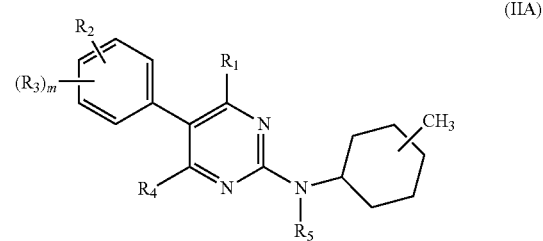

(IIA)

or a pharmaceutically acceptable salt or N-oxide thereof, wherein:

$R_1$ is a —O—$(CR_6R_7)_n$-heterocycloalkyl group, wherein the heterocycloalkyl group is an unsubstituted 5-7 membered ring containing 1 or 2 ring oxygen or sulfur atoms;

$R_2$ is —O—$(CR_6R_7)_n$-heterocycloalkyl, —O—$(CR_6R_7)_n$—$C_1$-$C_6$alkoxyl, or —$(CR_6R_7)_n$-heterocycloalkyl; wherein the heterocycloalkyl groups are optionally substituted with one or more substituents independently selected from the group consisting of halogen, $C_1$-$C_6$alkyl, $C_1$-$C_6$alkoxyl, hydroxyl, —N($R_8$)$R_9$, —C(O)$R_{10}$, —$CO_2R_8$, and —CON($R_8$)$R_9$; provided that $R_2$ is not morpholinyl;

$R_3$ is hydrogen, halogen, or $C_1$-$C_6$alkyl;

$R_4$, $R_5$, $R_6$, $R_7$, $R_8$, and $R_9$ each represent independently for each occurrence hydrogen or methyl;

$R_{10}$ represents independently for each occurrence alkyl, cycloalkyl, or heterocycloalkyl;

m is 1 or 2; and n is 0, 1, 2, 3, or 4.

In certain embodiments, the definition of the variables for Formula IIA correspond to one or more of the embodiments described above for the definitions of the variables associated with Formula II to the extent the definition does not expand the scope of compounds embraced by Formula IIA beyond that defined originally.

Another aspect of the invention provides a compound of Formula III:

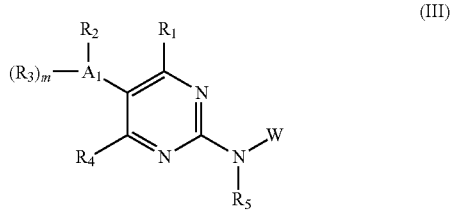

(III)

or a pharmaceutically acceptable salt or N-oxide thereof, wherein:

$R_1$ is —O—(CR$_6$R$_7$)$_n$-A$_2$, —N(R$_6$)(CR$_6$R$_7$)$_n$-A$_2$, —S—(CR$_6$R$_7$)$_n$-A$_2$, or heterocycloalkyl, wherein said heterocycloalkyl is optionally substituted with one or more substituents independently selected from the group consisting of halogen, $C_1$-$C_6$alkyl, $C_3$-$C_6$cycloalkyl, $C_2$-$C_4$alkenyl, $C_2$-$C_4$alkynyl, $C_1$-$C_6$alkoxyl, hydroxyl, —$CF_3$, —$CH_2F$, —$CHF_2$, —N($R_8$)$R_9$, —CN, —C(O)$R_{10}$, —$CO_2R_8$, —OC(O)$R_9$, —CON($R_8$)$R_9$, —N($R_8$)COR$_{10}$, —N($R_8$)SO$_2$R$_{10}$, —SO$_2$N($R_8$)$R_9$, —N($R_8$)SO$_2$N($R_8$)$R_9$, and —SO$_2R_{10}$;

$R_2$ is —O-heterocycloalkyl, —O-heterocycloalkenyl, —Y-heterocycloalkyl, —Y-heterocycloalkenyl, heterocycloalkyl, -heterocycloalkenyl, -cycloalkyl, -cycloalkenyl, —(CR$_6$R$_7$)$_n$—$C_1$-$C_6$alkoxyl, —O—(CR$_6$R$_7$)$_n$—$C_1$-$C_6$alkoxyl, $C_1$-$C_6$alkoxyl, halogen, —$CF_3$, —$CH_2F$, —$CHF_2$, —$OCF_3$, —$OCH_2F$, hydroxyl, or $C_1$-$C_6$alkyl, wherein said heterocycloalkyl, heterocycloalkenyl, cycloalkyl, and cycloalkenyl are optionally substituted with one or more substituents independently selected from the group consisting of halogen, $C_1$-$C_6$alkyl, $C_3$-$C_6$cycloalkyl, $C_2$-$C_4$alkenyl, $C_2$-$C_4$alkynyl, $C_1$-$C_6$alkoxyl, hydroxyl, —$CF_3$, —$CH_2F$, —$CHF_2$, —$OCF_3$, —N($R_8$)$R_9$, —CN, —C(O)$R_{10}$, —$CO_2R_8$, —OC(O)$R_9$, —CON($R_8$)$R_9$, —N($R_8$)COR$_{10}$, —N($R_8$)SO$_2$R$_{10}$, —SO$_2$N($R_8$)$R_9$, —N($R_8$)SO$_2$N($R_8$)$R_9$, and —SO$_2R_{10}$;

$R_3$ is hydrogen, halogen, $C_1$-$C_6$alkyl, $C_3$-$C_6$cycloalkyl, $C_2$-$C_4$alkenyl, $C_2$-$C_4$alkynyl, $C_1$-$C_6$alkoxyl, hydroxyl, —$CF_3$, —$CH_2F$, —$CHF_2$, —$OCF_3$, —$OCH_2F$, —N($R_8$)$R_9$, —CN, —C(O)$R_{10}$, —$CO_2R_8$, —CON($R_8$)$R_9$, —N($R_8$)COR$_{10}$, —N($R_8$)SO$_2$R$_{10}$, —SO$_2$N($R_8$)$R_9$, or —SO$_2R_{10}$;

$R_4$ is $C_1$-$C_4$alkyl, —(CR$_6$R$_7$)$_n$—$C_1$-$C_6$alkoxyl, or —$CO_2C_1$-$C_6$alkyl;

$R_5$ is hydrogen or $C_1$-$C_4$alkyl;

$R_6$ and $R_7$ each represent independently for each occurrence hydrogen or alkyl, or when $R_6$ and $R_7$ are attached to the same atom, $R_6$ and $R_7$ are optionally taken together with the atom to which they are attached to form a 3-6 membered cycloalkyl or heterocycloalkyl group;

$R_8$ and $R_9$ each represent independently for each occurrence hydrogen, alkyl, cycloalkyl, heterocycloalkyl, aryl, heteroaryl, aralkyl, or heteroaralkyl; or when $R_8$ and $R_9$ are attached to the same atom, $R_8$ and $R_9$ are optionally taken together with the atom to which they are attached to form a 3-6 membered cycloalkyl or heterocycloalkyl group;

$R_{10}$ represents independently for each occurrence alkyl, cycloalkyl, heterocycloalkyl, aryl, heteroaryl, aralkyl, or heteroaralkyl;

$A_1$ is phenylene or a monocyclic heteroarylene group;

$A_2$ is heterocycloalkyl optionally substituted with one or more substituents independently selected from the group consisting of halogen, $C_1$-$C_6$alkyl, $C_2$-$C_4$alkenyl, $C_2$-$C_4$alkynyl, $C_1$-$C_6$alkoxyl, $C_3$-$C_6$cycloalkyl, hydroxyl, —$CF_3$, —$CH_2F$, —$CHF_2$, —N($R_8$)$R_9$, —CN, —C(O)$R_{10}$, —$CO_2R_8$, —OC(O)$R_9$, —CON($R_8$)$R_9$, —N($R_8$)COR$_{10}$, —N($R_8$)SO$_2$R$_{10}$, —SO$_2$N($R_8$)$R_9$, —N($R_8$)SO$_2$N($R_8$)$R_9$, and —SO$_2R_{10}$;

W is $C_1$-$C_6$alkyl or $C_4$-$C_{10}$cycloalkyl, each of which are optionally substituted with one, two, or three substituents independently selected from the group consisting of $C_1$-$C_6$alkyl, $C_1$-$C_6$haloalkyl, cycloalkyl, —$OC_1$-$C_6$alkyl, —O-cycloalkyl, —OH, —$CF_3$, and fluoro;

Y is —N($R_8$)—, —S—, —S(O)—, or —S(O)$_2$—;

m is 1 or 2; and n is 0, 1, 2, 3, or 4.

In certain embodiments, $R_1$ is —O—(CR$_6$R$_7$)$_n$-A$_2$ or a heterocycloalkyl group optionally substituted with one or more substituents independently selected from the group consisting of halogen, $C_1$-$C_6$alkyl, $C_3$-$C_6$cycloalkyl, —C(O)$R_{10}$, —$CO_2R_8$, —OC(O)$R_9$, —CON($R_8$)$R_9$, —N($R_8$)COR$_{10}$, —N($R_8$)SO$_2$R$_{10}$, —SO$_2$N($R_8$)$R_9$, —N($R_8$)SO$_2$N($R_8$)$R_9$, and —SO$_2R_{10}$. In certain embodiments, $R_1$ is —O—(CR$_6$R$_7$)$_n$-A$_2$.

In certain embodiments, A$_2$ is a heterocycloalkyl group containing at least one nitrogen or sulfur atom, and wherein said heterocycloalkyl group is optionally substituted with one or more substituents independently selected from the group consisting of halogen, $C_1$-$C_6$alkyl, $C_3$-$C_6$cycloalkyl, —C(O)$R_{10}$, —$CO_2R_8$, —OC(O)$R_9$, —CON($R_8$)$R_9$, —N($R_8$)COR$_{10}$, —N($R_8$)SO$_2$R$_{10}$, —SO$_2$N($R_8$)$R_9$, —N($R_8$)SO$_2$N($R_8$)$R_9$, and —SO$_2R_{10}$. In certain embodiments, A$_2$ is a heterocycloalkyl group containing at least one nitrogen or sulfur atom, and wherein said heterocycloalkyl group is substituted with one or more substituents independently selected from the group consisting of —CON($R_8$)$R_9$, —SO$_2$N($R_8$)$R_9$, and —SO$_2R_{10}$. In certain embodiments, A$_2$ is a 3-6 membered heterocycloalkyl group containing at least one nitrogen, and wherein said heterocycloalkyl group is substituted with —SO$_2R_{10}$. In certain embodiments, A$_2$ is an azetidinyl, pyrrolidinyl, piperidinyl or morpholinyl, each of which is substituted with —CON($R_8$)$R_9$, —SO$_2$N($R_8$)$R_9$, or —SO$_2R_{10}$. In certain embodiments, A$_2$ is azetidinyl substituted with —CON($R_8$)$R_9$, —SO$_2$N($R_8$)$R_9$, or —SO$_2R_{10}$.

In certain other embodiments, A$_2$ is a heterocycloalkyl group containing at least one nitrogen or sulfur atom, and wherein said heterocycloalkyl group is substituted with one or more substituents independently selected from the group consisting of —$CO_2R_8$, —CON($R_8$)$R_9$, —SO$_2$N($R_8$)$R_9$, and —SO$_2R_{10}$. In certain embodiments, A$_2$ is a 3-6 membered heterocycloalkyl group containing at least one nitrogen, and wherein said heterocycloalkyl group is substituted with —$CO_2R_8$, —SO$_2$N($R_8$)$R_9$, or —SO$_2R_{10}$. In certain embodiments, A$_2$ is an azetidinyl, pyrrolidinyl, piperidinyl or morpholinyl, each of which is substituted with —CON($R_8$)$R_9$, —$CO_2R_8$, —SO$_2$N($R_8$)$R_9$, or —SO$_2R_{10}$. In certain embodiments, $A_2$ is azetidinyl, pyrrolidinyl, or piperidinyl, each substituted with —CON($R_8$)$R_9$, —CO$_2$$R_8$, —SO$_2$N($R_8$)$R_9$, or —SO$_2$$R_{10}$.

In certain embodiments, $A_2$ is one of the following:

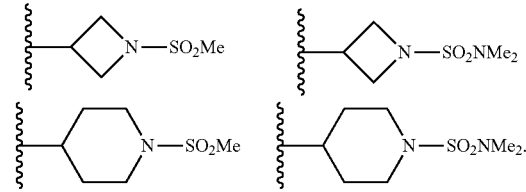

In certain other embodiments, $A_2$ is

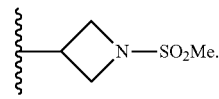

In certain embodiments, n is 0 or 1. In certain other embodiments, n is 0. In certain other embodiments, n is 1. In certain embodiments, m is 1.

In certain embodiments, $R_1$ is a heterocycloalkyl group containing at least one nitrogen or sulfur atom, and wherein said heterocycloalkyl group is optionally substituted with one or more substituents independently selected from the group consisting of halogen, $C_1$-$C_6$alkyl, —C(O)$R_{10}$, —CO$_2$$R_8$, —OC(O)$R_9$, —CON($R_8$)$R_9$, —N($R_8$)COR$_{10}$, —N($R_8$)SO$_2$$R_{10}$, —SO$_2$N($R_8$)$R_9$, —N($R_8$)SO$_2$N($R_8$)$R_9$, and —SO$_2$$R_{10}$. In certain embodiments, $R_1$ is a heterocycloalkyl group optionally substituted with one or more substituents independently selected from the group consisting of halogen, $C_1$-$C_6$alkyl, —CO$_2$$R_8$, —CON($R_8$)$R_9$, —SO$_2$N($R_8$)$R_9$, and —SO$_2$$R_{10}$. In certain embodiments, $R_1$ is a heterocycloalkyl group containing at least one nitrogen or sulfur atom, and wherein said heterocycloalkyl group is optionally substituted with one or more substituents independently selected from the group consisting of halogen and $C_1$-$C_6$alkyl. In certain embodiments, $R_1$ is morpholino, azetidinyl, piperidinyl, or pyrrolidinyl.

In certain embodiments, $R_2$ is —O-heterocycloalkyl or —O—(CR$_6$R$_7$)$_n$—$C_1$-$C_6$alkoxyl; wherein said heterocycloalkyl is optionally substituted with one or more substituents independently selected from the group consisting of halogen, $C_1$-$C_6$alkyl, $C_1$-$C_6$alkoxyl, hydroxyl, —N($R_8$)$R_9$, —C(O)$R_{10}$, —CO$_2$$R_8$, —OC(O)$R_9$, —CON($R_8$)$R_9$, —N($R_8$)COR$_{10}$, —N($R_8$)SO$_2$$R_{10}$, —SO$_2$N($R_8$)$R_9$, —N($R_8$)SO$_2$N($R_8$)$R_9$, and —SO$_2$$R_{10}$. In certain embodiments, $R_2$ is —O-heterocycloalkyl or —O—(CR$_6$R$_7$)$_n$—$C_1$-$C_6$alkoxyl; wherein said heterocycloalkyl is optionally substituted with one or more substituents independently selected from the group consisting of halogen, $C_1$-$C_6$alkyl, —CO$_2$$R_8$, and —CON($R_8$)$R_9$. In certain embodiments, $R_2$ is —O-heterocycloalkyl; wherein said heterocycloalkyl is optionally substituted with one or more substituents independently selected from the group consisting of halogen and $C_1$-$C_6$alkyl. In certain embodiments, $R_2$ is morpholinyl, —O-tetrahydrofuranyl, O-tetrahydropyranyl, —O-pyrrolidinyl, or —O-piperidinyl. In certain embodiments, $R_2$ is —O-tetrahydrofuranyl.

In certain other embodiments, $R_2$ is —O-heterocycloalkyl or —O—(CR$_6$R$_7$)$_n$—$C_1$-$C_6$alkoxyl; wherein said heterocycloalkyl is optionally substituted with one or more substituents independently selected from the group consisting of halogen, $C_1$-$C_6$alkyl, —CO$_2$$R_8$, —CON($R_8$)$R_9$, —SO$_2$N ($R_8$)$R_9$, and —SO$_2$$R_{10}$. In certain other embodiments, $R_2$ is —O-heterocycloalkyl; wherein said heterocycloalkyl is optionally substituted with one or more substituents independently selected from the group consisting of —CO$_2$$R_8$, —CON($R_8$)$R_9$, —SO$_2$N($R_8$)$R_9$, and —SO$_2$$R_{10}$. In certain other embodiments, $R_2$ is morpholinyl, —O-tetrahydrofuranyl, O-tetrahydropyranyl, —O-pyrrolidinyl, O-azetidinyl or —O-piperidinyl; wherein said pyrrolidinyl, azetidinyl or piperidinyl each independently is optionally substituted with one or more substituents independently selected from the group consisting of, —CO$_2$$R_8$, —CON($R_8$)$R_9$, —SO$_2$N($R_8$)$R_9$, and —SO$_2$$R_1$ In certain embodiments, $R_3$ is hydrogen, halogen, —OCF$_3$, —OCH$_2$F, —CF$_3$, $C_1$-$C_6$alkyl, or $C_1$-$C_6$alkoxy. In certain embodiments, $R_3$ is halogen, $C_1$-$C_6$alkyl, $C_1$-$C_6$alkoxyl, hydroxyl, —NR$_8$R$_9$, —CN, or —C(O)R$_{10}$. In certain embodiments, $R_3$ is halogen, $C_1$-$C_6$alkyl, or $C_1$-$C_6$alkoxyl. In certain embodiments, $R_3$ is hydrogen, and m is 1.

In certain embodiments, $R_5$ is hydrogen. In certain embodiments, $R_6$ and $R_7$ each represent independently for each occurrence hydrogen or methyl.

In certain embodiments, $R_8$ and $R_9$ each represent independently for each occurrence hydrogen, methyl, ethyl, n-propyl, isopropyl, butyl, cyclopropyl, cyclobutyl, phenyl, or benzyl, or $R_8$ and $R_9$ are optionally taken together with the atom to which they are attached to form a 3-6 membered cycloalkyl or heterocycloalkyl group. In certain embodiments, $R_8$ and $R_9$ each represent independently for each occurrence hydrogen, methyl, ethyl or cyclopropyl. In certain embodiments, $R_8$ and $R_9$ each represent independently for each occurrence hydrogen, methyl, ethyl, propyl, butyl, cyclopropyl, cyclobutyl, phenyl, or benzyl. In certain embodiments, $R_8$ and $R_9$ each represent independently for each occurrence hydrogen or methyl. In certain embodiments, $R_{10}$ is methyl, ethyl, n-propyl, isopropyl, butyl, cyclopropyl, cyclobutyl, phenyl, or benzyl.

In certain embodiments, $A_1$ is phenylene.

In certain embodiments, W is $C_5$-$C_{10}$cycloalkyl optionally substituted with one or two substituents independently selected from the group consisting of $C_1$-$C_6$alkyl and fluoro. In certain embodiments, W is $C_5$-$C_{10}$cycloalkyl optionally substituted with one or two substituents independently selected from the group consisting of $C_1$-$C_6$alkyl, —CF$_3$, and fluoro. In certain embodiments, W is cyclohexyl substituted with one or two substituents independently selected from the group consisting of $C_1$-$C_6$alkyl, —CF$_3$, and fluoro. In certain embodiments, W is selected from the group consisting of cyclobutyl, cycloheptyl, cyclohexyl, 4-methylcyclohexyl, 4-ethylcyclohexyl, 4-trifluoromethylcyclohexyl, 1-methylcyclohexyl, 1,5-dimethylcyclohexyl, cyclopentyl, isopropyl, and bicyclo[2,2,1]heptyl. In certain embodiments, W is selected from the group consisting of cyclobutyl, cyclohexyl, cycloheptyl, 4-methylcyclohexyl, 4-ethylcyclohexyl, 4-trifluoromethylcyclohexyl, cyclopentyl, and —CH$_2$cyclohexyl. In certain embodiments, W is cyclohexyl substituted with one or two $C_1$-$C_6$alkyl. In certain embodiments, W is cyclohexyl substituted with one or two substituents independently selected from the group consisting of methyl, ethyl, n-propyl, isopropyl, n-butyl, sec-butyl, isobutyl, and tert-butyl.

Another aspect of the invention provides a compound of Formula IV:

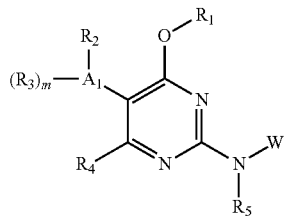

(IV)

or a pharmaceutically acceptable salt or N-oxide thereof, wherein:

$R_1$ is —$(CR_6R_7)_n$—$CON(R_8)R_9$, —$(CR_6R_7)_n$—$N(R_8)COR_{10}$, —$(CR_6R_7)_n$—$CON(R_8)SO_2R_{10}$, —$(CR_6R_7)_n$—C($CH_2OH$)(H)—$(CR_6R_7)_n$—OH, or —$(CR_6R_7)_n$—$C_1$-$C_6$alkoxyl;

$R_2$ is —O-heterocycloalkyl, —O-heterocycloalkenyl, —Y-heterocycloalkyl, —Y-heterocycloalkenyl, heterocycloalkyl, -heterocycloalkenyl, -cycloalkyl, -cycloalkenyl, —$(CR_6R_7)_n$—$C_1$-$C_6$alkoxyl, —O—$(CR_6R_7)_n$—$C_1$-$C_6$alkoxyl, $C_1$-$C_6$alkoxyl, halogen, —$CF_3$, —$CHF_2$, —$CHF$, —$OCF_3$, —$OCH_2F$, hydroxyl, or $C_1$-$C_6$alkyl, wherein said heterocycloalkyl, heterocycloalkenyl, cycloalkyl, and cycloalkenyl are optionally substituted with one or more substituents independently selected from the group consisting of halogen, $C_1$-$C_6$alkyl, $C_3$-$C_6$cycloalkyl, $C_2$-$C_4$alkenyl, $C_2$-$C_4$alkynyl, $C_1$-$C_6$alkoxyl, hydroxyl, —$CF_3$, —$CHF_2$, —$CHF$, —$OCF_3$, —$N(R_8)R_9$, —CN, —$C(O)R_{10}$, —$CO_2R_8$, —$OC(O)R_9$, —$CON(R_8)R_9$, —$N(R_8)COR_{10}$, —$N(R_8)SO_2R_{10}$, —$SO_2N(R_8)R_9$, —$N(R_8)SO_2N(R_8)R_9$, and —$SO_2R_{10}$;

$R_3$ is hydrogen, halogen, $C_1$-$C_6$alkyl, $C_3$-$C_6$cycloalkyl, $C_2$-$C_4$alkenyl, $C_2$-$C_4$alkynyl, $C_1$-$C_6$alkoxyl, hydroxyl, —$CF_3$, —$CHF_2$, —$CHF$, —$OCF_3$, —$OCH_2F$, —$N(R_8)R_9$, —CN, —$C(O)R_{10}$, —$CO_2R_8$, —$CON(R_8)R_9$, —$N(R_8)COR_{10}$, —$N(R_8)SO_2R_{10}$, —$SO_2N(R_8)R_9$, or —$SO_2R_{10}$;

$R_4$ is hydrogen, halogen, $C_1$-$C_4$alkyl, cyclopropyl, —CN, or —$CF_3$;

$R_5$ is hydrogen or $C_1$-$C_4$alkyl;

$R_6$ and $R_7$ each represent independently for each occurrence hydrogen or alkyl, or when $R_6$ and $R_7$ are attached to the same atom, $R_6$ and $R_7$ are optionally taken together with the atom to which they are attached to form a 3-6 membered cycloalkyl or heterocycloalkyl group;

$R_8$ and $R_9$ each represent independently for each occurrence hydrogen, alkyl, cycloalkyl, heterocycloalkyl, aryl, heteroaryl, aralkyl, or heteroaralkyl; or when $R_8$ and $R_9$ are attached to the same atom, $R_8$ and $R_9$ are optionally taken together with the atom to which they are attached to form a 3-6 membered cycloalkyl or heterocycloalkyl group;

$R_{10}$ represents independently for each occurrence alkyl, cycloalkyl, heterocycloalkyl, aryl, heteroaryl, aralkyl, or heteroaralkyl;

$A_1$ is phenylene or a monocyclic heteroarylene group;

W is $C_1$-$C_6$alkyl or $C_4$-$C_{10}$cycloalkyl, each of which are optionally substituted with one, two, or three substituents independently selected from the group consisting of $C_1$-$C_6$alkyl, $C_1$-$C_6$haloalkyl, cycloalkyl, —$OC_1$-$C_6$alkyl, —O-cycloalkyl, —OH, —$CF_3$, and fluoro;

Y is —$N(R_8)$—, —S—, —S(O)—, or —$S(O)_2$—;

m is 1 or 2; and n is 0, 1, 2, 3, or 4.

In certain embodiments, n is 0 or 1. In certain other embodiments, n is 0. In certain other embodiments, n is 1. In certain embodiments, m is 1.

In certain embodiments, $R_2$ is —O-heterocycloalkyl or —O—$(CR_6R_7)_n$—$C_1$-$C_6$alkoxyl; wherein said heterocycloalkyl is optionally substituted with one or more substituents independently selected from the group consisting of halogen, $C_1$-$C_6$alkyl, $C_1$-$C_6$alkoxyl, hydroxyl, —$N(R_8)R_9$, —$C(O)R_{10}$, —$CO_2R_8$, —$OC(O)R_9$, —$CON(R_8)R_9$, —$N(R_8)COR_{10}$, —$N(R_8)SO_2R_{10}$, —$SO_2N(R_8)R_9$, —$N(R_8)SO_2N(R_8)R_9$, and —$SO_2R_{10}$. In certain embodiments, $R_2$ is —O-heterocycloalkyl or —O—$(CR_6R_7)_n$—$C_1$-$C_6$alkoxyl; wherein said heterocycloalkyl is optionally substituted with one or more substituents independently selected from the group consisting of halogen, $C_1$-$C_6$alkyl, —$CO_2R_8$, and —$CON(R_8)R_9$. In certain embodiments, $R_2$ is —O-heterocycloalkyl; wherein said heterocycloalkyl is optionally substituted with one or more substituents independently selected from the group consisting of halogen and $C_1$-$C_6$alkyl. In certain embodiments, $R_2$ is morpholinyl, —O-tetrahydrofuranyl, O-tetrahydropyranyl, —O-pyrrolidinyl, or —O-piperidinyl. In certain embodiments, $R_2$ is —O-tetrahydrofuranyl.

In certain other embodiments, $R_2$ is —O-heterocycloalkyl or —O—$(CR_6R_7)_n$—$C_1$-$C_6$alkoxyl; wherein said heterocycloalkyl is optionally substituted with one or more substituents independently selected from the group consisting of halogen, $C_1$-$C_6$alkyl, —$CO_2R_8$, —$CON(R_8)R_9$, —$SO_2N(R_8)R_9$, and —$SO_2R_{10}$. In certain other embodiments, $R_2$ is —O-heterocycloalkyl; wherein said heterocycloalkyl is optionally substituted with one or more substituents independently selected from the group consisting of —$CO_2R_8$, —$CON(R_8)R_9$, —$SO_2N(R_8)R_9$, and —$SO_2R_{10}$. In certain other embodiments, $R_2$ is morpholinyl, —O-tetrahydrofuranyl, O-tetrahydropyranyl, —O-pyrrolidinyl, O-azetidinyl or —O-piperidinyl; wherein said pyrrolidinyl, azetidinyl or piperidinyl each independently is optionally substituted with one or more substituents independently selected from the group consisting of, —$CO_2R_8$, —$CON(R_8)R_9$, —$SO_2N(R_8)R_9$, and —$SO_2R_1$.

In certain embodiments, $R_3$ is hydrogen, halogen, —$OCF_3$, —$OCH_2F$, —$CF_3$, $C_1$-$C_6$alkyl, or $C_1$-$C_6$alkoxy. In certain embodiments, $R_3$ is halogen, $C_1$-$C_6$alkyl, $C_1$-$C_6$alkoxyl, hydroxyl, —$NR_8R_9$, —CN, or —$C(O)R_{10}$. In certain embodiments, $R_3$ is halogen, $C_1$-$C_6$alkyl, or $C_1$-$C_6$alkoxyl. In certain embodiments, $R_3$ is hydrogen, and m is 1.

In certain embodiments, $R_4$ is hydrogen or methyl, and $R_5$ are hydrogen. In certain embodiments, $R_4$ and $R_5$ are hydrogen. In certain embodiments, $R_4$ is methyl; and $R_5$ is hydrogen. In certain embodiments, $R_6$ and $R_7$ each represent independently for each occurrence hydrogen or methyl.

In certain embodiments, $R_8$ and $R_9$ each represent independently for each occurrence hydrogen, methyl, ethyl, n-propyl, isopropyl, butyl, cyclopropyl, cyclobutyl, phenyl, or benzyl, or $R_8$ and $R_9$ are optionally taken together with the atom to which they are attached to form a 3-6 membered cycloalkyl or heterocycloalkyl group. In certain embodiments, $R_8$ and $R_9$ each represent independently for each occurrence hydrogen, methyl, ethyl or cyclopropyl. In certain embodiments, $R_8$ and $R_9$ each represent independently for each occurrence hydrogen, methyl, ethyl, propyl, butyl, cyclopropyl, cyclobutyl, phenyl, or benzyl. In certain embodiments, $R_8$ and $R_9$ each represent independently for each occurrence hydrogen or methyl. In certain embodiments, $R_{10}$ is methyl, ethyl, n-propyl, isopropyl, butyl, cyclopropyl, cyclobutyl, phenyl, or benzyl.

In certain embodiments, $A_1$ is phenylene.

In certain embodiments, W is $C_5$-$C_{10}$cycloalkyl optionally substituted with one or two substituents independently selected from the group consisting of $C_1$-$C_6$alkyl and fluoro. In certain embodiments, W is $C_5$-$C_{10}$cycloalkyl optionally substituted with one or two substituents independently selected from the group consisting of $C_1$-$C_6$alkyl, —$CF_3$, and fluoro. In certain embodiments, W is cyclohexyl substituted with one or two substituents independently selected from the group consisting of $C_1$-$C_6$alkyl, —$CF_3$, and fluoro. In certain embodiments, W is selected from the group consisting of cyclobutyl, cycloheptyl, cyclohexyl, 4-methylcyclohexyl, 4-ethylcyclohexyl, 4-trifluoromethylcyclohexyl, 1-methylcyclohexyl, 1,5-dimethylcyclohexyl, cyclopentyl, isopropyl, and bicyclo[2,2,1]heptyl. In certain embodiments, W is selected from the group consisting of cyclobutyl, cyclohexyl, cycloheptyl, 4-methylcyclohexyl, 4-ethylcyclohexyl, 4-trifluoromethylcyclohexyl, cyclopentyl, and —$CH_2$cyclohexyl. In certain embodiments, W is cyclohexyl substituted with one or two $C_1$-$C_6$alkyl. In certain embodiments, W is cyclohexyl substituted with one or two substituents independently selected from the group consisting of methyl, ethyl, n-propyl, isopropyl, n-butyl, sec-butyl, isobutyl, and tert-butyl.

In certain other embodiments, the compound is one of the compounds listed in Tables 1 or 2 below or a pharmaceutically acceptable salt or N-oxide thereof

TABLE 1

TABLE 1-continued

| No. | X | Y | Z |
|---|---|---|---|
| I-10 | tetrahydrofuran-3-yloxy-phenyl- | Me$_2$NO$_2$S—N(azetidine)—O— | cyclohexyl-CF$_3$ |
| I-11 | tetrahydrofuran-3-yloxy-phenyl- | Me$_2$NO$_2$S—N(azetidine)—O— | cyclohexyl-Me |
| I-12 | tetrahydrofuran-3-yloxy-phenyl- | Me$_2$NO$_2$S—N(azetidine)—O— | cyclohexyl-Et |
| I-13 | tetrahydrofuran-3-yloxy-phenyl- | MeO$_2$S—N(azetidine)—O— | cyclohexyl-CF$_3$ |
| I-14 | tetrahydrofuran-3-yloxy-phenyl- | MeO$_2$S—N(azetidine)—O— | cyclohexyl-Me |
| I-15 | tetrahydrofuran-3-yloxy-phenyl- | MeO$_2$S—N(azetidine)—O— | cyclohexyl-Et |
| I-16 | tetrahydrofuran-3-yloxy-phenyl- | morpholin-4-yl- | cyclohexyl-CF$_3$ |
| I-17 | tetrahydrofuran-3-yloxy-phenyl- | morpholin-4-yl- | cyclohexyl-Me |
| I-18 | tetrahydrofuran-3-yloxy-phenyl- | morpholin-4-yl- | cyclohexyl-Et |
| I-19 | MeO(C=O)-piperidin-4-yloxy-phenyl- | Me$_2$NO$_2$S—N(azetidine)—O— | cyclohexyl-CF$_3$ |
| I-20 | MeO(C=O)-piperidin-4-yloxy-phenyl- | Me$_2$NO$_2$S—N(azetidine)—O— | cyclohexyl-Me |

US 8,334,292 B1

TABLE 1-continued

| No. | X | Y | Z |
|---|---|---|---|
| I-21 | methyl 4-(4-...phenoxy)piperidine-1-carboxylate | Me$_2$NO$_2$S—N(azetidine)—O— | cyclohexyl-Et |
| I-22 | methyl 4-(4-...phenoxy)piperidine-1-carboxylate | MeO$_2$S—N(azetidine)—O— | cyclohexyl-CF$_3$ |
| I-23 | methyl 4-(4-...phenoxy)piperidine-1-carboxylate | MeO$_2$S—N(azetidine)—O— | 3-methylcyclohexyl |
| I-24 | methyl 4-(4-...phenoxy)piperidine-1-carboxylate | MeO$_2$S—N(azetidine)—O— | cyclohexyl-Et |
| I-25 | methyl 4-(4-...phenoxy)piperidine-1-carboxylate | morpholin-4-yl | cyclohexyl-CF$_3$ |
| I-26 | methyl 4-(4-...phenoxy)piperidine-1-carboxylate | morpholin-4-yl | 3-methylcyclohexyl |
| I-27 | methyl 4-(4-...phenoxy)piperidine-1-carboxylate | morpholin-4-yl | cyclohexyl-Et |
| I-28 | 4-(2-methoxyethoxy)phenyl | Me$_2$NO$_2$S—N(azetidine)—O— | cyclohexyl-CF$_3$ |
| I-29 | 4-(2-methoxyethoxy)phenyl | Me$_2$NO$_2$S—N(azetidine)—O— | 3-methylcyclohexyl |
| I-30 | 4-(2-methoxyethoxy)phenyl | Me$_2$NO$_2$S—N(azetidine)—O— | cyclohexyl-Et |

TABLE 1-continued
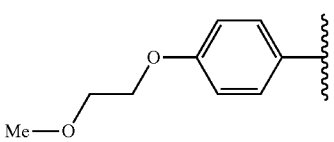
| No. | X | Y | Z |
|---|---|---|---|
| I-31 | 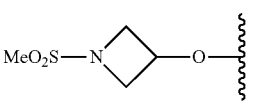 | 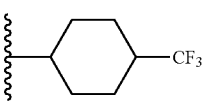 | 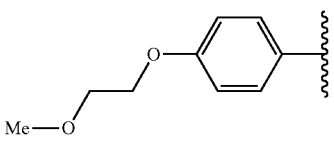 |
| I-32 | 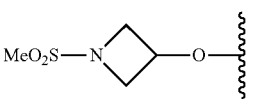 | 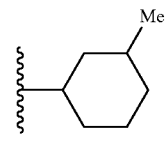 | 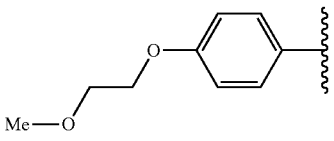 |
| I-33 | 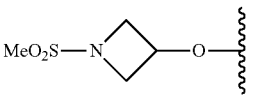 | 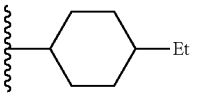 | 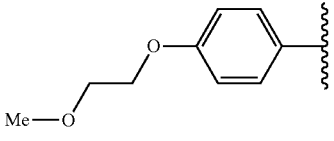 |
| I-34 | 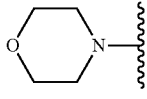 | 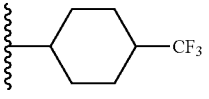 | 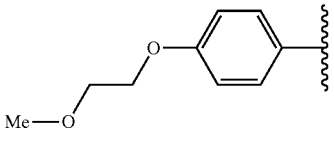 |
| I-35 | 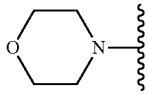 | 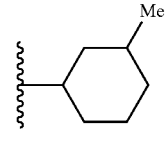 | 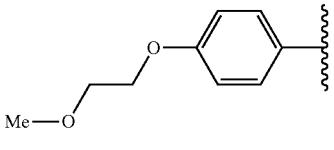 |
| I-36 | 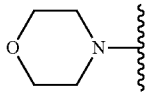 | 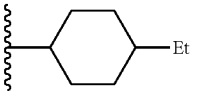 | 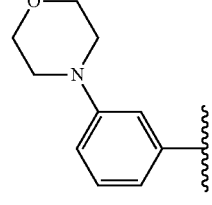 |
| I-37 | 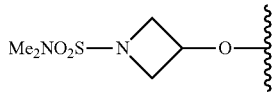 | 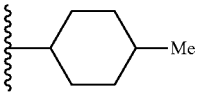 | 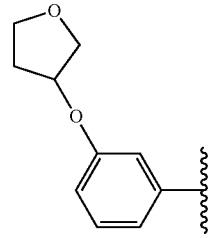 |
| I-38 | 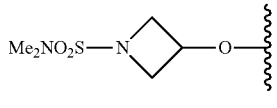 | 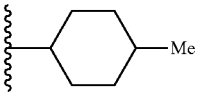 | |

TABLE 1-continued
| No. | X | Y | Z |
|---|---|---|---|
| I-39 | 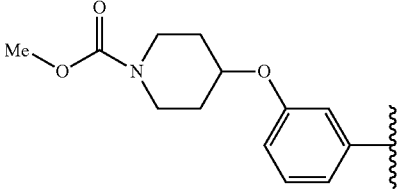 | 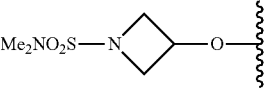 | 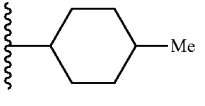 |
| I-40 | 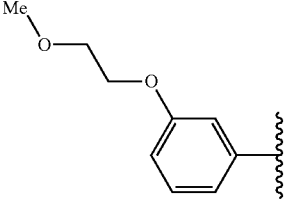 | 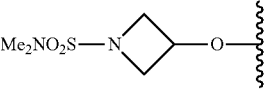 | 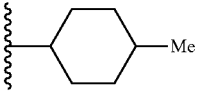 |
| I-41 | 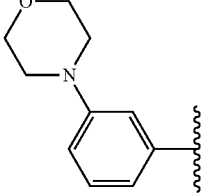 | 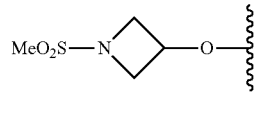 | 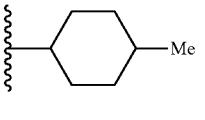 |
| I-42 | 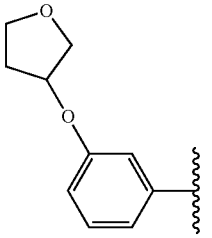 | 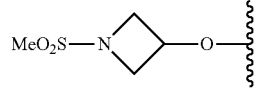 | 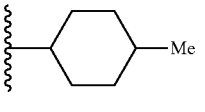 |
| I-43 | 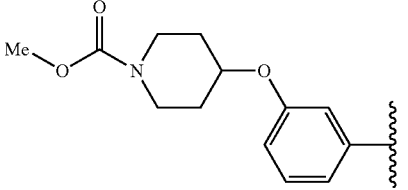 | 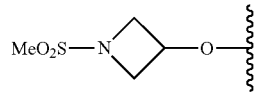 | 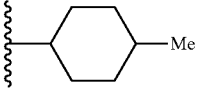 |
| I-44 | 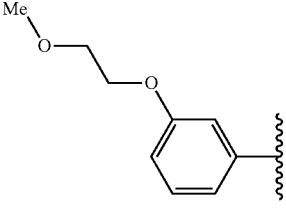 | 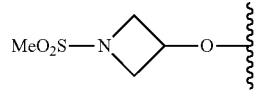 | 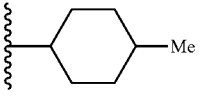 |

TABLE 1-continued

| No. | X | Y | Z |
|---|---|---|---|
| I-45 | 3-(morpholin-4-yl)phenyl | morpholin-4-yl | 4-methylcyclohexyl |
| I-46 | 3-((tetrahydrofuran-3-yl)oxy)phenyl | morpholin-4-yl | 4-methylcyclohexyl |
| I-47 | 3-((1-(methoxycarbonyl)piperidin-4-yl)oxy)phenyl | morpholin-4-yl | 4-methylcyclohexyl |
| I-48 | 3-(2-methoxyethoxy)phenyl | morpholin-4-yl | 4-methylcyclohexyl |
| I-49 | 4-((tetrahydrofuran-3-yl)oxy)phenyl | (1-(methylsulfonyl)pyrrolidin-3-yl)oxy | 4-methylcyclohexyl |
| I-50 | 4-((tetrahydrofuran-3-yl)oxy)phenyl | (1-(methylsulfonyl)piperidin-4-yl)oxy | 4-methylcyclohexyl |
| I-51 | 4-(morpholin-4-yl)phenyl | (1-(methylsulfonyl)pyrrolidin-3-yl)oxy | 4-methylcyclohexyl |
| I-52 | 4-(morpholin-4-yl)phenyl | (1-(methylsulfonyl)piperidin-4-yl)oxy | 4-methylcyclohexyl |

TABLE 1-continued
| No. | X | Y | Z |
|---|---|---|---|
| I-53 | 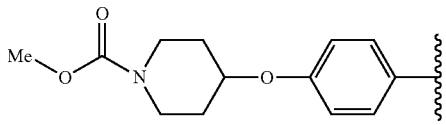 | 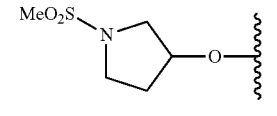 | 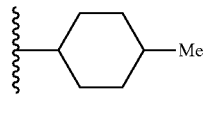 |
| I-54 |  | 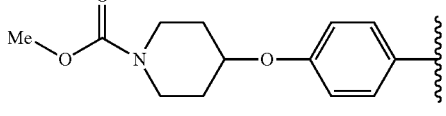 | 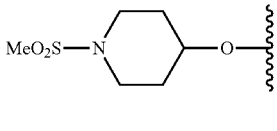 |
| I-55 | 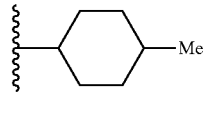 | 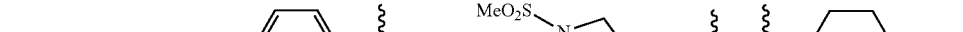 | 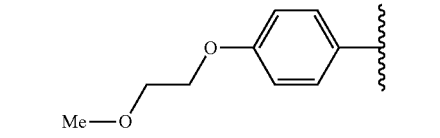 |
| I-56 | 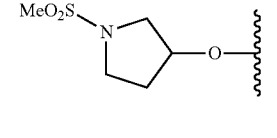 | 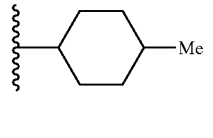 |  |
| I-57 | 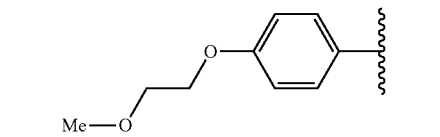 | 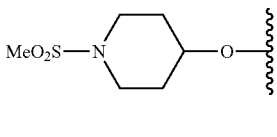 | 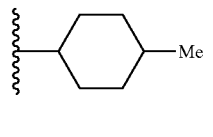 |
| I-58 |  | 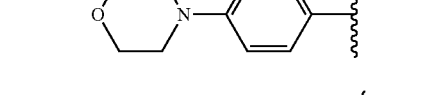 | 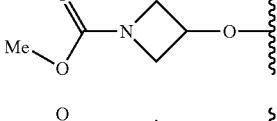 |
| I-59 | 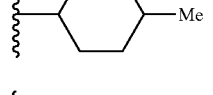 |  | 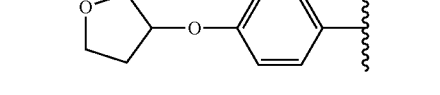 |
| I-60 | 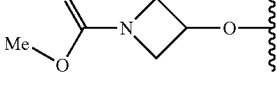 | 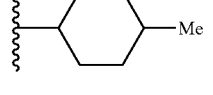 |  |
| I-61 | 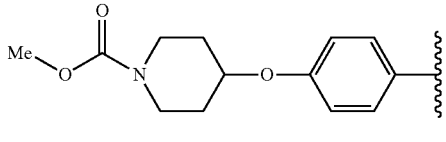 | 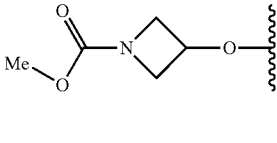 | 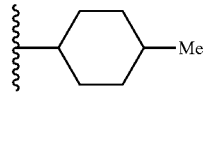 |
| I-62 |  | 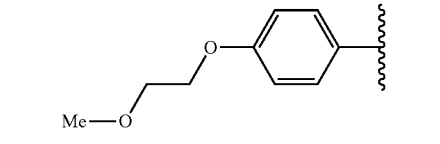 | 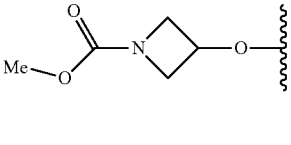 |
| I-63 | 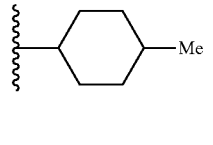 | 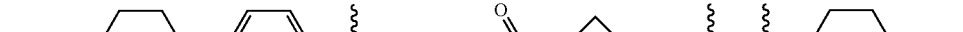 | 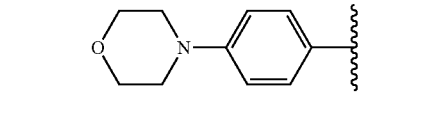 |

TABLE 1-continued

| No. | X | Y | Z |
|---|---|---|---|
| I-64 | Me—O—CH2CH2—O—C6H4— | Me-C(O)-N(azetidine)-O— | 4-methylcyclohexyl |

In certain other embodiments, the compound is N,N-dimethyl-3-(2-((1s,4S)-4-methylcyclohexylamino)-5-(4-morpholinophenyl)pyrimidin-4-yloxy)azetidine-1-sulfonamide; 5-(2,2-dimethyl-2,3-dihydrobenzofuran-5-yl)-N-((1s,4S)-4-methylcyclohexyl)-4-((R)-tetrahydrofuran-3-yloxy)pyrimidin-2-amine; 5-(3-methylbenzo[d]isoxazol-5-yl)-N-((1s,4S)-4-methylcyclohexyl)-4-((R)-tetrahydrofuran-3-yloxy)pyrimidin-2-amine; N,N-dimethyl-3-(4-(2-((1s,4S)-4-methylcyclohexylamino)-4-((R)-tetrahydrofuran-3-yloxy)pyrimidin-5-yl)phenoxy)pyrrolidine-1-carboxamide; N-((1s,4S)-4-methylcyclohexyl)-5-(4-(1-(methylsulfonyl)pyrrolidin-3-yloxy)phenyl)-4-((R)-tetrahydrofuran-3-yloxy)pyrimidin-2-amine; 4-((R)-tetrahydrofuran-3-yloxy)-5-(4-((S)-tetrahydrofuran-3-yloxy)phenyl)-N-(cis-4-methylcyclohexyl)pyrimidin-2-amine; 4-((R)-tetrahydrofuran-3-yloxy)-5-(4-((R)-tetrahydrofuran-3-yloxy)phenyl)-N-(cis-4-methylcyclohexyl)pyrimidin-2-amine; (R)-methyl 3-((2-(cis-4-methylcyclohexylamino)-5-(4-morpholinophenyl)pyrimidin-4-yloxy)methyl)pyrrolidine-1-carboxylate; 4-(((R)-1-methylsulfonylpyrrolidin-3-yl)methoxy)-N-(cis-4-methylcyclohexyl)-5-(4-morpholinophenyl)pyrimidin-2-amine; methyl 3-((2-((1s,4S)-4-methylcyclohexylamino)-5-(4-morpholinophenyl)pyrimidin-4-yloxy)methyl)azetidine-1-carboxylate; 4-((1-methylsulfonyl-azetidin-3-yl)methoxy)-N-(cis-4-methylcyclohexyl)-5-(4-morpholinophenyl)pyrimidin-2-amine; methyl 4-((2-((1s,4S)-4-methylcyclohexylamino)-5-(4-morpholinophenyl)pyrimidin-4-yloxy)methyl)piperidine-1-carboxylate; 4-((1-methylsulfonyl-piperidin-4-yl)methoxy)-N-(cis-4-methylcyclohexyl)-5-(4-morpholinophenyl)pyrimidin-2-amine; 4-((R)-tetrahydrofuran-3-yloxy)-5-(4-(2-methoxyethyl)phenyl)-N-(cis-4-methylcyclohexyl)pyrimidin-2-amine hydrochloride; of 4-((R)-tetrahydrofuran-3-yloxy)-5-(4-(2-methoxyethoxy)phenyl)-N-((1S,4S)-4-methylcyclohexyl)pyrimidin-2-amine; 4-((R)-tetrahydrofuran-3-yloxy)-N-((1S,4S)-4-methylcyclohexyl)-5-(4-(tetrahydro-2H-pyran-4-yloxy)phenyl)pyrimidin-2-amine; N-(cis-4-methylcyclohexyl)-4-(1-(methylsulfonyl)-azetidin-3-yloxy)-5-(4-((R)-tetrahydrofuran-3-yloxy)phenyl)pyrimidin-2-amine; N-(cis-4-methylcyclohexyl)-4-(1-(methylsulfonyl)azetidin-3-yloxy)-5-(4-((S)-tetrahydrofuran-3-yloxy)phenyl)pyrimidin-2-amine; 4-(methoxymethyl)-N-((1s,4s)-4-methylcyclohexyl)-5-(4-morpholinophenyl)-6-(oxetan-3-yloxy)pyrimidin-2-amine; 4-(methoxymethyl)-N-((1s,4s)-4-methylcyclohexyl)-6-(oxetan-3-yloxy)-5-(4-((S)-tetrahydrofuran-3-yloxy)phenyl)pyrimidin-2-amine; 4-methyl-N-((1s,4s)-4-methylcyclohexyl)-6-(oxetan-3-yloxy)-5-(4-((S)-tetrahydrofuran-3-yloxy)phenyl)pyrimidin-2-amine; 2-((1s,4R)-4-methylcyclohexylamino)-5-(4-morpholinophenyl)-6-((S)-tetrahydrofuran-3-yloxy)pyrimidine-4-carboxylic acid; or a pharmaceutically acceptable salt or N-oxide thereof.

In certain other embodiments, the compound is the following:

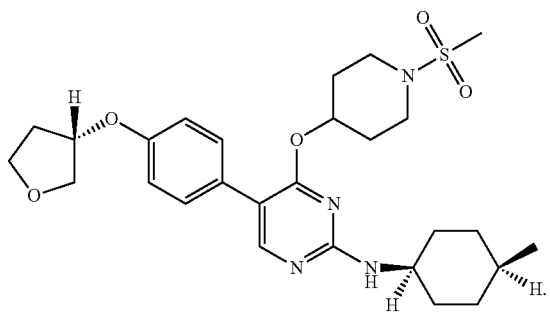

Another aspect of the invention provides a pharmaceutical composition comprising a compound disclosed herein formulated together with one or more pharmaceutically acceptable carriers. These formulations include those suitable for oral, rectal, topical, buccal and parenteral (e.g., subcutaneous, intramuscular, intradermal, or intravenous) administration, although the most suitable form of administration in any given case will depend on the degree and severity of the condition being treated and on the nature of the particular compound being used.

Multiple methods for preparing compounds described herein are provided in the examples. Further synthetic methods for preparing various compounds described herein are provided by the following schemes. The schemes are given for the purpose of illustrating the invention, but not for limiting the scope or spirit of the invention. Starting materials shown in the schemes can be obtained from commercial sources or can be prepared based on procedures described in the literature.

The synthetic route in Scheme 1 illustrates a general method for preparing pyrimidine derivatives. The method involves attaching the desired substituents to the pyrimidine core. The desired —OR' group attached at the 4-position of the pyrimidine core can be installed by reacting bromodichloropyrimidine A with the appropriate alkali metal alkoxide to provide bromo-chloropyrimidine B. The amino group at the 2-position of the pyrimidine ring can be installed by reacting bromo-chloropyrimidine B with the appropriate amino compound (R"—NH$_2$). The identity of the R" group is selected based on the desired R" group in the final pyrimidine product D. The aryl or heteroaryl group at the C5-position can be installed by reacting an aryl or heteroaryl boronic acid with bromo-pyrimidine C under Suzuki coupling conditions to provide final product D.

SCHEME 2

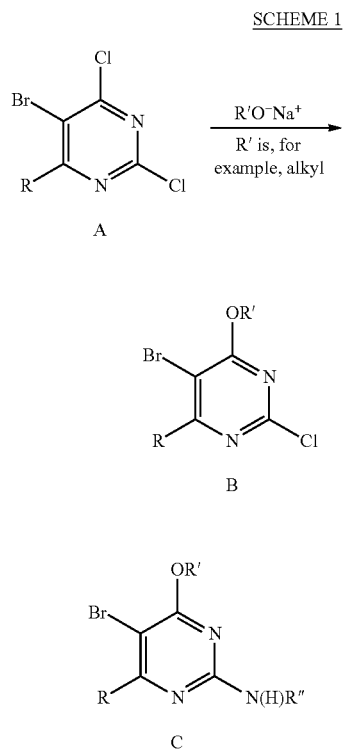

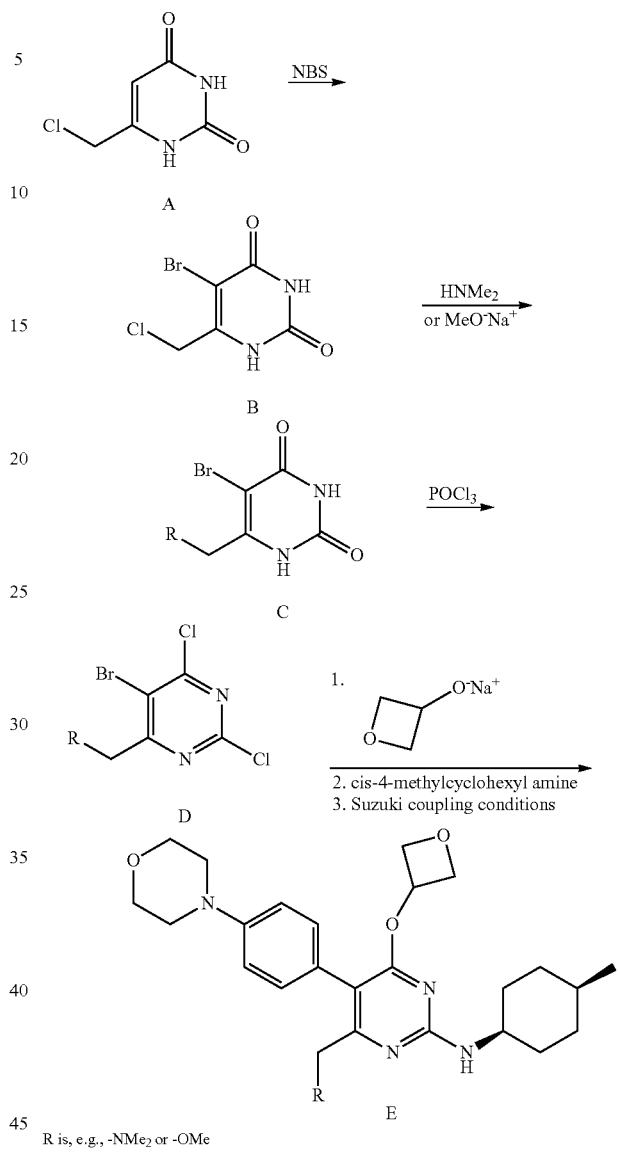

Scheme 2 provides a more detailed exemplary synthetic procedure for making pyrimidine derivatives having various functional groups (e.g., alkylamino or alkylalkoxy) at the C6-position of the pyrimidine ring. Chloro-pyrimidinedione A can be obtained from commercial sources and converted to chloro-bromo-pyrimidinedione B using N-bromo-succinimide (NBS) following procedures described in, for example, Bioorg. & Med. Chem., 2004, 12(13): 3431-3441. Alternatively, compound B can be obtained from commercial sources. The primary chloro group in compound B can be displaced by a variety of nucleophilic groups in order to install different functional groups at this position. For example, reaction of dimethylamine or sodium methoxide with chloro-pyrimidinedione B provides intermediate C. See, for example, Bioorg. & Med. Chem., 2004, 12(13): 3431-3441 for further information on this type of synthetic operation. Reaction of intermediate C with phosphorous oxychloride (POCl₃) provides dichloro-bromo-pyrimidine D. The substituent at the C4-position of the pyrimidine ring can be installed by reacting synthetic intermediate D with a desired alkoxide. The amino group at the C2-position of the pyrimidine ring and the aryl or heteroaryl group at the C5-position of the pyrimidine ring can be installed using procedures describe in Scheme 1 to afford final product E.

Scheme 3 provides a more detailed exemplary synthetic procedure for making pyrimidine derivatives having various functional groups (e.g., carboxylic acid or carboxamide) at the C6-position of the pyrimidine ring. Dioxo-pyrimidine-carbonitrile A can be obtained from commercial sources and converted to bromo-dioxo-pyrimidine-carbonitrile B using N-bromo-succinimide (NBS). Reaction of bromo-dioxo-pyrimidine-carbonitrile B with phosphorous oxychloride (POCl₃) provides dichloro-bromo-pyrimidine C. The substituent at the C-4 position of the pyrimidine ring can be installed by reacting synthetic intermediate C with a desired alkoxide. The amino group at the C2-position of the pyrimidine ring and the aryl or heteroaryl group at the C5-position of the pyrimidine ring can be installed using procedures describe in Scheme 1 to afford cyano-pyrimidine E. The cyano group in cyano-pyrimidine E can be converted to a carboxylic acid group using standard functional group manipulation techniques to provide carboxylic acid F. Finally, the carboxylic group can be converted to various carboximide groups using standard functional group manipulation techniques to provide final compound G. For a description of standard organic chemistry functional group transformation techniques, see, for example, "Comprehensive Organic Synthesis" (B. M. Trost & I. Fleming, eds., 1991-1992).

SCHEME 3

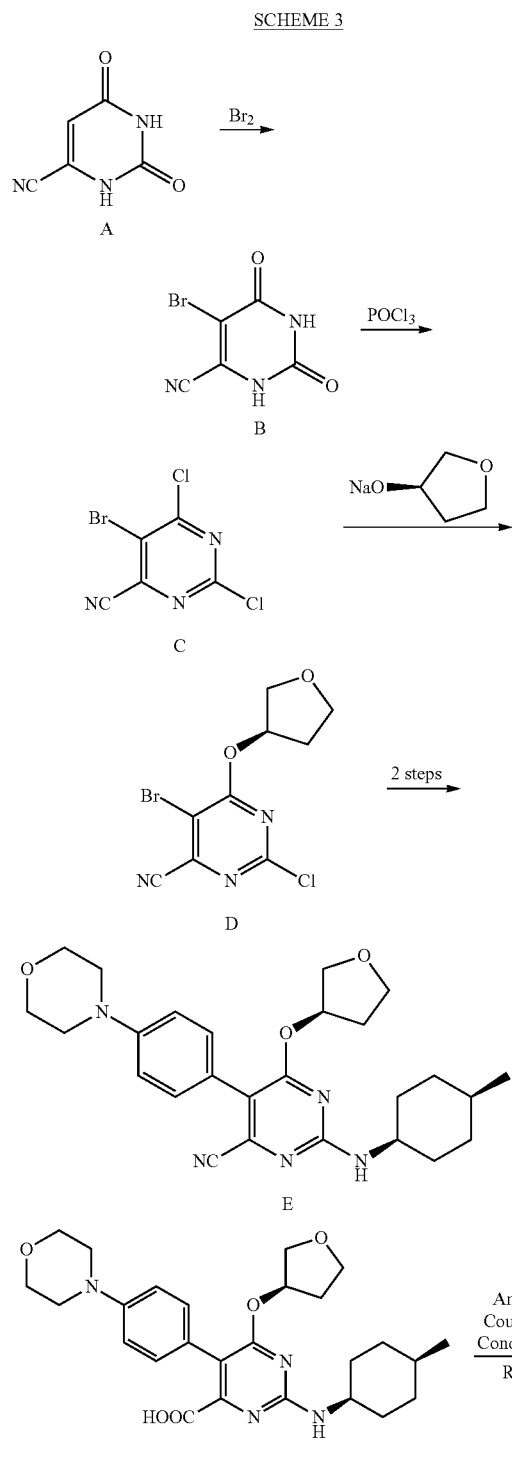

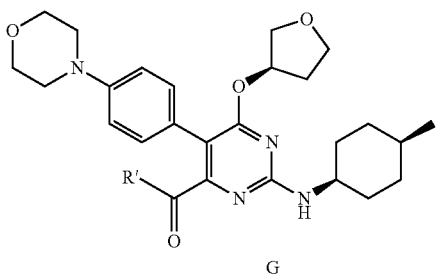

R' is, e.g., -NH₂, -N(Me)₂, or

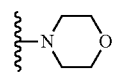

Scheme 4 provides an alternative approach to making pyrimidine derivatives having a carboxamide group at the C6-position of the pyrimidine ring. Carboxylic acid A can be obtained from commercial sources and converted to bromo-dichlorocarboxamide B using a two-step procedure. First, carboxylic acid A is treated with thionyl chloride to provide a dichloro-carboxylic acid intermediate (not shown). This synthetic intermediate is subjected to amide coupling conditions in the presence of an amine compound (HNRR') to provide bromo-dichlorocarboxamide B, which can be converted into the final product in three steps using procedures described in Scheme 1. Exemplary conditions for performing an amide coupling reaction are described in, for example, "Comprehensive Organic Synthesis" (B. M. Trost & I. Fleming, eds., 1991-1992)

SCHEME 4

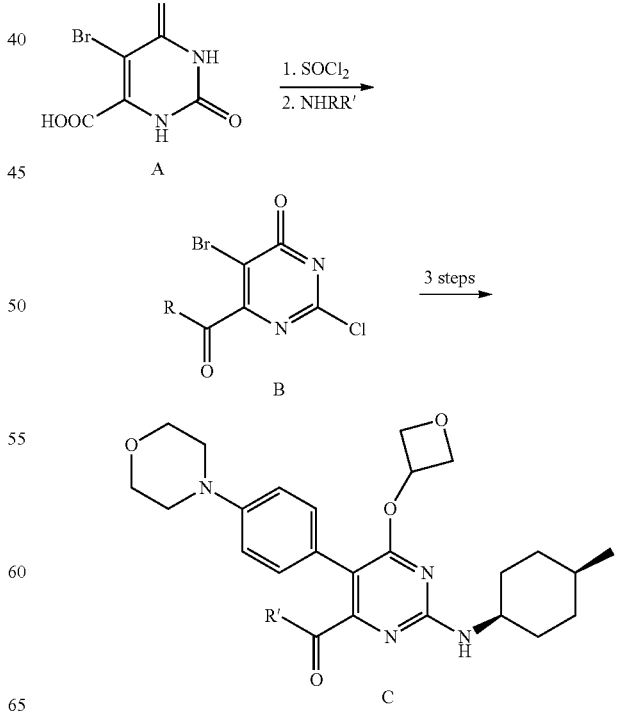

-continued

R' is, e.g., -NH$_2$, -N(Me)$_2$, or

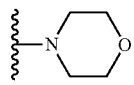

Scheme 5 provides a more detailed exemplary synthetic procedure for making pyrimidine derivatives having an aryl group at the C6-position of the pyrimidine ring. Phenylpyrimidine-dione A can be obtained from commercial sources and converted to bromo-pyrimidine-dione B using bromination conditions described in the literature. See, for example, *J. Med. Chem.*, 1985, 28(12), 1864-1869. Reacting bromo-pyrimidine-dione B with phosphorous oxychloride (POCl$_3$) provides bromo-dichloropyrimidine C, which can be converted to final product D using the procedures described in Scheme 1 for installing the desired substituents at the C2-position, C4-position, and CS-position of the pyrimidine ring.

SCHEME 5

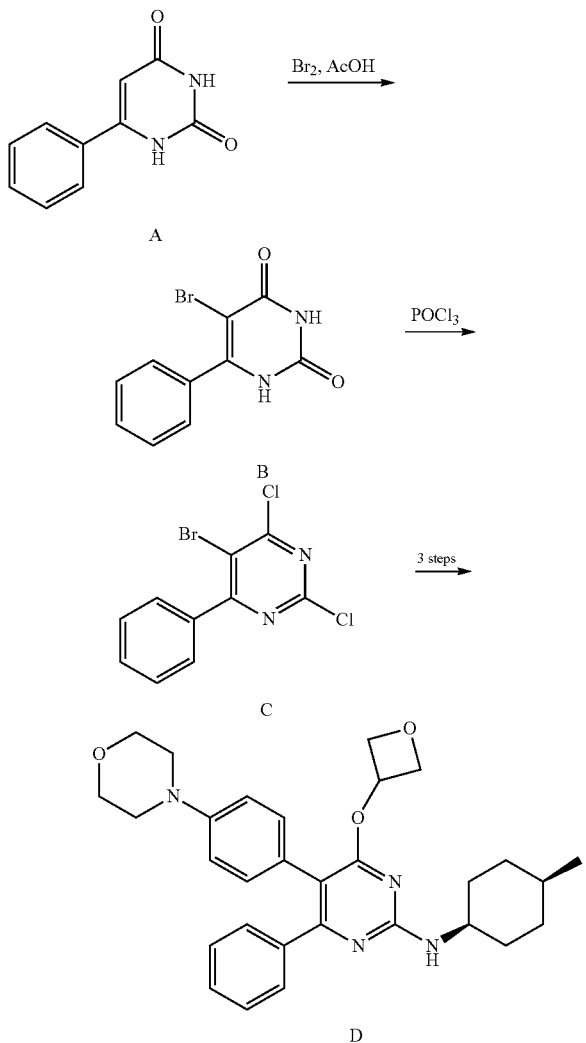

III. THERAPEUTIC APPLICATIONS

The invention further provides methods of modulating the activity of one or more cystic fibrosis transmembrane regulators comprising exposing said receptor to a compound of the invention, e.g., a compound of Formula I, IA, II, IIA, III, or IV, as described herein above. The invention further provides methods of treating a disease associated with expression or activity of one or more cystic fibrosis transmembrane regulators in a patient comprising administering to the patient a therapeutically effective amount of a compound of the invention.

These compounds and pharmaceutically acceptable compositions are useful for treating or lessening the severity of a variety of diseases, disorders, or conditions, including, but not limited to, cystic fibrosis, hereditary emphysema, hereditary hemochromatosis, coagulation-cibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, secretory diarrhea or polycystic kidney disease, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry eye disease, or Sjogren's disease.

One embodiment of the invention provides a method of treating airway inflammation comprising administering to a subject in need thereof a therapeutically effective amount of a compound of the invention, e.g., a compound of Formula I, IA, II, IIA, III, or IV, as described herein above. The methods disclosed herein may involve treating cystic fibrosis.

Another embodiment provides a method of treating cystic fibrosis comprising administering to a subject in need thereof a therapeutically effective amount of a compound described herein, e.g., a compound of Formula I, IA, II, IIA, III, or IV, as described herein above.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Exemplary pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin. Compositions for inhalation or insufflation include solutions and suspensions in pharmaceutically acceptable, aqueous or organic solvents, or mixtures thereof, and powders.

Advantageously, the invention also provides kits for use by a consumer having, or at risk of having, a disease or condition associated with cystic fibrosis transmembrane regulators. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, ... etc. ... Second Week, Monday, Tuesday, ..." etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

EXAMPLES

The compounds of the present invention can be prepared in a number of ways well known to one skilled in the art of organic synthesis. More specifically, compounds of the invention may be prepared using the reactions and techniques described herein. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available (such as through Aldrich Chemicals Co. (Milwaukee, Wis.), Alfa Aesar (Ward Hill, Mass.), Maybridge Chemical Company, Ltd. (Cornwall, England), Ryan Scientific Inc. (Mt. Pleasant, S.C.), Combi-Blocks, Inc. (San Diego, Calif.), and Focus Synthesis LLC (San Diego, Calif.)) or are readily prepared by standard methods from known materials.

Unless specified otherwise, starting materials are generally available from commercial sources. NMR spectra were recorded on a Varian AS 400 (Varian Inc., Palo Alto, Calif.) at room temperature at 400 MHz for proton, or a Bruker Avance 300 UltraShield™ (Bruker BioSpin Corp., Billerica, Mass.) at 300 MHz for proton and at 282 MHz for $^{19}$F. Chemical shifts are expressed in parts per million (δ) relative to residual solvent as an internal reference. The peak shapes are denoted as follows: s, singlet; d, doublet; t, triplet; q, quartet; m, multiplet; bs, broad singlet; bd, broad doublet. Liquid chromatography electrospray ionization mass spectra (LCMS) were obtained on an Agilent HP 1100 instrument (Agilent Technologies, Foster City, Calif.). Where the intensity of chlorine or bromine-containing ions are described, the expected intensity ratio was observed (approximately 3:1 for $^{35}$Cl/$^{37}$Cl-containing ions and 1:1 for $^{79}$Br/$^{81}$Br-containing ions) and the intensity of only the lower mass ion is given. MS peaks are reported for all examples. Microwave reactions were performed on a Biotage Emrys™ Optimizer (Biotage, Charlottesville, Va.).

Column chromatography was performed on a CombiFlash Companion™ (Teledyne ISCO Inc., Lincoln, Nebr.) with different size of RediSep Rf columns. Preparative thin-layer chromatography was performed using Analtech silica gel GF with UV254 indicator (Analtech Inc., Newark, Del.) on 20 cm×20 cm×1 mm plates. When needed, multiple plates are used. After eluting the plates with the indicated solvent, the desired band is marked under UV light, and scraped off. The desired product is extracted from the silica using a polar solvent system (e.g., 20% methanol in methylene chloride or 100% EtOAc). Preparative HPLC was performed on a Varian Dynamax instrument (Varian Inc., Palo Alto, Calif.) using a Kromasil 100-10-C18 250 mm×20 mm column (EKA Chemicals, 80 Bohus, Sweden).

Example 1

Preparation of N,N-dimethyl-3-(2-((1s,4S)-4-methyl-cyclohexylamino)-5-(4-morpholinophenyl)pyrimidin-4-yloxy)azetidine-1-sulfonamide

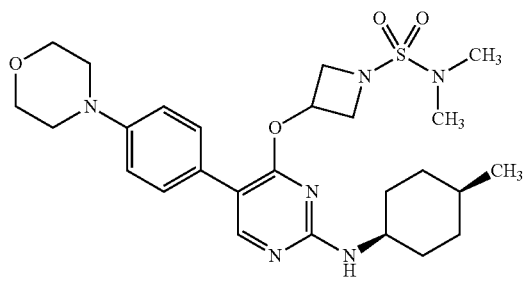

Step 1: Preparation of tert-butyl 3-(5-bromo-2-chloropyrimidin-4-yloxy)azetidine-1-carboxylate (1)

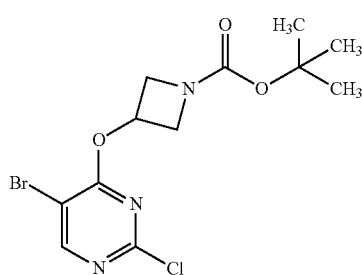

(1)

To a solution of 3-hydroxyazetidine-1-carboxylic acid tert-butyl ester (2.5 g, 14.43 mmol) in anhydrous THF (65 mL) was added NaH (55 w/w % in mineral oil, 381 mg, 15.9 mmol) under $N_2$ atmosphere at 0 to 5° C. The mixture was allowed to warm to room temperature and stirred for 2 hr. Then, this reaction mixture was cooled to −5 to 0° C., and was added slowly to a solution of 5-bromo-2,4-dichloropyrimidine (3.28 g, 14.43 mmol) in anhydrous THF (28 mL) at −5 to 0° C. The mixture was stirred at −5 to 0° C. for 2 hr, then allowed to warm to room temperature and stirred for additional 6 h. After this time, the mixture was quenched with water (75 mL) at 0° C. The phases were separated and the aqueous phase was extracted with ethyl acetate (3×50 mL). The organic layers were combined, dried over anhydrous magnesium sulfate and the solvent was removed under reduced pressure. The residue was purified by column chromatography (silica gel; eluting with 10% ethyl acetate in hexane) to give the title compound (1) (3.35 g, 64%) as a white solid. $^1$H NMR (CDCl$_3$, 400 MHz) δ 8.48 (s, 1H), 5.38-5.46 (m, 1H), 4.38 (dd, J=10.3, 6.5 Hz, 2H), 4.06 (dd, J=10.4, 4.1 Hz, 2H), 1.46 (s, 9H); MS (APCI, M+H$^+$) $C_{12}H_{16}BrClN_3O_3$, calcd. 364.0. found 307.9 (M+1-t-butyl), 309.9 (M+3-t-butyl)

Step 2: Preparation of tert-butyl 3-(5-bromo-2-((1s,4S)-4-methylcyclohexylamino)-pyrimidin-4-yloxy)azetidine-1-carboxylate (2)

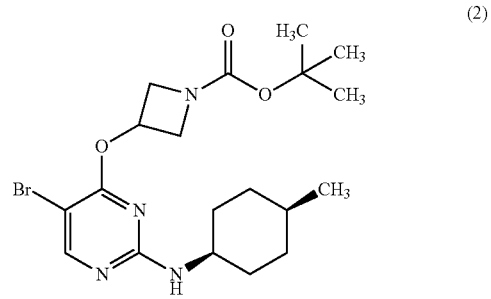

To a solution of tert-butyl 3-(5-bromo-2-chloropyrimidin-4-yloxy)azetidine-1-carboxylate (1) (2.00 g, 5.50 mmol) in 15 mL of EtOH was added cis-4-methylcyclohexylamine hydrochloride (1.23 g, 8.23 mmol) followed by triethylamine (1.66 g, 2.28 mL, 16.4 mmol). The mixture was heated in a microwave reactor at 130° C. for 2 h. After cooling to room temperature, the reaction mixture was diluted with CH$_2$Cl$_2$ (15 mL) and 20 mL of H$_2$O. The organic layer was separated, dried over anhydrous magnesium sulfate and concentrated under reduced pressure. The residue was purified by column chromatography (silica gel; eluting with 10% ethyl acetate in hexane) to give the title compound (2) (1.57 g, 65%) as an off-white solid. $^1$H NMR (CDCl$_3$, 400 MHz) δ 8.10 (s, 1H), 5.2-5.33 (m, 1H), 5.16 (bs, 1H), 4.29 (dd, J=10.2, 6.9 Hz, 2H), 4.05 (dd, J=10.0, 4.5 Hz, 2H), 3.91 (bs, 1H), 1.68-1.82 (m, 2H), 1.53-1.70 (m, 4H), 1.46 (s, 9H), 1.10-1.34 (m, 3H), 0.93 (d, J=6.5 Hz, 3H); MS (APCI, M+H$^+$) $C_{19}H_{30}BrN_4O_3$, calcd. 441.1. found 441.2, 443.2.

Step 3: Preparation of tert-butyl 3-(2-((1s,4S)-4-methylcyclohexylamino)-5-(4-morpholinophenyl)pyrimidin-4-yloxy)azetidine-1-carboxylate (3)

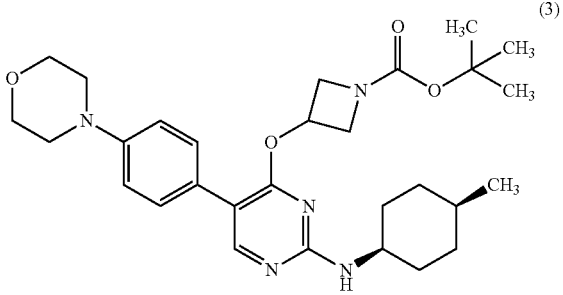

To a solution of tert-butyl 3-(5-bromo-2-((1s,4S)-4-methylcyclohexylamino)-pyrimidin-4-yloxy)azetidine-1-carboxylate (2) (420 mg, 0.95 mmol) in CH$_3$CN (16 mL) was added 4-(morpholino)phenylboronic acid (394 mg, 1.90 mmol) followed by Pd(PPh$_3$)$_4$ (110 mg, 0.1 mmol) and aqueous 2M Na$_2$CO$_3$ (8 mL). The mixture was heated in a microwave reactor at 100° C. for 30 minutes. After cooling to room temperature, the reaction mixture was diluted with EtOAc and washed with H₂O. The organic layer was separated, dried over anhydrous magnesium sulfate and concentrated under reduced pressure. The residue was purified by column chromatography (silica gel, eluting with 30% ethyl acetate in hexane) to give the title compound (3) (262 mg, 53%) as a light yellow solid. $^1$H NMR (CDCl$_3$, 400 MHz) δ 8.11 (s, 1H), 7.41 (d, J=8.8 Hz, 2H), 6.95 (d, J=8.8 Hz, 2H), 5.27-5.37 (m, 1H), 5.15 (bs, 1H), 4.29 (dd, J=9.8, 6.8 Hz, 2H), 4.01 (dd, J=9.9, 4.4 Hz, 3H), 3.83-3.91 (m, 4H), 3.13-3.26 (m, 4H), 1.72-1.87 (m, 2H), 1.56-1.72 (m, 4H), 1.45 (s, 9H), 1.14-1.34 (m, 3H), 0.94 (d, J=6.3 Hz, 3H); MS (APCI, M+H$^+$) C$_{29}$H$_{42}$N$_5$O$_4$, calcd. 524.3. found 524.4.

Step 4: Preparation of 4-(azetidin-3-yloxy)-N-((1s, 4S)-4-methylcyclohexyl)-5-(4-morpholinophenyl) pyrimidin-2-amine (4)

(4)

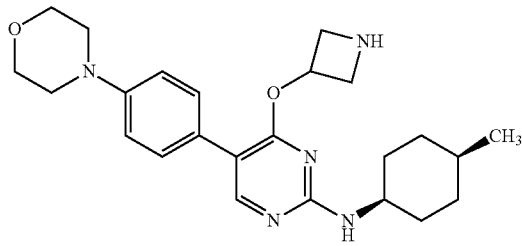

tert-Butyl 3-(2-((1s,4S)-4-methylcyclohexylamino)-5-(4-morpholinophenyl)-pyrimidin-4-yloxy)azetidine-1-carboxylate (3) (775 mg, 1.48 mmol) was dissolved in 5 mL of 1,4-dioxane saturated with HCl gas. The reaction mixture was stirred at room temperature for 2 h. After this time, the solvent was removed under reduced pressure, the residue treated with 5 mL of 20 w/w % aqueous NaHCO$_3$ and the mixture then extracted with 2×5 mL of CHCl$_3$. The combined organic phases were dried over MgSO$_4$, the drying agent was filtered off and the solvent was evaporated under reduced pressure to give the title compound (4) (550 mg, 87%) as an off-white solid. $^1$H NMR (CDCl$_3$, 400 MHz) δ 8.09 (s, 1H), 7.43 (d, J=8.5 Hz, 2H), 6.94 (d, J=8.5 Hz, 2H), 5.49 (qd, J=6.4 Hz, 1H), 5.10 (bs, 1H), 3.97-4.09 (m, 1H), 3.83-3.96 (m, 6H), 3.80 (dd, J=9.4, 6.4 Hz, 2H), 3.12-3.27 (m, 4H), 1.58-1.90 (m, 8H), 1.16-1.33 (m, 2H), 0.94 (d, J=6.3 Hz, 3H); MS (APCI, M+H$^+$) C$_{24}$H$_{34}$N$_5$O$_2$, calcd. 424.2. found 424.1.

Step 5: Preparation of N,N-dimethyl-3-(2-((1s,4S)-4-methylcyclohexylamino)-5-(4-morpholinophenyl) pyrimidin-4-yloxy)azetidine-1-sulfonamide (5)

(5)

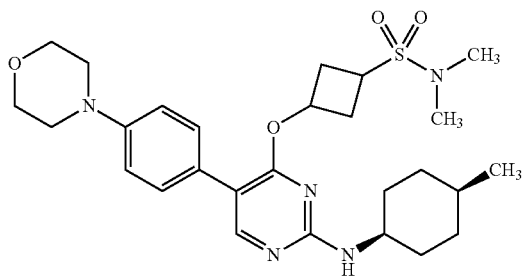

To a mixture of 4-(azetidin-3-yloxy)-N-((1s,4S)-4-methylcyclohexyl)-5-(4-morpholino-phenyl)pyrimidin-2-amine (4) (90 mg, 0.21 mmol), and Na$_2$CO$_3$ (27 mg, 0.25 mmol) in CH$_2$Cl$_2$ (5 mL) was added dropwise N,N-dimethylsulfamoyl chloride (76 mg, 0.53 mmol) at room temperature. The reaction mixture was stirred at room temperature for 30 min. After this time, 5 mL of H$_2$O was added, the organic layer was separated and the aqueous phase was extracted with CH$_2$Cl$_2$ (2×5 mL). The organic extracts were combined, dried over anhydrous magnesium sulfate and concentrated under reduced pressure. The residue was purified by preparative layer chromatography (silica gel, eluting with 5% ethanol in methylene chloride) to give the title compound (5) (18 mg, 16%) as a light yellow solid. $^1$H NMR (CDCl$_3$, 400 MHz) δ 8.11 (s, 1H), 7.40 (d, J=8.8 Hz, 2H), 6.95 (d, J=8.8 Hz, 2H), 5.33 (bs, 1H), 5.25 (bs, 1H), 4.18-4.25 (m, 2H), 4.07 (dd, J=9.3, 5.3 Hz, 2H), 4.00 (bs, 1H), 3.83-3.92 (m, 4H), 3.15-3.26 (m, 4H), 2.82 (s, 6H), 1.73-1.87 (m, 2H), 1.55-1.72 (m, 5H), 1.16-1.33 (m, 2H), 0.95 (d, J=6.5 Hz, 3H); MS (APCI, M+H$^+$) C$_{26}$H$_{39}$N$_6$O$_4$S, calcd. 531.2. found 531.3.

Example 2

Preparation of 5-(2,2-dimethyl-2,3-dihydrobenzofuran-5-yl)-N-((1s,4S)-4-methylcyclohexyl)-4-((R)-tetrahydrofuran-3-yloxy)pyrimidin-2-amine

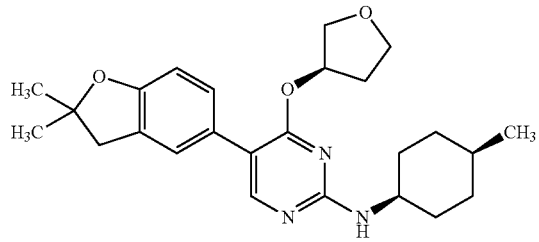

Step 1: Preparation of 1-bromo-4-(2-methylallyloxy)benzene (6)

(6)

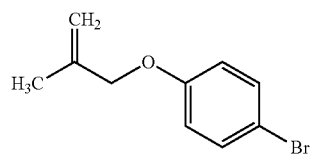

To a solution of 4-bromo phenol (7.0 g, 40.40 mmol) in acetone (165 mL) was added K$_2$CO$_3$ (27.8 g, 202 mmol) followed by 3-bromo-2-methylprop-1-ene (4.9 mL, 44.5 mmol). The mixture was stirred at reflux temperature for 16 h. After cooling to room temperature, the reaction mixture was diluted with CH$_2$Cl$_2$ (200 mL), washed with H$_2$O (2×50 mL) and brine (50 mL). The organic phase was dried over anhydrous sodium sulfate and concentrated under reduced pressure to afford the title compound (6) (8.0 g, 93%) as a colorless liquid. $^1$H NMR (CDCl$_3$, 400 MHz) δ 7.37 (d, J=9.2 Hz, 2H), 6.81 (d, J=9.2 Hz, 2H), 5.08 (s, 1H), 5.00 (s, 1H), 4.41 (s, 2H), 1.83 (s, 3H); MS (ESI, M+H$^+$) C$_{10}$H$_{12}$BrO, calcd. 227.1. found 227.0, 229.0.

Step 2: Preparation of 4-bromo-2-(2-methylallyl)phenol (7)

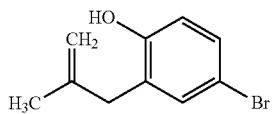

(7)

A solution of 1-bromo-4-(2-methylallyloxy)benzene (6) (1.0 g, 4.4 mmol) in DMF (8 mL) was heated in a microwave reactor at 190° C. for 2 h. After cooling to room temperature, the reaction mixture was diluted with methyl tert-butyl ether (50 mL), and washed with $H_2O$ (25 mL), brine (25 mL), dried over anhydrous sodium sulfate and concentrated under reduced pressure. The residue was purified by flash chromatography (silica gel, eluting with 5% ethyl acetate in hexanes) to give the title compound (7) (0.7 g, 65%) as a liquid. $^1$H NMR (CDCl$_3$, 400 MHz) δ 7.27-7.25 (m, 2H), 6.72 (d, J=8.4 Hz, 1H), 4.95 (s, 1H), 4.86 (s, 1H), 3.34 (s, 2H), 1.74 (s, 3H); MS (ESI, M+H$^+$) $C_{10}H_{12}BrO$, calcd. 227.1. found 227.0, 229.0.

Step 3: Preparation of 5-bromo-2,2-dimethyl-2,3-dihydrobenzofuran (8)

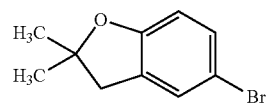

(8)

To a solution of 4-bromo-2-(2-methylallyl)phenol (7) (4.5 g, 19.8 mmol) in $CH_2Cl_2$ (250 mL) was added iodine (1.3 g, 4.95 mmol) and the mixture stirred at room temperature for 48 h. The mixture was then diluted with methyl tert-butyl ether (100 mL) and washed with $H_2O$ (50 mL), brine (50 mL), dried over anhydrous sodium sulfate and concentrated under reduced pressure. The residue was purified by flash chromatography (silica gel, eluting with 5% ethyl acetate in hexanes) to give the title compound (8) (4.0 g, 88%) as yellow liquid. $^1$H NMR (CDCl$_3$, 400 MHz) δ 7.24 (s, 1H), 7.20 (d, J=8.4 Hz, 1H), 6.61 (d, J=8.4 Hz, 1H), 3.00 (s, 2H), 1.47 (s, 6H); MS (ESI, M+H$^+$) $C_{10}H_{12}BrO$, calcd. 227.1. found 227.0, 229.0.

Step 4: Preparation of 2-(2,2-dimethyl-2,3-dihydrobenzofuran-5-yl)-4,4,5,5-tetramethyl-1,3,2-dioxaborolane (9)

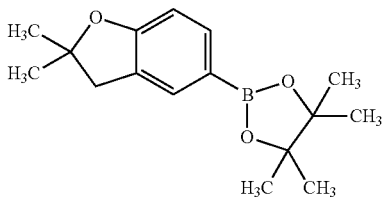

(9)

To a solution of 5-bromo-2,2-dimethyl-2,3-dihydrobenzofuran (8) (4.0 g, 17.61 mmol) in 1,4-dioxane (40 mL) was added KOAc (6.0 g, 61.63 mmol) and bis(pinacolato)diboron (4.7 g, 18.49 mmol) followed by Pd(dppf)Cl$_2$.CH$_2$Cl$_2$ (1.4 g, 1.76 mmol). The mixture was purged with argon for 10 min and then heated at reflux temperature for 16 h. After this time, the mixture was cooled, filtered through a pad of celite and the filtrate was partitioned between methyl tert-butyl ether (100 mL) and water (25 mL). The organic phase was separated, washed with brine (25 mL), dried over anhydrous sodium sulfate, filtered and concentrated under reduced pressure. The residue was purified by flash chromatography (silica gel, eluting with 5% ethyl acetate in hexanes) to afford the title compound (9) (1.0 g, 21%) as a white solid. $^1$H NMR (CDCl$_3$, 400 MHz) δ 7.62-7.60 (m, 2H), 6.74 (d, J=8.4 Hz, 1H), 3.00 (s, 2H), 1.47 (s, 6H), 1.33 (s, 12H); MS (ESI, M+H$^+$) $C_{16}H_{24}BO_3$, calcd. 275.2. found 275.0.

Step 5: Preparation of 5-(2,2-dimethyl-2,3-dihydrobenzofuran-5-yl)-N-((1s,4S)-4-methylcyclohexyl)-4-((R)-tetrahydrofuran-3-yloxy)pyrimidin-2-amine (10)

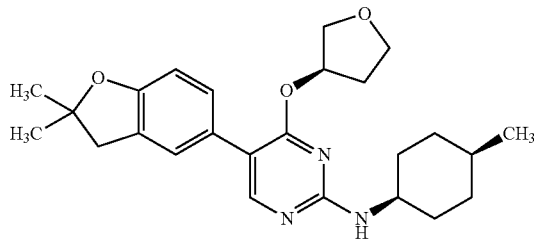

(10)

To a solution of 5-bromo-N-((1s,4S)-4-methylcyclohexyl)-4-((R)-tetrahydrofuran-3-yloxy)pyrimidin-2-amine (100 mg, 0.28 mmol) in CH$_3$CN (3 mL) was added 2-(2,2-dimethyl-2,3-dihydrobenzofuran-5-yl)-4,4,5,5-tetramethyl-1,3,2-dioxaborolane (9) (154 mg, 0.56 mmol) followed by Pd(PPh$_3$)$_4$ (32 mg, 28 μmol) and aqueous 2M Na$_2$CO$_3$ (2.0 mL). The mixture was heated in a microwave reactor at 100° C. for 30 minutes. After cooling to room temperature, the reaction mixture was diluted with EtOAc and washed with H$_2$O. The organic layer was separated, dried (MgSO$_4$) and concentrated under reduced pressure. The residue was purified by preparative HPLC to give the title compound (10) (38.2 mg, 32%) as a light brown solid. $^1$H NMR (CDCl$_3$, 400 MHz) δ 8.05 (s, 1H), 7.16-7.24 (m, 2H), 6.73 (d, J=8.0 Hz, 1H), 5.53-5.62 (m, 1H), 5.19 (bs, 1H), 4.01-4.13 (m, 2H), 3.83-3.97 (m, 3H), 3.04 (s, 2H), 2.19-2.30 (m, 1H), 2.09-2.19 (m, 1H), 1.74-1.88 (m, 2H), 1.57-1.72 (m, 5H), 1.50 (s, 6H), 1.18-1.34 (m, 2H), 0.95 (d, J=6.3 Hz, 3H); MS (APCI, M+H$^+$) $C_{25}H_{34}N_3O_3$, calcd. 424.3. found 424.3.

Example 3

Preparation of 5-(3-methylbenzo[d]isoxazol-5-yl)-N-((1s,4S)-4-methylcyclohexyl)-4-((R)-tetrahydrofuran-3-yloxy)pyrimidin-2-amine

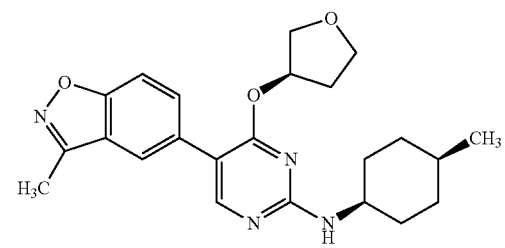

Step 1: Preparation of (E)-1-(5-bromo-2-hydroxyphenyl)ethanone oxime (11)

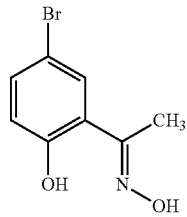

To a solution of 1-(5-bromo-2-hydroxyphenyl)ethanone (2.0 g, 9.30 mmol) in ethanol (20 mL) were added hydroxylamine hydrochloride (0.7 g, 10.2 mmol) and potassium acetate (1.0 g, 10.2 mmol). The mixture was stirred at reflux temperature for 16 h. After this time, the mixture was cooled, concentrated and the residue was diluted with $CH_2Cl_2$ (25 mL) and washed with $H_2O$ (25 mL). The organic layer was dried over anhydrous sodium sulfate and concentrated under reduced pressure to afford title compound (11) (2.1 g, 95%) as a white solid. $^1$H NMR ($CDCl_3$, 400 MHz) δ 7.40 (s, 1H), 7.20 (dd, J=8.8, 2.0 Hz, 1H), 6.72 (d, J=8.8 Hz, 1H), 2.50 (bs, 1H), 2.20 (s, 3H); MS (ESI, M+H$^+$) $C_8H_9BrNO_2$, calcd. 230.0. found 230.0, 232.0.

Step 2: Preparation of 5-bromo-3-methylbenzo[d]isoxazole (12)

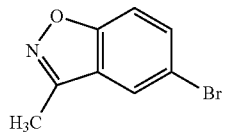

To a stirred solution of triphenylphosphine (6.8 g, 26.1 mmol) and 2,3-dichloro-5,6-dicyanobenzoquinone (DDQ) (3.9 g, 26.1 mmol) in $CH_2Cl_2$ (50 mL) was added (E)-1-(5-bromo-2-hydroxyphenyl)ethanone oxime (11) (5.0 g, 21.73 mmol) in small portions over a period of 15 min. The mixture was stirred for additional 10 min at room temperature and then the solvent was removed under reduced pressure. The residue was purified by flash column chromatography (silica gel, eluting with 5% ethyl acetate and hexanes) to give the title compound (12) (3.0 g, 65%) as a brown solid. $^1$H NMR ($CDCl_3$, 400 MHz) δ 7.79 (s, 1H), 7.40 (dd, J=8.4, 1.6 Hz, 1H), 7.35 (d, J=8.4 Hz, 1H), 2.64 (s, 3H); MS (ESI, M+H$^+$) $C_8H_7BrNO$, calcd. 212.0. found 212.0, 214.0.

Step 3: Preparation of 3-methyl-5-(4,4,5,5-tetramethyl-1,3,2-dioxaborolan-2-yl)benzo[d]isoxazole (13)

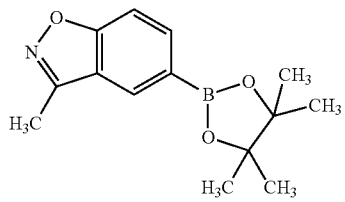

To a solution of 5-bromo-3-methylbenzo[d]isoxazole (12) (3.0 g, 14.14 mmol) in 1,4-dioxane (30 mL) were added KOAc (4.8 g, 49.40 mmol) and bis(pinacolato)diboron (3.7 g, 14.84 mmol) followed by Pd(dppf)Cl$_2$ (1.1 g, 1.41 mmol). The mixture was purged with argon for 10 min and then stirred at reflux temperature for 2 h. After this time, the mixture was cooled, filtered through a pad of celite and the filtrate was partitioned between methyl tert-butyl ether (100 mL) and $H_2O$ (25 mL). The organic phase was separated and washed with brine (25 mL), dried over anhydrous sodium sulfate and concentrated under reduced pressure. The residue was purified by flash chromatography (silica gel, eluting with 5% ethyl acetate in hexanes) to yield the title compound (13) (1.4 g, 38%) as a white solid. $^1$H NMR ($CDCl_3$, 400 MHz) δ 8.09 (s, 1H), 7.76 (d, J=8.4 Hz, 1H), 7.46 (d, J=8.4 Hz, 1H), 2.65 (s, 3H), 1.37 (s, 12H); MS (ESI, M+H$^+$) $C_{14}H_{19}BNO_3$, calcd. 260.1. found 259.9.

Step 4: Preparation of 5-(3-methylbenzo[d]isoxazol-5-yl)-N-((1s,4S)-4-methyl-cyclohexyl)-4-((R)-tetrahydrofuran-3-yloxy)pyrimidin-2-amine (14)

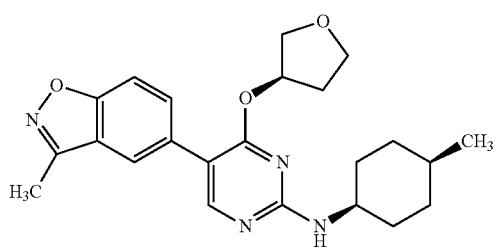

To a solution of 5-bromo-N-((1s,4S)-4-methylcyclohexyl)-4-((R)-tetrahydrofuran-3-yloxy)pyrimidin-2-amine (100 mg, 0.28 mmol) in $CH_3CN$ (3 mL) was added 3-methyl-5-(4,4,5,5-tetramethyl-1,3,2-dioxaborolan-2-yl)benzo[d]isoxazole (13) (145 mg, 0.56 mmol) followed by Pd(PPh$_3$)$_4$ (32 mg, 28 mmol) and aqueous 2M Na$_2$CO$_3$ (2.0 mL). The mixture was heated in a microwave reactor at 100° C. for 30 minutes. After cooling to room temperature, the mixture was diluted with EtOAc and washed with H$_2$O. The organic layer was separated, dried (MgSO$_4$) and concentrated under reduced pressure. The residue was purified by preparative HPLC to give the title compound (14) (44 mg, 39%) as an off-white solid. $^1$H NMR (CDCl$_3$, 400 MHz) δ 8.12 (s, 1H), 7.73 (s, 1H), 7.46 (d, J=8.5 Hz, 1H), 7.37 (dd, J=8.5, 1.5 Hz, 1H), 5.55-5.66 (m, 1H), 5.23 (bs, 1H), 4.02-4.16 (m, 2H), 3.82-3.95 (m, 3H), 2.65 (s, 3H), 2.19-2.29 (m, 2H), 2.09-2.19 (m, 1H), 1.75-1.90 (m, 2H), 1.55-1.74 (m, 5H), 1.17-1.35 (m, 2H), 0.95 (d, J=6.3 Hz, 2H); MS (APCI, M+H$^+$) $C_{23}H_{29}N_4O_3$, calcd. 409.2. found 409.3.

Example 4

Preparation of N,N-dimethyl-3-(4-(2-((1s,4S)-4-methylcyclohexylamino)-4-((R)-tetrahydrofuran-3-yloxy)pyrimidin-5-yl)phenoxy)pyrrolidine-1-carboxamide

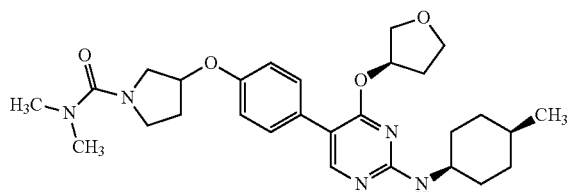

Step 1: Preparation of tert-butyl 3-(tosyloxy)pyrrolidine-1-carboxylate (15)

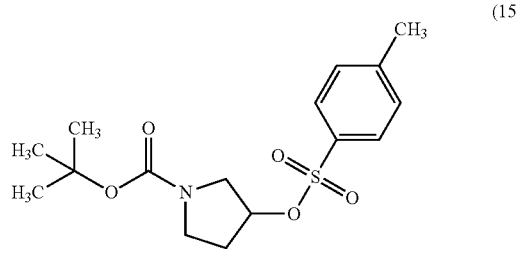

(15)

To a solution of tert-butyl 3-hydroxypyrrolidine-1-carboxylate (0.9 g, 5.02 mmol) in anhydrous pyridine (10 mL) at 0° C. was added 4-methylbenzene-1-sulfonyl chloride (1.0 g, 5.27 mmol). The suspension was allowed to warm to room temperature and stirred for 24 h. After this time, the suspension was poured onto crushed ice and extracted with EtOAc. The organic layer was separated, washed with water, brine, dried (MgSO$_4$) and concentrated under reduced pressure to give the title compound (15) (1.1 g, 69%) as a light yellow colored solid. $^1$H NMR (CDCl$_3$, 400 MHz) δ 7.79 (d, J=8.3 Hz, 2H), 7.35 (d, J=8.0 Hz, 2H), 4.94-5.17 (m, 1H), 3.33-3.56 (m, 4H), 2.46 (s, 3H), 1.79-2.28 (m, 2H), 1.43 (s, 9H); MS (APCI, M+H$^+$) C$_{16}$H$_{24}$NO$_5$S, calcd. 342.1. found 286.1.

Step 2: Preparation of 4-(2-((1s,4S)-4-methylcyclohexylamino)-4-((R)-tetrahydrofuran-3-yloxy)pyrimidin-5-yl)phenol (16)

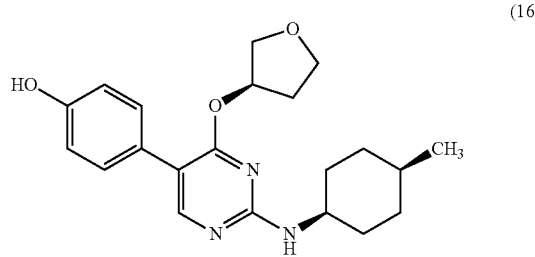

(16)

To a solution of 5-bromo-N-((1s,4S)-4-methylcyclohexyl)-4-((R)-tetrahydrofuran-3-yloxy)pyrimidin-2-amine (700 mg, 1.96 mmol) in CH$_3$CN (28 mL) was added 4-hydroxyphenylboronic acid (542 mg, 3.93 mmol) followed by Pd(PPh$_3$)$_4$ (113 mg, 98 μmol) and aqueous 2M Na$_2$CO$_3$ (14 mL). The mixture was heated in a microwave reactor at 100° C. for 30 minutes. After cooling to room temperature, the reaction mixture was diluted with EtOAc and washed with H$_2$O. The organic layer was separated, dried (MgSO$_4$) and concentrated under reduced pressure. The residue was purified by column chromatography (silica gel, eluting with 30% ethyl acetate in hexane) to give the title compound (16) (602 mg, 83%) as a white solid. $^1$H NMR (CDCl$_3$, 400 MHz) δ 8.07 (s, 1H), 7.33 (d, J=8.8 Hz, 2H), 6.85 (d, J=8.8 Hz, 2H), 5.56-5.62 (m, 1H), 5.66 (bs, 1H), 5.20 (bs, 1H), 4.08 (dd, J=10.1, 5.2 Hz, 1H), 3.99-4.12 (m, 1H), 3.85-3.98 (m, 3H), 2.09-2.29 (m, 2H), 1.75-1.87 (m, 2H), 1.56-1.71 (m, 5H), 1.17-1.32 (m, 2H), 0.94 (d, J=6.5 Hz, 3H); MS (APCI, M+H$^+$) C$_{21}$H$_{28}$N$_3$O$_3$, calcd. 370.2. found 370.2.

Step 3: Preparation of tert-butyl 3-(4-(2-((1s,4S)-4-methylcyclohexylamino)-4-((R)-tetrahydrofuran-3-yloxy)pyrimidin-5-yl)phenoxy)pyrrolidine-1-carboxylate (17)

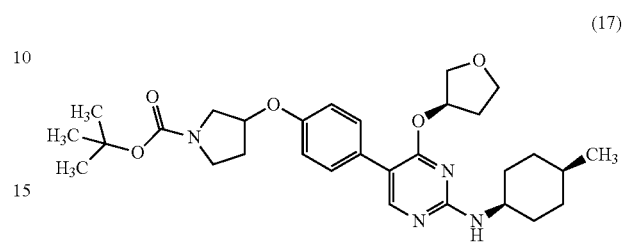

(17)

To a solution of 4-(2-((1s,4S)-4-methylcyclohexylamino)-4-((R)-tetrahydrofuran-3-yloxy)pyrimidin-5-yl)phenol (16) (100 mg, 0.27 mmol) in anhydrous CH$_3$CN (2 mL) was added potassium carbonate (45 mg, 0.33 mmol) followed by tert-butyl 3-(tosyloxy)pyrrolidine-1-carboxylate (15) (111 mg, 0.32 mmol). The resulting mixture was stirred at reflux temperature for 62 h. After this time, the suspension was cooled, poured into cold water and extracted with EtOAc. The organic layer was separated, dried (MgSO$_4$) and concentrated under reduced pressure. The residue was purified by preparative HPLC to give the title compound (17) (86 mg, 59%) as a white solid. $^1$H NMR (CDCl$_3$, 400 MHz) δ 8.07 (s, 1H), 7.38 (bs, 2H), 6.88 (d, J=8.8 Hz, 2H), 5.59 (bs, 1H), 5.19 (bs, 1H), 4.90 (bs, 1H), 4.08 (dd, J=10.1, 5.1 Hz, 1H), 4.02-4.12 (m, 1H), 3.83-3.96 (m, 3H), 3.45-3.72 (m, 4H), 2.02-2.29 (m, 4H), 1.76-1.89 (m, 2H), 1.54-1.72 (m, 5H), 1.47 (s, 9H), 1.18-1.34 (m, 2H), 0.95 (d, J=6.3 Hz, 3H); MS (APCI, M+H$^+$) C$_{30}$H$_{43}$N$_4$O$_5$, calcd. 539.3. found 539.4.

Step 4: Preparation of N-((1s,4S)-4-methylcyclohexyl)-5-(4-(pyrrolidin-3-yloxy)phenyl)-4-((R)-tetrahydrofuran-3-yloxy)pyrimidin-2-amine (18)

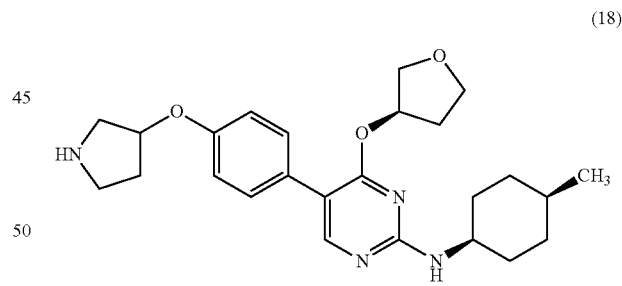

(18)

To a solution of tert-butyl 3-(4-(2-((1s,4S)-4-methylcyclohexylamino)-4-((R)-tetrahydrofuran-3-yloxy)pyrimidin-5-yl)phenoxy)pyrrolidine-1-carboxylate (17) (207 mg, 0.38 mmol) in anhydrous dichloromethane (1 mL) was added trifluoroacetic acid (TFA) (1 mL). The resulting mixture was stirred for 1 h at room temperature. After this time, the mixture was concentrated under reduced pressure. The residue was dissolved in dichloromethane and washed with saturated aqueous NaHCO$_3$. The organic extract was concentrated under reduced pressure. The residue was purified by preparative HPLC and then again by preparative layer chromatography (silica gel, eluting with 17% methanol in chloroform) to give the title compound (18) (148 mg, 88%) as a light brown solid. $^1$H NMR (CDCl$_3$, 400 MHz) δ 8.08 (s, 1H), 7.38 (d, J=8.5 Hz, 2H), 6.88 (d, J=8.5 Hz, 2H), 5.54-5.64 (m, 1H), 5.08-5.22 (m, 1H), 4.87 (t, J=5.0 Hz, 1H), 4.00-4.14 (m, 2H), 3.83-3.97 (m, 3H), 3.17-3.32 (m, 2H), 3.11 (dd, J=12.5, 4.8 Hz, 1H), 2.96-3.06 (m, 1H), 1.97-2.29 (m, 4H), 1.74-1.91 (m, 2H), 1.58-1.73 (m, 5H), 1.15-1.35 (m, 2H), 0.95 (d, J=6.5 Hz, 3H); MS (APCI, M+H$^+$) $C_{25}H_{35}N_4O_3$, calcd. 439.3. found 439.4.

Step 5: Preparation of N,N-dimethyl-3-(4-(2-((1s, 4S)-4-methylcyclohexylamino)-4-((R)-tetrahydrofuran-3-yloxy)pyrimidin-5-yl)phenoxy)pyrrolidine-1-carboxamide (19)

(19)

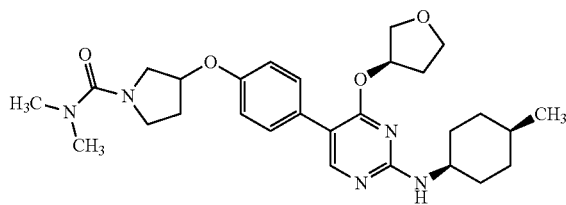

To a mixture of N-((1S,4S)-4-methylcyclohexyl)-5-(4-(pyrrolidin-3-yloxy)phenyl)-4-((R)-tetrahydrofuran-3-yloxy)pyrimidin-2-amine (18) (70 mg, 0.16 mmol) and saturated aqueous Na$_2$CO$_3$ (2 mL) in dichloromethane (5 mL) was added dropwise N,N-dimethylcarbamyl chloride (111 mg, 1.04 mmol). The resulting mixture was stirred for 1 hr at room temperature. After this time, the organic layer was separated and the aqueous phase was extracted with dichloromethane (2×5 mL). The combined organic extracts were dried (MgSO$_4$) and concentrated under reduced pressure. The residue was purified by preparative thin layer chromatography (silica gel, eluting with 3% methanol in chloroform) to give the title compound (19) (35 mg, 43%) as a white solid. $^1$H NMR (CDCl$_3$, 400 MHz) δ 7.38 (d, J=8.8 Hz, 2H), 6.89 (d, J=8.8 Hz, 2H), 5.53-5.65 (m, 1H), 5.28 (bs, 1H), 4.84-4.96 (m, 1H), 3.99-4.18 (m, 2H), 3.78-3.99 (m, 4H), 3.59-3.73 (m, 1H), 3.43-3.57 (m, 2H), 2.86 (s, 6H), 1.99-2.33 (m, 4H), 1.74-1.89 (m, 2H), 1.56-1.73 (m, 5H), 1.17-1.36 (m, 2H), 0.95 (d, J=6.5 Hz, 3H); MS (APCI, M+H$^+$) $C_{28}H_{40}N_5O_4$, calcd. 510.3. found 510.4.

Example 5

Preparation of N-((1s,4S)-4-methylcyclohexyl)-5-(4-(1-(methylsulfonyl)pyrrolidin-3-yloxy)phenyl)-4-((R)-tetrahydrofuran-3-yloxy)pyrimidin-2-amine (20)

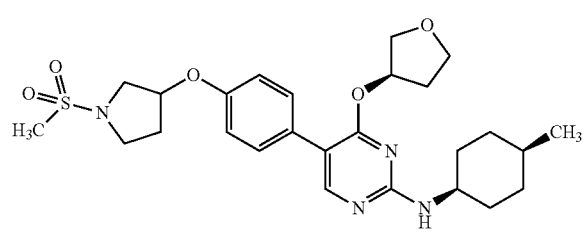

To a mixture of N-((1s,4S)-4-methylcyclohexyl)-5-(4-(pyrrolidin-3-yloxy)phenyl)-4-((R)-tetrahydrofuran-3-yloxy)pyrimidin-2-amine (18) (70 mg, 0.16 mmol) and saturated aqueous Na$_2$CO$_3$ (2 mL) in dichloromethane (5 mL) was added dropwise methanesulfonyl chloride (118 mg, 1.04 mmol). The resulting mixture was stirred for 1 h at room temperature. After this time, the organic layer was separated and the aqueous phase was extracted with dichloromethane (2×5 mL). The organic extracts were combined, dried (MgSO$_4$) and concentrated under reduced pressure. The residue was purified by preparative thin layer chromatography (silica gel, eluting with 3% methanol in chloroform) and then again by preparative HPLC to give the title compound (20) (18 mg, 22%) as a white solid. $^1$H NMR (CDCl$_3$, 400 MHz) δ 8.07 (s, 1H), 7.40 (d, J=8.5 Hz, 2H), 6.85 (d, J=8.8 Hz, 2H), 5.60 (t, J=5.6 Hz, 1H), 5.17 (bs, 1H), 4.95 (t, J=4.0 Hz, 1H), 4.00-4.12 (m, 2H), 3.83-3.97 (m, 3H), 3.55-3.72 (m, 3H), 3.41-3.54 (m, 1H), 2.86 (s, 3H), 2.30-2.40 (m, 1H), 2.07-2.30 (m, 3H), 1.75-1.88 (m, 2H), 1.57-1.74 (m, 5H), 1.18-1.33 (m, 2H), 0.95 (d, J=6.3 Hz, 3H); MS (APCI, M+H$^+$) $C_{26}H_{37}N_4O_5S$, calcd. 517.2. found 517.2.

Example 6

Preparation of 4-((R)-tetrahydrofuran-3-yloxy)-5-(4-((S)-tetrahydrofuran-3-yloxy)phenyl)-N-(cis-4-methylcyclohexyl)pyrimidin-2-amine hydrochloride salt

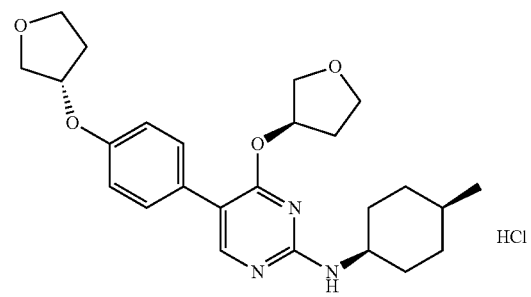

Step 1: Preparation of (R)-tetrahydrofuran-3-yl 4-methylbenzenesulfonate

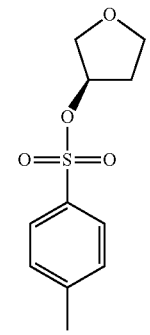

To a mixture of (R)-tetrahydrofuran-3-ol (1 g, 11.4 mmole) and TEA (2.3 g, 22.8 mmole) in DCM (20 mL) at 0° C. was added dropwise 4-methylbenzene-1-sulfonyl chloride (2.2 g, 11.4 mmole). The resulting mixture was stirred at room temperature for 8 h. The mixture was washed with water, dried over MgSO$_4$, filtered, and concentrated. The crude product was purified by ISCO (silica gel, eluting with 15% ethyl acetate in hexane) to give the title compound (2.3 g). MS (ESI) m/z: Found: 243.3 (M$^+$+1). Calc. 242.3 (M$^+$).

Step 2: Preparation of (S)-3-(4-bromophenoxy)-tetrahydrofuran

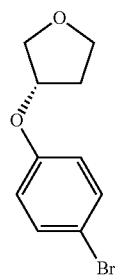

A mixture of 4-bromophenol (1.8 g, 10.5 mmole), (R)-tetrahydrofuran-3-yl 4-methylbenzenesulfonate (2.3 g, 9.5 mmole) and K$_2$CO$_3$ (4.0 g, 29 mmole) in DMF (15 mL) was heated at 85° C. for 15 h. The reaction mixture was diluted with ethyl acetate, washed with water, dried over MgSO$_4$, filtered, and concentrated under vacuum. The crude product was purified by ISCO (silica gel, eluting with 5% ethyl acetate in hexane) to give the title compound (690 mg). MS (ESI) m/z: Found: 244.3 (M$^+$+1). Calc. 243.1 (M$^+$).

Step 3: Preparation of 2-(4-((S)-tetrahydrofuran-3-yloxy)phenyl)-4,4,5,5-tetramethyl-1,3,2-dioxaborolane

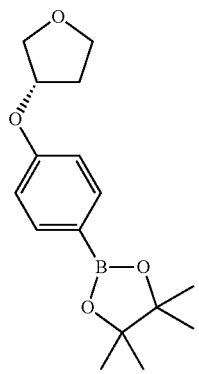

To a mixture of (S)-3-(4-bromophenoxy)-tetrahydrofuran (690 mg, 2.84 mmol), bis(pinacolato)diboron (779.4 mg, 3.07 mmol), potassium acetate (834 mg, 8.5 mmol) and palladium acetate (21.8 mg, 0.087 mmol) in dry DMF (5 mL) was purged with N$_2$ gas for 30 min. The reaction mixture was heated at 85° C. for 9 h. The resulting mixture was partitioned between water (15 mL) and ethyl acetate (20 mL). The aqueous layer was extracted with ethyl acetate (20 mL). The combined ethyl acetate layers was dried over magnesium sulfate, filtered and concentrated in vacuo. The crude product was purified by ISCO (silica gel, eluting with 5 to 10% ethyl acetate in hexane) to give the title compound (640 mg, 77% yield). $^1$H NMR (CDCl$_3$, 400 MHz): δ 7.76 (d, 2H), 6.86 (d, 2H), 4.98-4.96 (m, 1H), 4.03-3.88 (m, 4H), 2.24-2.15 (m, 2H), 1.34 (s, 12H); MS (ESI) m/z: Found: 291.1 (M$^+$+1). Calc. 290.2 (M$^+$).

Step 4: Preparation of 4-((R)-tetrahydrofuran-3-yloxy)-5-(4-((S)-tetrahydrofuran-3-yloxy)phenyl)-N-(cis-4-methylcyclohexyl)pyrimidin-2-amine

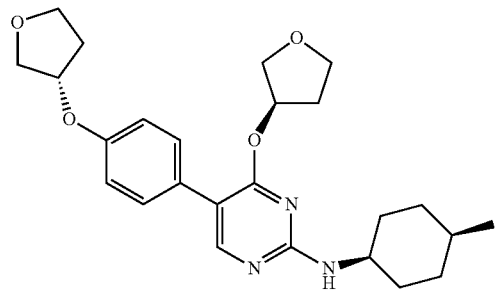

Using the procedure of Example 1, Step 3, 4-((R)-tetrahydrofuran-3-yloxy)-5-bromo-N-(cis-4-methylcyclohexyl)pyrimidin-2-amine was reacted with 2-(4-((S)-tetrahydrofuran-3-yloxy)phenyl)-4,4,5,5-tetramethyl-1,3,2-dioxaborolane to provide the title compound as a free base.

Example 7

Preparation of 4-((R)-tetrahydrofuran-3-yloxy)-5-(4-((R)-tetrahydrofuran-3-yloxy)phenyl)-N-(cis-4-methylcyclohexyl)pyrimidin-2-amine hydrochloride salt

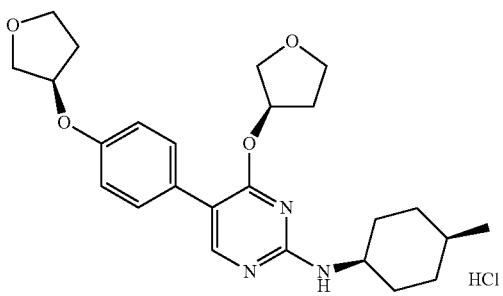

Step 1: Preparation of (S)-tetrahydrofuran-3-yl 4-methylbenzenesulfonate

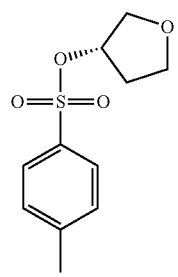

To a mixture of (S)-tetrahydrofuran-3-ol (1 g, 11.4 mmol) and triethylamine (TEA) (2.3 g, 22.8 mmole) in dichloromethane (DCM) (20 mL) at 0° C. was added 4-methylbenzene-1-sulfonyl chloride (2.2 g, 11.4 mmole). The resulting mixture was stirred at room temperature for 8 h. The mixture was washed with water, dried over MgSO$_4$, filtered, and concentrated. The crude product was purified by ISCO (silica gel, 15% ethyl acetate in hexane) to give the title compound (2.5 g). MS (ESI) m/z: Found: 243.3 (M⁺+1). Calc. 242.3 (M⁺).

Step 2: Preparation of (R)-3-(4-bromophenoxy)-tetrahydrofuran

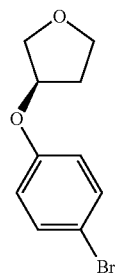

A mixture of 4-bromophenol (2.1 g, 12.4 mmole), (S)-tetrahydrofuran-3-yl 4-methylbenzenesulfonate (2.5 g, 10.3 mmole) and K₂CO₃ (4.3 g, 30.9 mmole) in DMF (15 mL) was heated at 85° C. for 15 h. The mixture was diluted with ethyl acetate, washed with water, dried over MgSO₄, filtered, and concentrated under vacuum. The crude product was purified by ISCO (silica gel, elute: 5% ethyl acetate in hexane) to give the title compound (896 mg). MS (ESI) m/z: Found: 244.3 (M⁺+1). Calc. 243.1 (M⁺).

Step 3: Preparation of 2-(4-((R)-tetrahydrofuran-3-yloxy)phenyl)-4,4,5,5-tetramethyl-1,3,2-dioxaborolane

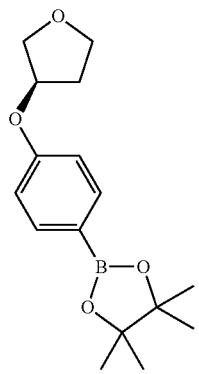

To a stirring solution of (R)-3-(4-bromophenoxy)-tetrahydrofuran (896 mg, 3.1 mmole), bis(pinacolato)diboron (850 mg, 3.35 mmole), potassium acetate (913 mg, 9.3 mmole) and palladium acetate (23.3 mg, 0.093 mmole) in dry DMF (5 mL) was purged with N₂ gas for 10 min. The mixture was then heated at 85° C. for 9 h. The resulting mixture was partitioned between water (15 mL) and ethyl acetate (20 mL). The aqueous solution was extracted with ethyl acetate (20 mL). The combined ethyl acetate extracts were dried over magnesium sulfate, filtered and concentrated in vacuo. The crude product was purified by ISCO (silica gel, eluting with 5 to 10% ethyl acetate in hexane) to give the titled compound (665 mg). ¹H NMR (CDCl₃, 300 MHz): δ 7.79 (d, 2H), 6.89 (d, 2H), 5.02 (m, 1H), 4.06-4.02 (m, 4H), 2.26-2.21 (m, 2H), 1.38 (s, 12H); MS (ESI) m/z: Found: 291.1 (M⁺+1). Calc. 290.2 (M⁺).

Step 4: Preparation of 4-((R)-tetrahydrofuran-3-yloxy)-5-(4-((R)-tetrahydrofuran-3-yloxy)phenyl)-N-(cis-4-methylcyclohexyl)pyrimidin-2-amine

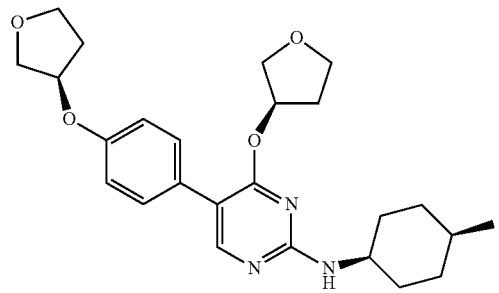

Using the procedure of Example 1 Step 3, 3,4-((R)-tetrahydrofuran-3-yloxy)-5-bromo-N-(cis-4-methylcyclohexyl)pyrimidin-2-amine was reacted with 2-(4-((R)-tetrahydrofuran-3-yloxy)phenyl)-4,4,5,5-tetramethyl-1,3,2-dioxaborolane to provide the title compound.

Example 8

Preparation of (R)-methyl 3-((2-(cis-4-methylcyclohexylamino)-5-(4-morpholinophenyl)pyrimidin-4-yloxy)methyl)pyrrolidine-1-carboxylate

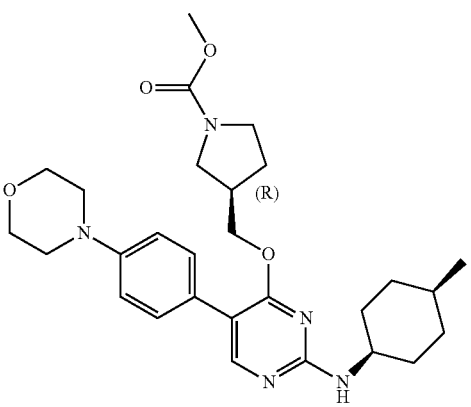

Step 1: Preparation of (R)-tert-butyl 3-((5-bromo-2-chloropyrimidin-4-yloxy)methyl)pyrrolidine-1-carboxylate

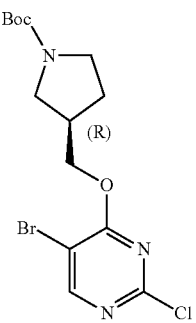

Using the procedure of Example 1 Step 1, 5-bromo-2,4-dichloropyrimidine was reacted with (R)-tert-butyl 3-(hydroxymethyl)pyrrolidine-1-carboxylate to provide the title compound. ¹H NMR (CDCl₃, 400 MHz) δ 8.42 (s, 1H), 4.10 (m, 2H), 3.62-3.17 (m, 5H), 2.72-2.69 (m, 1H), 2.10-2.05 (m, 2H), 1.80-1.75 (m, 1H), 1.44 (s, 9H); MS (ESI) m/z: Calc: 392.68 (M). Found. 337.9 (M⁺-(CH₃)₃C).

Step 2: Preparation of (R)-tert-butyl 3-((2-(cis-4-methylcyclohexylamino)-5-bromopyrimidin-4-yloxy)methyl)pyrrolidine-1-carboxylate

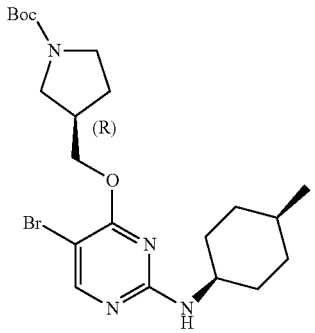

Using the procedure of Example 1 Step 2, (R)-tert-butyl 3-((5-bromo-2-chloropyrimidin-4-yloxy)methyl)pyrrolidine-1-carboxylate was reacted with cis-4-methylcyclohexanamine to provide the title compound at 55% yield. ¹H NMR (CDCl₃, 400 MHz) δ 8.06 (s, 1H), 5.13 (sb, 1H), 4.28 (m, 2H), 3.96 (m, 1H), 3.60-3.15 (m, 4H), 2.66 (m, 1H), 2.02 (m, 1H), 1.77-1.58 (m, 7H), 1.44 (s, 9H), 1.28-1.16 (m, 3H), 0.91 (d, 3H); MS (ESI) m/z: Calc: 544.2 (M⁺). Found. 545.2 (M⁺1).

Step 3: Preparation of (R)-tert-butyl 3-((2-(cis-4-methylcyclohexylamino)-5-(4-morpholinophenyl) pyrimidin-4-yloxy)methyl)pyrrolidine-1-carboxylate

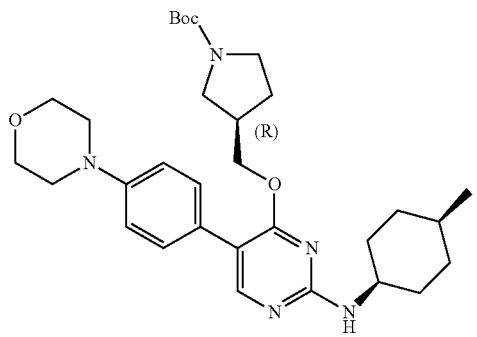

Using the procedure of Example 1 Step 3, (R)-tert-butyl 3-((2-(cis-4-methylcyclohexylamino)-5-bromopyrimidin-4-yloxy)methyl)pyrrolidine-1-carboxylate with 4-morpholinophenylboronic acid to provide the title compound at 85% yield. ¹H NMR (CDCl₃, 400 MHz) δ 8.05 (s, 1H), 7.36 (d, 2H), 6.92 (d, 2H), 5.16 (sb, 1H), 4.30-4.27 (m, 2H), 4.10-4.01 (m, 1H), 386-3.84 (m, 4H), 3.60-3.12 (m, 8H); 2.70-2.62 (m, 1H), 2.05-1.98 (m, 1H), 1.81-1.46 (m, 8H), 1.44 (s, 9H), 1.29-1.21 (m, 3H), 0.93 (d, 3H); MS (ESI) m/z: Found: 552.3 (M⁺1); Calc: 551.4 (M⁺).

Step 4: Preparation of 4-(((R)-pyrrolidin-3-yl)methoxy)-N-(cis-4-methylcyclohexyl)-5-(4-morpholinophenyl)pyrimidin-2-amine

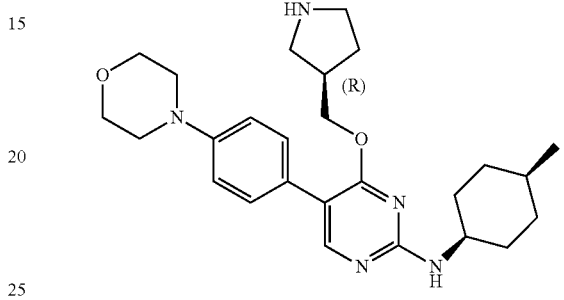

Using the procedure of Example 1 Step 4, (R)-tert-butyl 3-((2-(cis-4-methylcyclohexylamino)-5-(4-morpholinophenyl)pyrimidin-4-yloxy)methyl)pyrrolidine-1-carboxylate was deprotected by TFA to provide the title compound at quantitative yield. MS (ESI) m/z: Found: 452.3 (M⁺1). Calc. 451.3 (M⁺).

Step 5: Preparation of (R)-methyl 3-((2-(cis-4-methylcyclohexylamino)-5-(4-morpholinophenyl)pyrimidin-4-yloxy)methyl)pyrrolidine-1-carboxylate hydrochloride salt

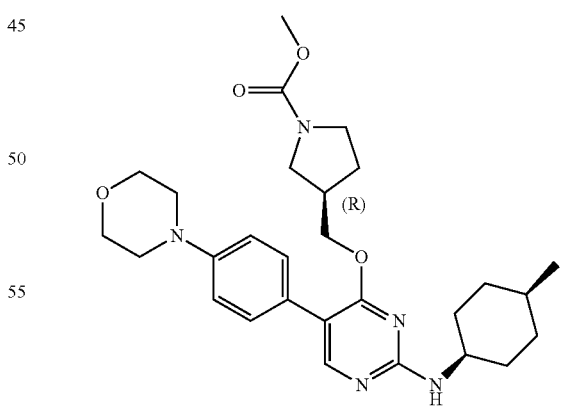

Using the procedure of Example 1 Step 5, 4-(((R)-pyrrolidin-3-yl)methoxy)-N-(cis-4-methylcyclohexyl)-5-(4-morpholinophenyl)pyrimidin-2-amine with methyl chloroformate to provide the title compound. ¹H NMR (CDCl₃, 400 MHz) δ 8.08 (s, 1H), 7.38 (d, 2H), 6.94 (d, 2H), 5.22 (sb, 1H), 4.31 (d, 2H), 4.07 (m, 1H), 3.88 (m, 4H), 3.70 (s, 3H), 3.72-

3.36 (m, 4H), 2.68 (m, 1H), 2.03 (m, 2H), 1.87-1.52 (m, 6H), 1.25 (m, 3H), 0.95 (d, 3H); MS (ESI) m/z: Found: 510.3 (M+1). Calc. 509.3 (M+).

Example 9

Preparation of 4-(((R)-1-methylsulfonyl-pyrrolidin-3-yl)methoxy)-N-(cis-4-methylcyclohexyl)-5-(4-morpholinophenyl)pyrimidin-2-amine

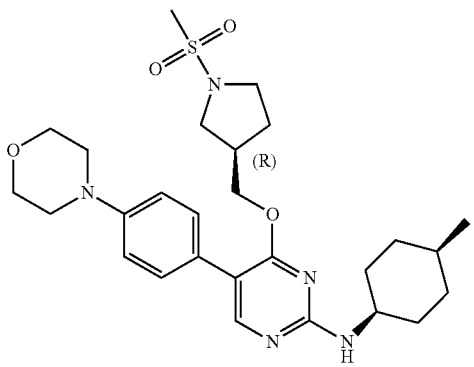

Using the procedure of Example 1 Step 5, 4-(((R)-pyrrolidin-3-yl)methoxy)-N-(cis-4-methylcyclohexyl)-5-(4-morpholinophenyl)pyrimidin-2-amine with methanesulfonyl chloride to provide the title compound in 67% yield. $^1$H NMR (CDCl$_3$, 400 MHz) δ 8.03 (s, 1H), 7.33 (d, 2H), 6.94 (d, 2H), 5.40 (sb, 1H), 4.35 (m, 2H), 4.08 (m, 1H), 3.88 (m, 4H), 3.55-3.31 (m, 4H), 3.18 (m, 4H), 2.76 (s, 3H), 2.17-2.10 (m, 1H), 1.86-1.25 (m, 9H), 0.95 (d, 3H); MS (ESI) m/z: Found: 530.3 (M+1). Calc. 529.3 (M+).

Example 10

Preparation of Methyl 3-((2-((1s,4S)-4-methylcyclohexylamino)-5-(4-morpholinophenyl)pyrimidin-4-yloxy)methyl)azetidine-1-carboxylate

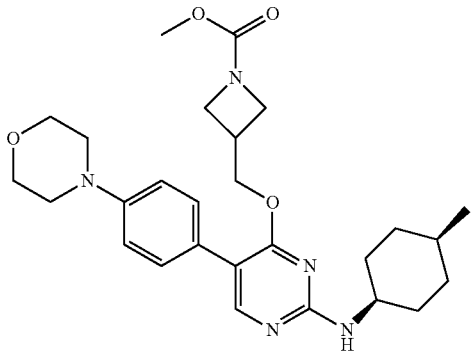

Step 1: Preparation of tert-butyl 3-((5-bromo-2-chloropyrimidin-4-yloxy)methyl)azetidine-1-carboxylate

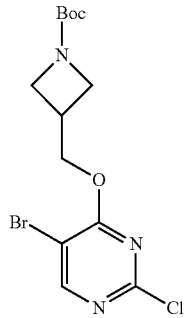

Using the procedure of Example 1 Step 1, 5-bromo-2,4-dichloropyrimidine was reacted with tert-butyl 3-(hydroxymethyl)azetidine-1-carboxylate to provide the title compound at 67% yield. $^1$H NMR (CDCl$_3$, 400 MHz) 8.46 (s, 1H), 4.61 (d, 2H), 4.10 (m, 2H), 3.82 (m, 2H), 3.03 (m, 1H), 1.45 (9H); MS (ESI) m/z: Calc: 377.0 (M+). Found. 322.9 (M+-(CH$_3$)$_3$C+1).

Step 2: Preparation of tert-butyl 3-((2-(cis-4-methylcyclohexylamino)-5-bromopyrimidin-4-yloxy)methyl)azetidine-1-carboxylate

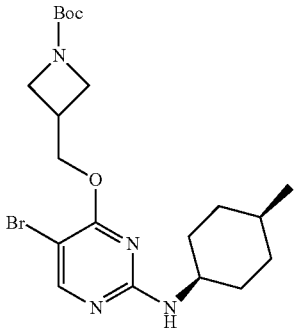

Using the procedure of Example 1 Step 2, tert-butyl 3-((5-bromo-2-chloropyrimidin-4-yloxy)methyl)azetidine-1-carboxylate was reacted with cis-4-methylcyclohexanamine to provide the title compound in 55% yield. $^1$H NMR (CDCl$_3$, 300 MHz) 8.10 (s, 1H), 5.17 (m, 1H), 5.47 (d, 2H), 4.11-4.00 (m, 3H), 3.84-3.79 (m, 2H), 3.02-2.98 (m, 1H), 1.78-1.58 (m, 6H), 1.46 (s, 9H), 1.46-1.27 (m, 3H), 0.95 (d, 3H); MS (ESI) m/z: Calc: 454.2 (M+). Found. 456.1 (M+2).

Step 3: Preparation of tert-butyl 3-((2-(cis-4-methylcyclohexylamino)-5-(4-morpholinophenyl)pyrimidin-4-yloxy)methyl)azetidine-1-carboxylate

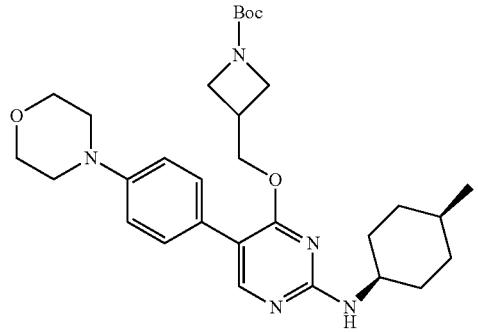

Using the procedure of Example 1 Step 3, tert-butyl 3-((2-(cis-4-methylcyclohexylamino)-5-bromopyrimidin-4- yloxy)methyl)azetidine-1-carboxylate was reacted with 4-morpholinophenylboronic acid to provide the title compound at 78% yield. $^1$H NMR (CDCl$_3$, 400 MHz) 8.02 (s, 1H), 7.30 (d, 2H), 6.85 (d, 2H), 5.38 (sb, 1H), 4.41 (d, 2H), 4.07-3.80 (m, 3H), 4.79-3.70 (m, 5H), 3.11-3.09 (m, 4H), 2.95-2.88 (m, 2H), 1.76-1.45 (m, 6H), 1.44 (s, 9H), 1.20-1.16 (m, 3H), 0.87 (d, 3H); MS (ESI) m/z: Calc: 537.3 (M$^+$). Found. 538.3 (M$^+$1).

Step 4: Preparation of 4-((azetidin-3-yl)methoxy)-N-(cis-4-methylcyclohexyl)-5-(4-morpholinophenyl)pyrimidin-2-amine

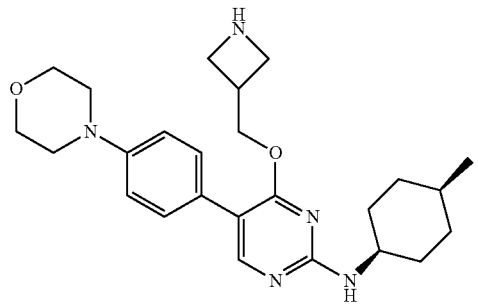

Using the procedure of Example 1 Step 4, tert-butyl 3-((2-(cis-4-methylcyclohexylamino)-5-(4-morpholinophenyl)pyrimidin-4-yloxy)methyl)azetidine-1-carboxylate was deprotected by TFA to provide the title compound at quantitative yield. $^1$H NMR (CDCl$_3$, 400 MHz) 8.02 (s, 1H), 7.32 (d, 2H), 6.87 (d, 2H), 5.24 (sb, 1H), 4.42 (d, 2H), 4.05 (m, 1H), 3.82-3.80 (m, 4H), 3.65 (m, 2H), 3.50 (m, 2H), 3.14-3.11 (m, 4H), 3.05 (bs 1H), 3.03-2.97 (m, 1H), 1.79-1.48 (m, 6H), 1.23-1.18 (m, 3H), 0.88 (d, 3H); MS (ESI) m/z: Calc: 437.3 (M$^+$). Found. 438.3 (M$^+$1).

Step 5: Preparation of methyl 3-((2-(cis-4-methylcyclohexylamino)-5-(4-morpholinophenyl)pyrimidin-4-yloxy)methyl)azetidine-1-carboxylate

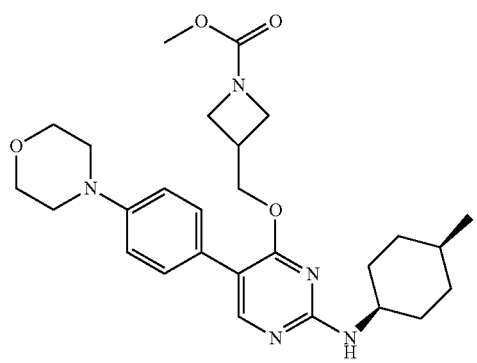

Using the procedure of Example 1 Step 5, 4-((azetidin-3-yl)methoxy)-N-(cis-4-methylcyclohexyl)-5-(4-morpholinophenyl)pyrimidin-2-amine was reacted with methyl chloroformate to provide the title compound at 83% yield. $^1$H NMR (CDCl$_3$, 400 MHz) 8.10 (s, 1H), 7.35 (d, 2H), 6.92 (d, 2H), 5.16 (sb, 1H), 4.47 (d, 2H), 4.12-4.08 (m, 3H), 3.88-3.84 (m, 6H), 3.67 (s, 3H), 3.20-3.18 (m, 4H), 3.10-2.90 (m, 1H), 1.85-1.52 (m, 6H), 1.30-1.20 (m, 3H), 0.94 (d, 3H); MS (ESI) m/z: Calc: 495.3 (M$^+$). Found. 496.3 (M$^+$1).

Example 11

Preparation of 4-((1-methylsulfonyl-azetidin-3-yl)methoxy)-N-(cis-4-methylcyclohexyl)-5-(4-morpholinophenyl)pyrimidin-2-amine

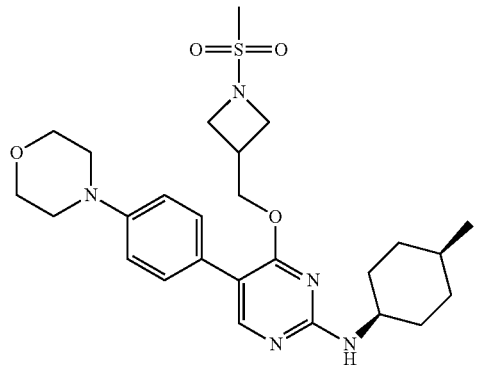

Using the procedure of Example 1 Step 5, 4-((azetidin-3-yl)methoxy)-N-(cis-4-methylcyclohexyl)-5-(4-morpholinophenyl)pyrimidin-2-amine was reacted with methanesulfonyl chloride to provide the title compound in 87% yield. $^1$H NMR (CDCl$_3$, 400 MHz) 8.09 (s, 1H), 7.34 (d, 2H), 6.93 (d, 2H), 5.17 (sb, 1H), 4.50 (d, 2H), 4.08 (m, 1H), 4.01 (m, 2H), 3.87 (m, 4H), 3.82 (m, 2H), 3.17 (m, 4H), 3.05 (m, 1H), 2.66 (s, 3H), 1.85-1.55 (m, 6H), 1.80-1.40 (m, 3H), 0.94 (d, 3H); MS (ESI) m/z: Calc: 515.3 (M). Found. 516.3 (M$^+$1).

Example 12

Preparation of methyl 4-((2-((1s,4S)-4-methylcyclohexylamino)-5-(4-morpholinophenyl)pyrimidin-4-yloxy)methyl)piperidine-1-carboxylate

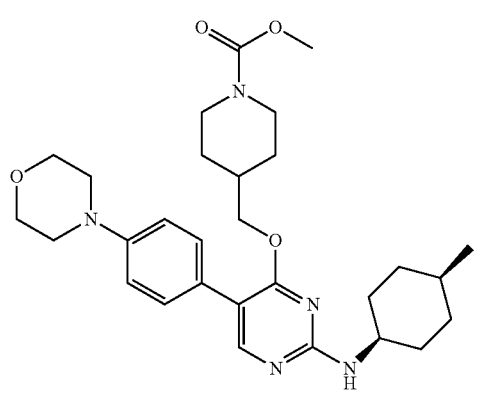

Step 1: Preparation of tert-butyl 4-((5-bromo-2-chloropyrimidin-4-yloxy)methyl)piperidine-1-carboxylate

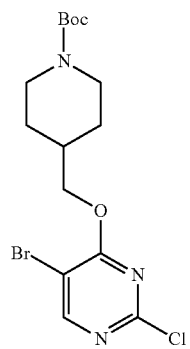

Using the procedure of Example 1 Step 1, 5-bromo-2,4-dichloropyrimidine was reacted with tert-butyl 4-(hydroxymethyl)piperidine-1-carboxylate to provide the title compound in 63% yield. $^1$H NMR (CDCl$_3$, 400 MHz) 8.43 (s, 1H), 4.32 (d, 2H), 4.18 (m, 2H), 2.76 (m, 2H), 2.03 9 m, 1H), 1.80 (m, 2H), 1.46 (s, 9H), 1.34-1.26 (m, 2H); MS (ESI) m/z: Calc: 405.1 (M$^+$). Found. 307.9 (M$^+$-Boc+2).

Step 2: Preparation of tert-butyl 4-((2-(cis-4-methylcyclohexylamino)-5-bromopyrimidin-4-yloxy)methyl)piperidine-1-carboxylate

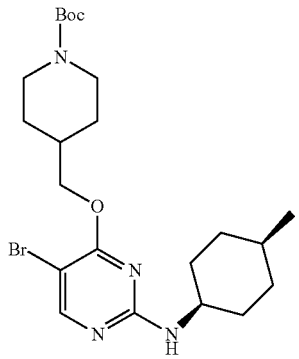

Using the procedure of Example 1 Step 2 tert-butyl 4-((5-bromo-2-chloropyrimidin-4-yloxy)methyl)piperidine-1-carboxylate was reacted with cis-4-methylcyclohexanamine to provide the title compound in 50% yield. $^1$H NMR (CDCl$_3$, 400 MHz) 8.05 (s, 1H), 5.10 (sb, 1H), 4.15 (m, 4H), 3.96 (m, 1H), 2.71 (m, 2H), 1.95 (m, 1H), 1.78-1.48 (m, 9H), 1.44 (s, 9H), 1.28-1.16 (m, 3H), 0.91 (d, 3H); MS (ESI) m/z: Calc: 482.2 (M$^+$). Found. 484.2 (M$^+$+2).

Step 3: Preparation of tert-butyl 4-((2-(cis-4-methylcyclohexylamino)-5-(4-morpholinophenyl)pyrimidin-4-yloxy)methyl)piperidine-1-carboxylate

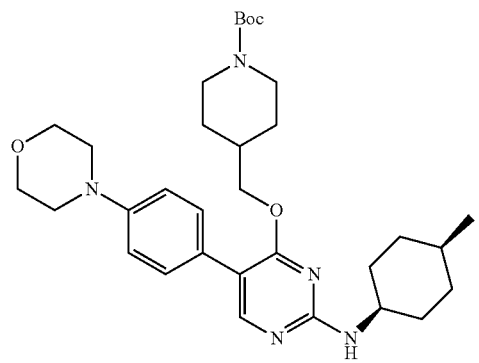

Using the procedure of Example 1 Step 3, tert-butyl 4-((2-(cis-4-methylcyclohexylamino)-5-bromopyrimidin-4-yloxy)methyl)piperidine-1-carboxylate was reacted with 4-morpholinophenylboronic acid to provide the title compound at 70% yield. $^1$H NMR (CDCl$_3$, 400 MHz) 8.03 (s, 1H), 7.35 (d, 2H), 6.89 (d, 2H), 5.17 (sb, 1H), 4.16-4.03 (m, 6H), 3.83 (m, 4H), 3.15 (m, 4H), 2.66 (m, 2H), 1.91-1.44 (m, 11H), 1.41 (s, 9H), 0.95 (d, 3H); MS (ESI) m/z: Calc: 565.4 (M$^+$). Found. 566.3 (M$^+$1).

Step 4: Preparation of 4-((piperidin-4-yl)methoxy)-N-(cis-4-methylcyclohexyl)-5-(4-morpholinophenyl)pyrimidin-2-amine

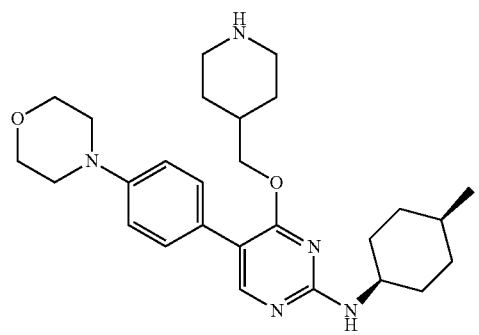

Using the procedure of Example 1 Step 4, tert-butyl 4-((2-(cis-4-methylcyclohexylamino)-5-(4-morpholinophenyl)pyrimidin-4-yloxy)methyl)piperidine-1-carboxylate was deprotected by TFA to provide the title compound. MS (ESI) m/z: Calc: 465.3 (M⁺). Found. 466.3 (M⁺1).

Step 5: Preparation of methyl 4-((2-(cis-4-methylcyclohexylamino)-5-(4-morpholinophenyl)pyrimidin-4-yloxy)methyl)piperidine-1-carboxylate

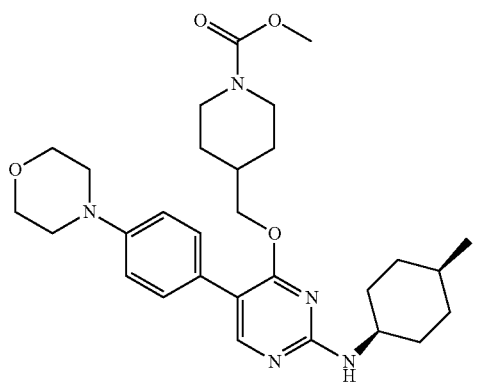

Using the procedure of Example 1 Step 5, 4-((piperidin-4-yl)methoxy)-N-(cis-4-methylcyclohexyl)-5-(4-morpholinophenyl)pyrimidin-2-amine was reacted with methyl chloroformate to provide the title compound. ¹H NMR (CDCl₃, 400 MHz) 8.07 (s, 1H), 7.37 (d, 2H), 6.93 (d, 2H), 5.19 (sb, 1H), 4.19 (d, 2H), 4.07 (m, 3H), 3.88 (m, 4H), 3.69 (s, 3H), 3.20 (m, 4H), 2.77 (m, 2H), 1.97-1.57 (m, 11H), 1.26 (m, 3H), 0.94 (d, 3H); MS (ESI) m/z: Calc: 523.3 (M⁺). Found. 524.3 (M⁺1).

Example 13

Preparation of 4-((1-methylsulfonyl-piperidin-4-yl)methoxy)-N-(cis-4-methylcyclohexyl)-5-(4-morpholinophenyl)pyrimidin-2-amine

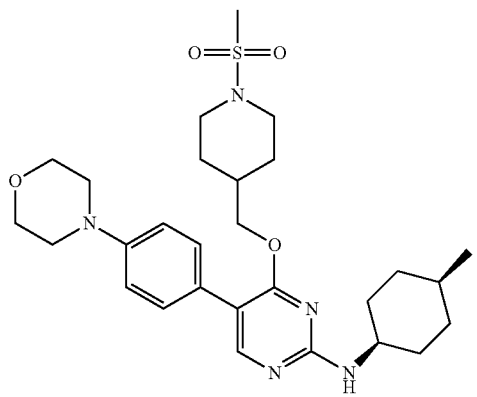

Using the procedure of Example 1 Step 5, 4-((piperidin-4-yl)methoxy)-N-(cis-4-methylcyclohexyl)-5-(4-morpholinophenyl)pyrimidin-2-amine was reacted with methanesulfonyl chloride to provide the title compound at 86% yield. ¹H NMR (CDCl₃, 400 MHz) 8.07 (s, 1H), 7.36 (d, 2H), 6.93 (d, 2 h), 5.20 (s, 1H), 4.23 (d, 2H), 4.07 (m, 1H), 3.89-3.83 (m, 6H), 3.21-3.18 (m, 4H), 2.76 (s, 3H), 2.67 (m, 2H), 1.90-1.24 (m, 14H), 0.94 (d, 3H); MS (ESI) m/z: Calc: 543.3 (M⁺). Found. 544.3 (M⁺1).

Example 14

Preparation of 4-((R)-tetrahydrofuran-3-yloxy)-5-(4-(2-methoxyethyl)phenyl)-N-(cis-4-methylcyclohexyl)pyrimidin-2-amine hydrochloride

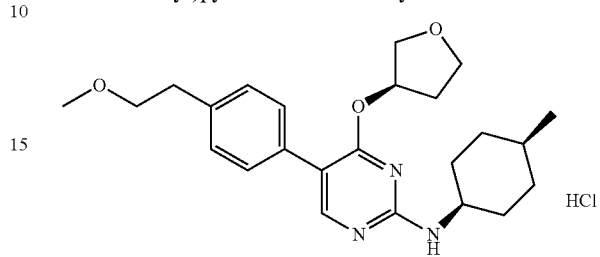

Step 1: Preparation of 1-bromo-4-(2-methoxyethyl)benzene

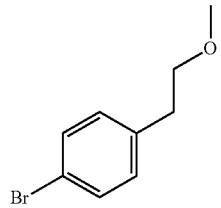

To a solution of 2-(4-bromophenyl)ethanol (1 g, 5 mmol) in anhydrous THF (10 mL) was added NaH (60% oil dispersion, 0.2 g, 5 mmol). The mixture was stirred at room temperature for 30 min and cooled to −0° C. Iodomethane (920 mg, 6.5 mmole) was added slowly to the mixture and stirred for 8 h. The reaction mixture was then quenched by adding water, extracted with ethyl acetate. The combined organic extracts were dried over MgSO₄, filtered, and concentrated. The residue was purified by flash chromatography (silica gel, 5% ethyl acetate in hexane) to give the title compound as a colorless (1 g, 93% yield). ¹H NMR (CDCl₃, 400 MHz): 7.39 (d, 2H), 7.08 (d, 2H), 3.56 (t, 2H), 3.33 (s, 3H), 2.82 (t, 2H); MS (ESI) m/z. Calc. 215.1 (M⁺). Found: 216.3 (M⁺+1), 218.1 (M⁺+3).

Step 2: Preparation of 4-(2-methoxyethyl)phenylboronic acid

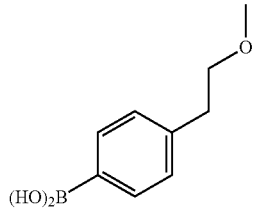

To a solution of 1-bromo-4-(2-methoxyethyl)benzene (1 g, 4.6 mmole) in THF (15 mL) at −78° C. was added dropwise BuLi (2.5M in hexane) (2.4 mL, 6 mmole). After stirring at −78° C. for 20 min, trimethyl borate (0.62 g, 6 mmole) was added to the mixture at −78° C. The mixture was slowly warmed to room temperature and stirred at room temperature for 1 h. 2N HCl was added to the reaction mixture and stirred for 2 h. The mixture was extracted with ether, washed with water, dried over MgSO$_4$, and filtered. Hexane was added to the ether solution. Solid was precipitated and collected by filtration. The solid was used in the next step without purification. MS (ESI) m/z: Calc: 180.0 (M$^+$). Found: 181.3 (M$^+$+1).

Step 3: Preparation of 4-((R)-tetrahydrofuran-3-yloxy)-5-(4-(2-methoxyethyl)phenyl)-N-(cis-4-methylcyclohexyl)pyrimidin-2-amine hydrochloride

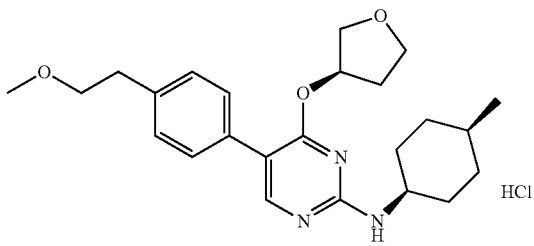

The title compound was prepared according methods used for preparing for Example 1. Using the procedure of Example 1 Step 3, 4-((R)-tetrahydrofuran-3-yloxy)-5-bromo-N-(cis-4-methylcyclohexyl)pyrimidin-2-amine was reacted with 4-(2-methoxyethyl)phenylboronic acid to provide the title compound as a free base in 85% yield. $^1$H NMR (CDCl$_3$, 400 MHz) 9.11 (d, 1H), 7.74 (s, 1H), 7.27-7.24 (m, 4H), 5.65-5.63 (m, 1H), 4.12-4.09 (m, 1H), 4.06-3.88 (m, 4H), 3.62 (t, 2H), 3.35 (s, 3H), 2.90 (t, 2H), 2.30-2.15 (m, 2), 1.85-1.80 (m, 2H), 1.65-1.46 (m, 9H), 0.97 (d, 3H). MS (ESI) m/z: Calc: 411.3 (M). Found: 412.3 (M$^+$+1). The free base compound was treated with HCl (2M in ether) to provide the title compound.

Example 15

Preparation of 4-((R)-tetrahydrofuran-3-yloxy)-5-(4-(2-methoxyethoxy)phenyl)-N-((1S,4S)-4-methylcyclohexyl)pyrimidin-2-amine hydrochloride

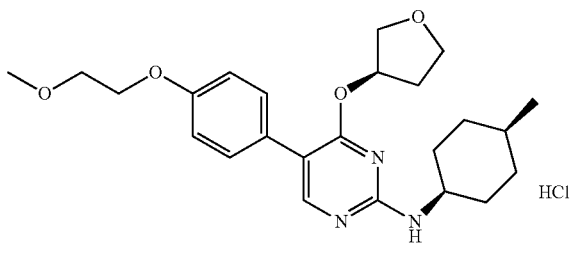

Step 1: Preparation of 2-(4-(2-methoxyethoxy)phenyl)-4,4,5,5-tetramethyl-1,3,2-dioxaborolane

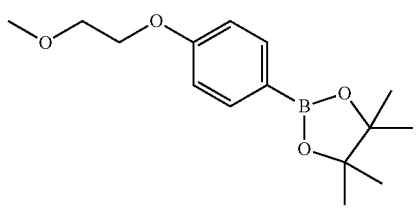

A mixture of 4-(4,4,5,5-tetramethyl-1,3,2-dioxaborolan-2-yl)phenol (1 g, 4.5 mmole), 1-bromo-2-methoxyethane (0.7 g, 5 mmole) and K$_2$CO$_3$ (1.3 g, 9 mmole) in DMF (10 mL) was heated at 85° C. for 20 hr, diluted by ethyl acetate, washed by water, dried over MgSO$_4$, filtered, concentrated under vacuum, purified by ISCO (silica gel, elute: 10% ethyl acetate in hexane) to give liquid product (316 mg, 25% yield). MS (ESI) m/z: Calc. 278.2 (M$^+$). Found: 279.3 (M$^+$+1).

Step 2: Preparation of 4-((R)-tetrahydrofuran-3-yloxy)-5-(4-(2-methoxyethoxy)phenyl)-N-((1S,4S)-4-methylcyclohexyl)pyrimidin-2-amine hydrochloride

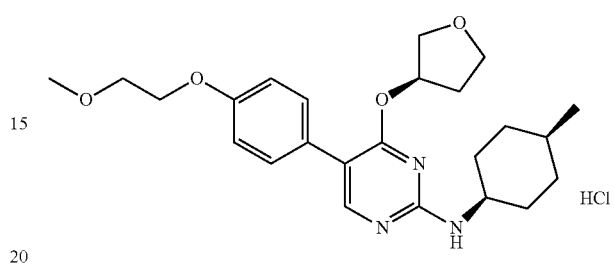

Using the procedure of Example 1 Step 3, 4-((R)-tetrahydrofuran-3-yloxy)-5-bromo-N-(cis-4-methylcyclohexyl)pyrimidin-2-amine was reacted with 2-(4-(2-methoxyethoxy)phenyl)-4,4,5,5-tetramethyl-1,3,2-dioxaborolane to provide the title compound as the free base at 75% yield. $^1$H NMR (CDCl$_3$, 400 MHz) 9.01 (d, 1H), 7.35 (s, 1H), 7.19 (d, 2H), 6.90 (d, 2H), 5.56-5.38 (m, 1H), 4.07-3.67 (m, 8H), 3.37 (s, 1H), 2.24-2.05 (m, 2H), 1.80-1.78 (m 2H), 1.61-1.37 (m, 9H), 0.91 (d, 3H). MS (ESI) m/z: Calc. 427.3 (M$^+$). Found: 428.3 (M$^+$+1). The free base compound was treated with HCl (2M in ether) to provide the title compound.

Example 16

Preparation of 4-((R)-tetrahydrofuran-3-yloxy)-N-((1S,4S)-4-methylcyclohexyl)-5-(4-(tetrahydro-2H-pyran-4-yloxy)phenyl)pyrimidin-2-amine hydrochloride

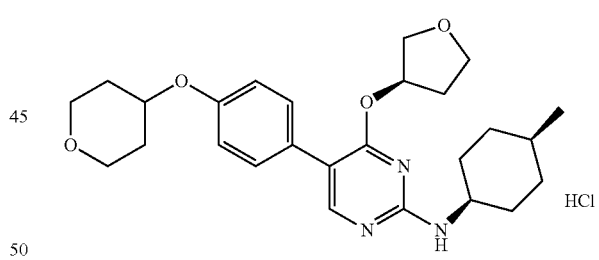

Step 1: Preparation of tetrahydro-2H-pyran-4-yl 4-methylbenzenesulfonate

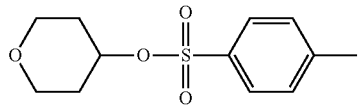

To tetrahydro-2H-pyran-4-ol (1 g, 9.8 mmole) and TEA (2 g, 19.6 mmole) in DCM (20 mL) was added 4-methylbenzene-1-sulfonyl chloride (1.8 g, 9.8 mmole) at 0° C. The mixture was stirred at room temperature for 8 h, washed with water, dried over MgSO$_4$, filtered, and concentrated. The residue was purified by ISCO (silica gel, 15% ethyl acetate in hexane) to give the title compound (2.2 g, 89% yield) as white solid. MS (ESI) m/z: Found: 257.3 (M⁺+1). Calc. 256.3 (M).

Step 2: Preparation of 4,4,5,5-tetramethyl-2-(4-(tetrahydro-2H-pyran-4-yloxy)phenyl)-1,3,2-dioxaborolane

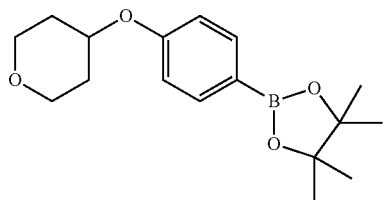

A mixture of 4-(4,4,5,5-tetramethyl-1,3,2-dioxaborolan-2-yl)phenol (1 g, 4.5 mmole), tetrahydro-2H-pyran-4-yl 4-methylbenzenesulfonate (1.4 g, 5.4 mmole) and K₂CO₃ (1.3 g, 9 mmole) in DMF (10 mL) was heated at 85° C. for 20 h. The mixture was diluted with ethyl acetate, washed with water, dried over MgSO₄, filtered, and concentrated under vacuum. The residue was purified by ISCO (silica gel, elute: 10% ethyl acetate in hexane) to give the title compound (335 mg, 24% yield) as a solid. MS (ESI) m/z: Calc. 304.2 (M⁺). Found: 305.3 (M⁺+1).

Step 3: Preparation of 4-((R)-tetrahydrofuran-3-yloxy)-N-((1s,4S)-4-methylcyclohexyl)-5-(4-(tetrahydro-2H-pyran-4-yloxy)phenyl)pyrimidin-2-amine hydrochloride

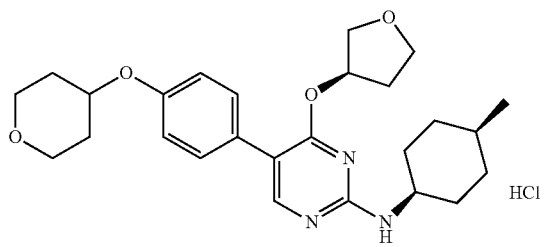

Using the procedure of Example 1 Step 3, 4-((R)-tetrahydrofuran-3-yloxy)-5-bromo-N-(cis-4-methylcyclohexyl)pyrimidin-2-amine was reacted with 4,4,5,5-tetramethyl-2-(4-(tetrahydro-2H-pyran-4-yloxy)phenyl)-1,3,2-dioxaborolane to provide the title compound as a free base at 87% yield. ¹H NMR (CDCl₃, 300 MHz) 9.08 (d, 1H), 7.74 (s, 1H), 7.27 (d, 2H), 6.97 (d, 2H), 5.67-5.64 (m, 1H), 4.55-4.51 (m, 1H), 4.13-3.94 (m, 7H), 3.98-3.59 (m, 2H), 2.31-1.49 (m, 15H), 0.98 (d, 3H). MS (ESI) m/z: Calc. 453.3 (M⁺). Found: 454.3 (M⁺1). The free base compound was treated with HCl (2M in ether) to provide the title compound.

Example 17

Preparation of N-(cis-4-methylcyclohexyl)-4-(1-(methylsulfonyl)-azetidin-3-yloxy)-5-(4-((R)-tetrahydrofuran-3-yloxy)phenyl)pyrimidin-2-amine

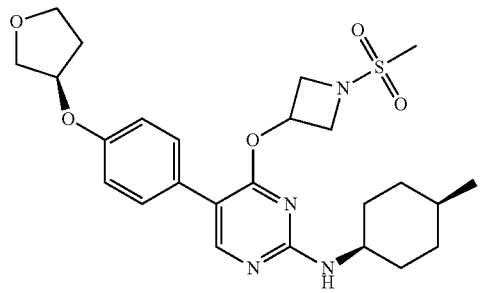

Step 1: Preparation of tert-butyl 3-(5-bromo-2-chloropyrimidin-4-yloxy)azetidine-1-carboxylate

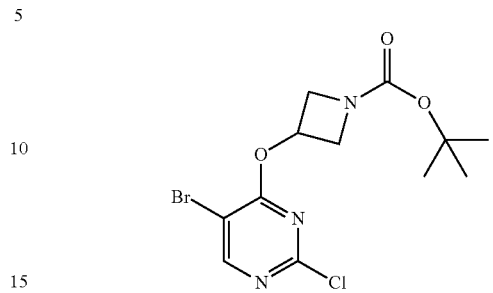

To a solution of tert-butyl 3-hydroxyazetidine-1-carboxylate (4.1 g, 23.7 mmole) in anhydrous THF (100 mL) at 0° C. was added NaH (60% in mineral oil, 1.33 g, 33.2 mmol). The mixture was stirred at 0° C. for 4 5 min and then room temperature for 2 h until there was no hydrogen bubbles generated. This mixture was added slowly to a solution of 5-bromo-2,4-dichloropyrimidine (10.8 g, 47.4 mmol) in THF (100 mL) at −20° C., and then the reaction mixture was stirred at the same temperature for 2 h and then at room temperature for 3 h. The reaction was quenched with water and extracted with EtOAc. The organic layer was separated, dried (Na₂SO₄) and concentrated in vacuo. The residue was purified using flash chromatography (silica gel, 5-10% EtOAc in hexanes) to give the title compound (6 g, 70% yield) as a white solid. MS (ESI) m/z: Calc. 363.0 (M⁺). Found: 309.1 (M⁺+2-tButyl).

Step 2: Preparation of tert-Butyl 3-(5-bromo-2-(cis-4-methylcyclohexylamino)pyrimidin-4-yloxy)azetidine-1-carboxylate

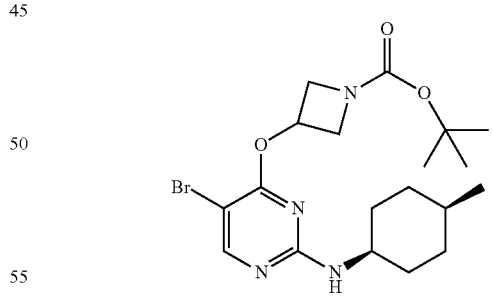

A mixture of tert-butyl 3-(5-bromo-2-chloropyrimidin-4-yloxy)azetidine-1-carboxylate (6 g, 16.4 mmol), cis-4-methylcyclohexanamine hydrochloride (2.4 5g, 16.4 mmol) and Et₃N (7 mL, 49.2 mmol) in EtOH (20 mL) was executed in microwave reactor at 130° C. for 2 h. The resulting mixture was concentrated under vacuum. The residue was purified by flash chromatography (silica gel, eluted by 10 to 20% ethyl acetate in DCM) to give the titled compound (6.5 g, 90% yield). MS (ESI) m/z: Calc. 440.1 (M⁺). Found: 442.1 (M⁺+2).

Step 3: Preparation of 4-(azetidin-3-yloxy)-5-bromo-N-(cis-4-methylcyclohexyl)pyrimidin-2-amine

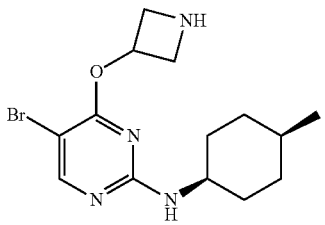

To tert-butyl 3-(5-bromo-2-(cis-4-methylcyclohexylamino)pyrimidin-4-yloxy)azetidine-1-carboxylate (6.5 g, 14 mmol) in DCM (25 mL) was added TFA (4 mL). The mixture was stirred at room temperature for 4 h, diluted with DCM, washed with 1N NaOH solution, water, dried over sodium sulfate, filtered and concentrated to dryness. MS (ESI) m/z Calc. 340.1 ($M^+$). Found: 342.1 ($M^++2$).

Step 4: Preparation of 5-bromo-N-(cis-4-methylcyclohexyl)-4-(1-(methylsulfonyl)azetidin-3-yloxy)pyrimidin-2-amine

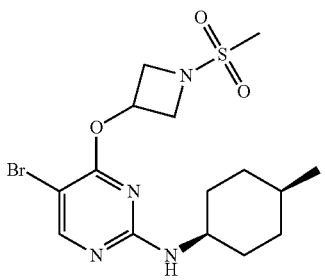

To a solution of 4-(azetidin-3-yloxy)-5-bromo-N-(cis-4-methylcyclohexyl)-pyrimidin-2-amine (1.24 g, 3.64 mmol) and $Et_3N$ (0.6 mL, 3.64 mmol) in DCM (20 mL) at 0° C. was added methanesulfonyl chloride (417 mg, 3.64 mmol). The mixture was stirred at 0° C. for 5 h, diluted by DCM, washed with saturated aqueous sodium carbonate solution and water, dried over sodium sulfate, filtered, and concentrated. The residue was purified by flash chromatography (silica gel, eluted by 1% methanol in DCM) to give the title compound as a white solid (1.3 g, 85% yield). MS (ESI) m/z: Calc. 418.1 ($M^+$). Found: 420.1 ($M^++2$).

Step 5: Preparation of (S)-tetrahydrofuran-3-yl 4-methylbenzenesulfonate

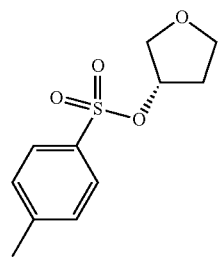

To a solution of (R)-tetrahydrofuran-3-ol (3 g, 34.1 mmole) and $Et_3N$ (6.9 g, 68.2 mmole) in DCM (40 mL) at 0° C. was added 4-methylbenzene-1-sulfonyl chloride (7.2 g, 37.5 mmole. The mixture was stirred at room temperature for 8 h. The mixture was washed with water, dried over $MgSO_4$, filtered, and concentrated. The residue was purified by flash chromatography (silica gel, 15% ethyl acetate in hexane) to give the title compound (6.8 g, 83% yield). MS (ESI) m/z: Calc. 242.1 ($M^+$). Found: 243.1 ($M^++1$).

Step 6: Preparation of (R)-4,4,5,5-tetramethyl-2-(4-(tetrahydrofuran-3-yloxy)phenyl)-1,3,2-dioxaborolane

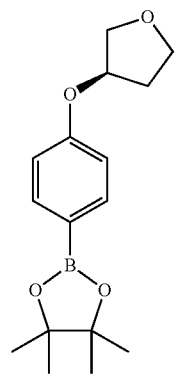

A mixture of 4-(4,4,5,5-tetramethyl-1,3,2-dioxaborolan-2-yl)phenol (6.3 g, 28.5 mmole), (S)-tetrahydrofuran-3-yl 4-methylbenzenesulfonate (6.8 g, 28 mmol) and $K_2CO_3$ (8.0 g, 58 mmole) in DMF (25 mL) was heated at 85° C. for 15 h. The reaction mixture was diluted with ethyl acetate, washed with water, dried over $MgSO_4$, filtered, and concentrated under vacuum. The residue was purified by flash chromatography (silica gel, elute: 5% ethyl acetate in hexane) to give the title compound (2.4 g, 30% yield). MS (ESI) m/z: Calc. 290.1 ($M^+$). Found: 291.1 ($M^++1$).

Step 7: Preparation of N-(cis-4-methylcyclohexyl)-4-(1-(methylsulfonyl)azetidin-3-yloxy)-5-(4-((R)-tetrahydrofuran-3-yloxy)phenyl)pyrimidin-2-amine

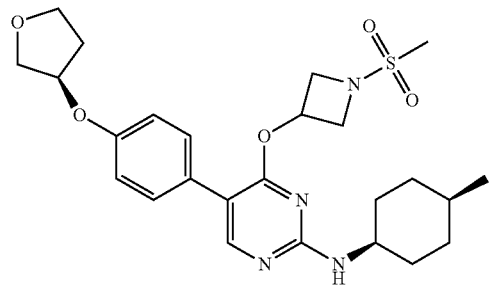

Using the procedure of Example 1 Step 3, 5-bromo-N-(cis-4-methylcyclohexyl)-4-(1-(methylsulfonyl)azetidin-3-yloxy)pyrimidin-2-amine was reacted with (R)-4,4,5,5-tetramethyl-2-(4-(tetrahydrofuran-3-yloxy)phenyl)-1,3,2-dioxaborolane to provide the title compound (18 mg, 45% yield). $^1H$ NMR ($CDCl_3$, 400 MHz) 8.12 (s, 1H), 7.38 (m, 2H), 6.91 (m, 2H), 5.34 (m, 1H), 5.20 (sb, 1H), 4.95 (m, 1H), 4.31 (m, 2H), 4.09-3.92 (m, 6H), 2.90 (s, 3H), 2.22 (m, 2H), 1.80-1.57 (m, 6H), 1.23 (m, 2H), 0.94 (d, 3H). MS (ESI) m/z: Calc. 502.2 (M+). Found: 503.1 (M++1).

Example 18

Preparation of N-(cis-4-methylcyclohexyl)-4-(1-(methylsulfonyl)azetidin-3-yloxy)-5-(4-((S)-tetrahydrofuran-3-yloxy)phenyl)pyrimidin-2-amine

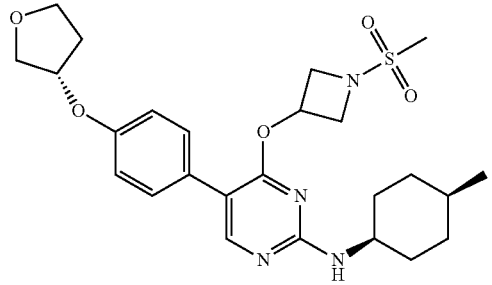

Step 1: Preparation of (S)-tetrahydrofuran-3-yl 4-methylbenzenesulfonate

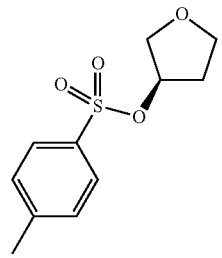

To a solution of (R)-tetrahydrofuran-3-ol (3 g, 34.1 mmole) and Et₃N (6.9 g, 68.2 mmole) in DCM (40 mL) at 0° C. was added 4-methylbenzene-1-sulfonyl chloride (7.2 g, 37.5 mmole). The mixture was stirred at room temperature for 8 h. The mixture was washed with water, dried over MgSO₄, filtered, and concentrated. The residue was purified by flash chromatography (silica gel, 15% ethyl acetate in hexane) to give the title compound (6.6 g, 80% yield). MS (ESI) m/z: Calc. 242.1 (M+). Found: 243.1 (M++1).

Step 2: Preparation of (S)-4,4,5,5-tetramethyl-2-(4-(tetrahydrofuran-3-yloxy)phenyl)-1,3,2-dioxaborolane

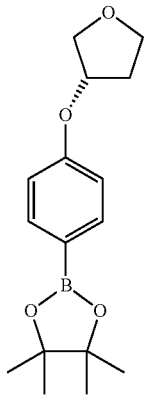

A mixture of 4-(4,4,5,5-tetramethyl-1,3,2-dioxaborolan-2-yl)phenol (5 g, 22.8 mmole), (R)-tetrahydrofuran-3-yl 4-methylbenzenesulfonate (6.6 g, 22.8 mmol) and K₂CO₃ (8.0 g, 58 mmole) in DMF (25 mL) was heated at 85° C. for 15 h. The reaction mixture was diluted with ethyl acetate, washed with water, dried over MgSO₄, filtered, and concentrated under vacuum The residue was purified by flash chromatography (silica gel, elute: 5% ethyl acetate in hexane) to give the title compound (2.4 g, 30% yield). MS (ESI) m/z: Calc. 290.2 (M+). Found: 291.1 (M+1).

Step 3: Preparation of N-(cis-4-methylcyclohexyl)-4-(1-(methylsulfonyl)azetidin-3-yloxy)-5-(4-((S)-tetrahydrofuran-3-yloxy)phenyl)pyrimidin-2-amine

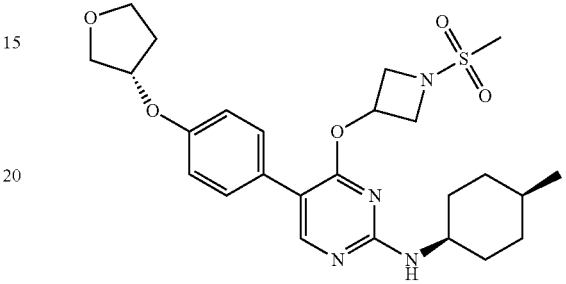

Using the procedure of Example 1 Step 3, 5-bromo-N-(cis-4-methylcyclohexyl)-4-(1-(methylsulfonyl)azetidin-3-yloxy)pyrimidin-2-amine was reacted with (S)-4,4,5,5-tetramethyl-2-(4-(tetrahydrofuran-3-yloxy)phenyl)-1,3,2-dioxaborolane to provide the title compound (105 mg, 46% yield). ¹H NMR (CDCl₃, 400 MHz) 8.12 (s, 1H), 7.38 (m, 2H), 6.91 (m, 2H), 5.34 (m, 1H), 5.20 (sb, 1H), 4.95 (m, 1H), 4.31 (m, 2H), 4.09-3.92 (m, 6H), 2.90 (s, 3H), 2.22 (m, 2H), 1.80-1.57 (m, 6H), 1.23 (m, 2H), 0.94 (d, 3H). MS (ESI) m/z: Calc. 502.2 (M+). Found: 503.1 (M++1).

Examples 19-248

Compounds listed in Table 2 below were prepared using procedures analogous to those described above in Examples 1-18 using appropriate starting materials which are available commercially, prepared based on procedures known in the art, or prepared in a manner analogous to routes described above for other intermediates.

TABLE 2

| Example No. | Compound Name | MS Calc: M+ | MS Found M+ +1 |
|---|---|---|---|
| 19 | 5-(2,3-dihydrobenzo[b][1,4]dioxin-6-yl)-4-(3-methoxybenzyloxy)-N-((1s,4s)-4-methylcyclohexyl)pyrimidin-2-amine | 461.2 | 462.3 |
| 20 | 5-(2,3-dihydrobenzo[b][1,4]dioxin-6-yl)-N-(2,6-dimethylcyclohexyl)-4-((R)-tetrahydrofuran-3-yloxy)pyrimidin-2-amine | 425.2 | 426.5 |
| 21 | N-((1s,4s)-4-methylcyclohexyl)-4-(oxetan-3-yloxy)-5-(4-(piperidin-1-yl)phenyl)pyrimidin-2-amine | 422.3 | 423.4 |
| 22 | 5-(4-methyl-3,4-dihydro-2H-benzo[b][1,4]oxazin-7-yl)-N-((1s,4s)-4-methylcyclohexyl)-4-(oxetan-3-yloxy)pyrimidin-2-amine | 410.2 | 411.3 |
| 23 | 1-(3-(5-(2,3-dihydrobenzo[b][1,4]dioxin-6-yl)-2-((1s,4s)-4-methylcyclohexylamino)pyrimidin-4-yloxy)pyrrolidin-1-yl)ethanone | 452.2 | 453.3 |
| 24 | isopropyl 3-(5-(2,3-dihydrobenzo[b][1,4]dioxin-6-yl)-2-((1s,4s)-4-methylcyclohexylamino)pyrimidin-4-yloxy)pyrrolidine-1-carboxylate | 496.3 | 497.2 |
| 25 | N-((1s,4s)-4-methylcyclohexyl)-4-(oxetan-3-yloxy)-5-(4-(pyrrolidin-1-ylsulfonyl)phenyl)pyrimidin-2-amine | 472.2 | 473.2 |

TABLE 2-continued

| Example No. | Compound Name | MS Calc: M+ | MS Found M+ +1 |
|---|---|---|---|
| 26 | 5-(2,3-dihydrobenzo[b][1,4]dioxin-6-yl)-N-((1s,4s)-4-methylcyclohexyl)-4-(((R)-tetrahydrofuran-3-yl)methoxy)pyrimidin-2-amine | 425.2 | 426.2 |
| 27 | N-((1s,4s)-4-methylcyclohexyl)-5-(4-morpholinophenyl)-4-(((R)-tetrahydrofuran-3-yl)methoxy)pyrimidin-2-amine | 452.3 | 453.2 |
| 28 | 5-(2,3-dihydrobenzo[b][1,4]dioxin-6-yl)-4,6-dimethoxy-N-((1s,4s)-4-methylcyclohexyl)pyrimidin-2-amine | 385.2 | 386.2 |
| 29 | 5-(2-methyl-2H-indazol-5-yl)-N-((1s,4S)-4-methylcyclohexyl)-4-(((R)-tetrahydrofuran-3-yl)methoxy)pyrimidin-2-amine | 421.3 | 422.2 |
| 30 | 5-(1-methyl-1H-indazol-5-yl)-N-((1s,4S)-4-methylcyclohexyl)-4-(((R)-tetrahydrofuran-3-yl)methoxy)pyrimidin-2-amine | 421.3 | 422.2 |
| 31 | 3-(5-(2,3-dihydrobenzo[b][1,4]dioxin-6-yl)-2-((1s,4s)-4-methylcyclohexylamino)pyrimidin-4-yloxy)-N,N-dimethylpyrrolidine-1-carboxamide | 481.3 | 482.2 |
| 32 | N-((1s,4s)-4-methylcyclohexyl)-5-(1-methylindolin-5-yl)-4-(oxetan-3-yloxy)pyrimidin-2-amine | 394.2 | 395.3 |
| 33 | N-((1s,4s)-4-methylcyclohexyl)-4-((3-methyloxetan-3-yl)methoxy)-5-(4-morpholinophenyl)pyrimidin-2-amine | 452.3 | 453.3 |
| 34 | 5-(2,3-dihydrobenzo[b][1,4]dioxin-6-yl)-N-((1s,4s)-4-methylcyclohexyl)-4-(3-methyloxetan-3-yl)methoxy)pyrimidin-2-amine | 425.2 | 426.2 |
| 35 | N-((1s,4s)-4-methylcyclohexyl)-5-(1-methylindolin-5-yl)-4-((3-methyloxetan-3-yl)methoxy)pyrimidin-2-amine | 422.3 | 423.3 |
| 36 | (S)-methyl 3-(2-((1s,4R)-4-methylcyclohexylamino)-5-(4-morpholinophenyl)pyrimidin-4-yloxy)pyrrolidine-1-carboxylate | 495.3 | 496.3 |
| 37 | methyl 4-(5-(2-methyl-2H-indazol-5-yl)-2-((1s,4s)-4-methylcyclohexylamino)pyrimidin-4-yloxy)piperidine-1-carboxylate | 478.3 | 479.2 |
| 38 | 5-(4-(3,5-dimethyl-1H-pyrazol-1-yl)phenyl)-N-((1s,4S)-4-methylcyclohexyl)-4-((R)-tetrahydrofuran-3-yloxy)pyrimidin-2-amine | 447.3 | 448.2 |
| 39 | 5-(2,3-dihydrobenzofuran-5-yl)-N-((1s,4S)-4-methylcyclohexyl)-4-((R)-tetrahydrofuran-3-yloxy)pyrimidin-2-amine | 395.2 | 396.2 |
| 40 | N-((1s,4S)-4-methylcyclohexyl)-4-((R)-tetrahydrofuran-3-yloxy)-5-(4-(tetrahydrofuran-3-yloxy)phenyl)pyrimidin-2-amine | 439.3 | 440.3 |
| 41 | 4-(1,3-dioxan-5-yloxy)-5-(2,3-dihydrobenzo[b][1,4]dioxin-6-yl)-N-((1s,4s)-4-methylcyclohexyl)pyrimidin-2-amine | 427.2 | 428.2 |
| 42 | 4-(1,3-dioxan-5-yloxy)-N-((1s,4s)-4-methylcyclohexyl)-5-(4-morpholinophenyl)pyrimidin-2-amine | 454.3 | 455.1 |
| 43 | 4-methyl-N-((1s,4s)-4-methylcyclohexyl)-5-(4-morpholinophenyl)-6-((R)-tetrahydrofuran-3-yloxy)pyrimidin-2-amine | 452.3 | 453.3 |
| 44 | methyl 3-(5-(2,3-dihydrobenzo[b][1,4]dioxin-6-yl)-2-((1s,4s)-4-methylcyclohexylamino)pyrimidin-4-yloxy)azetidine-1-carboxylate | 454.2 | 455.3 |
| 45 | 4-((1,3-dioxolan-4-yl)methoxy)-5-(2,3-dihydrobenzo[b][1,4]dioxin-6-yl)-N-((1s,4s)-4-methylcyclohexyl)pyrimidin-2-amine | 427.2 | 428.2 |
| 46 | 4-(2-methoxyethoxy)-N-((1s,4s)-4-methylcyclohexyl)-5-(4-morpholinophenyl)pyrimidin-2-amine | 426.3 | 427.5 |
| 47 | 4-(1-(cyclopropylsulfonyl)pyrrolidin-3-yloxy)-5-(2,3-dihydrobenzo[b][1,4]dioxin-6-yl)-N-((1s,4s)-4-methylcyclohexyl)pyrimidin-2-amine | 514.2 | 515.2 |
| 48 | (R)-methyl 3-(5-(1-methyl-1H-indazol-5-yl)-2-((1s,4S)-4-methylcyclohexylamino)pyrimidin-4-yloxy)pyrrolidine-1-carboxylate | 464.3 | 465.2 |
| 49 | 5-(biphenyl-4-yl)-N-((1s,4s)-4-methylcyclohexyl)-4-(oxetan-3-yloxy)pyrimidin-2-amine | 415.2 | 416.3 |
| 50 | 5-(6-(cyclohexyl(methyl)amino)pyridin-3-yl)-N-((1s,4s)-4-methylcyclohexyl)-4-(oxetan-3-yloxy)pyrimidin-2-amine | 451.3 | 452.2 |
| 51 | N-((1s,4s)-4-methylcyclohexyl)-5-(4-(4-methylpiperazin-1-yl)phenyl)-4-(oxetan-3-yloxy)pyrimidin-2-amine | 437.3 | 438.2 |
| 52 | 5-(4-isopropoxyphenyl)-N-((1s,4s)-4-methylcyclohexyl)-4-(oxetan-3-yloxy)pyrimidin-2-amine | 397.2 | 398.3 |
| 53 | (R)-methyl 3-(5-(4-isopropoxyphenyl)-2-((1s,4S)-4-methylcyclohexylamino)pyrimidin-4-yloxy)pyrrolidine-1-carboxylate | 468.3 | 469.2 |
| 54 | (S)-methyl 3-(2-((1s,4R)-4-methylcyclohexylamino)-5-(1-methylindolin-5-yl)pyrimidin-4-yloxy)pyrrolidine-1-carboxylate | 465.3 | 466.2 |
| 55 | N-((1s,4S)-4-methylcyclohexyl)-5-(6-morpholinopyridin-3-yl)-4-((R)-tetrahydrofuran-3-yloxy)pyrimidin-2-amine | 439.3 | 440.3 |
| 56 | N-((1s,4s)-4-methylcyclohexyl)-5-(6-morpholinopyridin-3-yl)-4-(oxetan-3-yloxy)pyrimidin-2-amine | 425.2 | 426.3 |
| 57 | 5-(2-(methoxymethyl)benzo[d]oxazol-5-yl)-N-((1s,4s)-4-methylcyclohexyl)-4-(oxetan-3-yloxy)pyrimidin-2-amine | 424.2 | 425.2 |
| 58 | N-((1s,4S)-4-methylcyclohexyl)-4-((R)-1-(methylsulfonyl)pyrrolidin-3-yloxy)-5-(4-morpholinophenyl)pyrimidin-2-amine | 515.3 | 516.3 |
| 59 | N-((1s,4s)-4-methylcyclohexyl)-4-(1-(methylsulfonyl)azetidin-3-yloxy)-5-(4-morpholinophenyl)pyrimidin-2-amine | 501.2 | 502.3 |
| 60 | methyl 3-(2-((1s,4s)-4-methylcyclohexylamino)-5-(4-morpholinophenyl)pyrimidin-4-yloxy)azetidine-1-carboxylate | 481.3 | 482.3 |
| 61 | N-((1s,4s)-4-methylcyclohexyl)-5-(4-(2-morpholinoethyl)phenyl)-4-(oxetan-3-yloxy)pyrimidin-2-amine | 452.3 | 453.2 |
| 62 | 5-(2-cyclopropylbenzo[d]oxazol-5-yl)-N-((1s,4S)-4-methylcyclohexyl)-4-((R)-tetrahydrofuran-3-yloxy)pyrimidin-2-amine | 434.2 | 435.2 |
| 63 | 5-(2-cyclopropylbenzo[d]oxazol-5-yl)-N-((1s,4s)-4-methylcyclohexyl)-4-(oxetan-3-yloxy)pyrimidin-2-amine | 420.2 | 421.2 |
| 64 | 5-(2,3-dihydrobenzo[b][1,4]dioxin-6-yl)-N-((1s,4s)-4-methylcyclohexyl)-4-(tetrahydro-2H-thiopyran-4-yloxy)pyrimidin-2-amine | 441.2 | 441.6 |
| 65 | 5-(2,3-dihydrobenzo[b][1,4]dioxin-6-yl)-N-((1s,4s)-4-methylcyclohexyl)-4-(tetrahydro-2H-thiopyran-1-oxide-4-yloxy)pyrimidin-2-amine | 457.2 | 458.3 |
| 66 | 5-(2,3-dihydrobenzo[b][1,4]dioxin-6-yl)-N-((1s,4s)-4- methylcyclohexyl)-4-(tetrahydro-2H-thiopyran-1,1-dioxide-4-yloxy)pyrimidin-2-amine | 473.2 | 474,2 |
| 67 | 5-(2,3-dihydrobenzo[b][1,4]dioxin-6-yl)-N-((1s,4s)-4- methylcyclohexyl)-4-((R)-1-methylpyrrolidin-3-yloxy)pyrimidin-2-amine | 424.3 | 425.3 |
| 68 | 5-(4-((2R,6S)-2,6-dimethylmorpholino)phenyl)-N-((1s,4S)-4-methylcyclohexyl)-4-((R)-tetrahydrofuran-3-yloxy)pyrimidin-2-amine | 466.3 | 467.3 |
| 69 | tert-butyl 4-(4-(2-((1s,4S)-4-methylcyclohexylamino)-4-((R)-tetrahydrofuran-3-yloxy)pyrimidin-5-yl)phenyl)piperazine-1-carboxylate | 537.3 | 538.1 |
| 70 | 1-(3-(5-(2,3-dihydrobenzo[b][1,4]dioxin-6-yl)-2-((1s, 4S)-4-methylcyclohexylamino)pyrimidin-4-yloxy)azetidin-1-yl)ethanone | 438.2 | 439.2 |
| 71 | 5-(2,3-dihydrobenzo[b][1,4]dioxin-6-yl)-N-(1s,4s)-4-methylcyclohexyl)-4-(1-(methylsulfonyl)azetidin-3-yloxy)pyrimidin-2-amine | 474.2 | 475.2 |
| 72 | methyl 4-(2-((1s,4s)-4-methylcyclohexylamino)-5-(4-morpholinophenyl)pyrimidin-4-yloxy)piperidine-1-carboxylate | 509.3 | 510.2 |
| 73 | (R)-N,N-dimethyl-3-(2-((1s,4S)-4-methylcyclohexylamino)-5-(4-morpholinophenyl)pyrimidin-4-yloxy)pyrrolidine-1-carboxamide | 508.3 | 509.3 |
| 74 | 1-(methoxymethyl)-5-(2-((1s,4S)-4-methylcyclohexylamino)-4-((R)-tetrahydrofuran-3-yloxy)pyrimidin-5-yl)indolin-2-one | 452.2 | 453.2 |

TABLE 2-continued

| Example No. | Compound Name | MS Calc: M+ | MS Found M+ +1 |
|---|---|---|---|
| 75 | N-((1s,4s)-4-methylcyclohexyl)-5-(4-(morpholinomethyl)phenyl)-4-(oxetan-3-yloxy)pyrimidin-2-amine | 438.3 | 439.2 |
| 76 | 5-(3-fluoro-4-isopropoxyphenyl)-N-((1s,4s)-4-methylcyclohexyl)-4-(oxetan-3-yloxy)pyrimidin-2-amine | 415.2 | 415.5 |
| 77 | (R)-methyl 3-((2-((1s,4S)-4-methylcyclohexylamino)-5-(4-morpholinophenyl)pyrimidin-4-yloxy)methyl)pyrrolidine-1-carboxylate | 509.3 | 510.3 |
| 78 | N-((1s,4S)-4-methylcyclohexyl)-4-(((R)-1-(methylsulfonyl)pyrrolidin-3-yl)methoxy)-5-(4-morpholinophenyl)pyrimidin-2-amine | 529.3 | 530.3 |
| 79 | methyl 3-((2-((1s,4s)-4-methylcyclohexylamino)-5-(4-morpholinophenyl)pyrimidin-4-yloxy)methyl)azetidine-1-carboxylate | 495.3 | 496.3 |
| 80 | N-((1s,4s)-4-methylcyclohexyl)-4-((1-(methylsulfonyl)azetidin-3-yl)methoxy)-5-(4-morpholinophenyl)pyrimidin-2-amine | 515.3 | 516.3 |
| 81 | methyl 4-((2-((1s,4s)-4-methylcyclohexylamino)-5-(4-morpholinophenyl)pyrimidin-4-yloxy)methyl)piperidine-1-carboxylate | 523.3 | 524.3 |
| 82 | N-((1s,4s)-4-methylcyclohexyl)-4-((1-(methylsulfonyl)piperidin-4-yl)methoxy)-5-(4-morpholinophenyl)pyrimidin-2-amine | 543.3 | 544.3 |
| 83 | 4-(4-methoxyphenyl)-N-((1s,4s)-4-methylcyclohexyl)-5-(4-morpholinophenyl)pyrimidin-2-amine | 458.3 | 459.4 |
| 84 | N-((1s,4s)-4-methylcyclohexyl)-4-(1-(methylsulfonyl)azetidin-3-yloxy)-5-(4-((S)-tetrahydrofuran-3-yloxy)phenyl)pyrimidin-2-amine | 502.2 | 503.1 |
| 85 | (R)-N,N-dimethyl-3-(2-((1s,4s)-4-methylcyclohexylamino)-5-(4-((S)-tetrahydrofuran-3-yloxy)phenyl)pyrimidin-4-yloxy)pyrrolidine-1-carboxamide | 509.3 | 510.3 |
| 86 | methyl 4-(2-((1s,4s)-4-methylcyclohexylamino)-5-(4-((S)-tetrahydrofuran-3-yloxy)phenyl)pyrimidin-4-yloxy)piperidine-1-carboxylate | 510.3 | 511.1 |
| 87 | 3-chloro-2-(2-((1s,4s)-4-methylcyclohexylamino)-5-(4-morpholinophenyl)pyrimidin-4-yloxy)propan-1-ol | 460.2 | 461.2 |
| 88 | 4-(2-((1s,4s)-4-methylcyclohexylamino)-4-((R)-tetrahydrofuran-3-yloxy)pyrimidin-5-yl)phenol | 369.2 | 371.2 |
| 89 | tert-butyl 3-((2-((1s,4s)-4-methylcyclohexylamino)-5-(4-morpholinophenyl)pyrimidin-4-yloxy)azetidine-1-carboxylate | 523.3 | 524.4 |
| 90 | N-((1s,4S)-4-methylcyclohexyl)-5-(4-((tetrahydrofuran-3-yl)methoxy)phenyl)-4-((R)-tetrahydrofuran-3-yloxy)pyrimidin-2-amine | 453.3 | 454.2 |
| 91 | 4-(2-((1s,4s)-4-methylcyclohexylamino)-4-(tetrahydro-2H-pyran-4-yloxy)pyrimidin-5-yl)phenol | 383.2 | 384.2 |
| 92 | N-((1s,4S)-4-methylcyclohexyl)-5-(4-(morpholinosulfonyl)phenyl)-4-((R)-tetrahydrofuran-3-yloxy)pyrimidin-2-amine | 502.2 | 503.3 |
| 93 | N-((1s,4s)-4-methylcyclohexyl)-4-(tetrahydro-2H-pyran-4-yloxy)-5-(4-((R)-tetrahydrofuran-3-yloxy)phenyl)pyrimidin-2-amine | 453.3 | 454.3 |
| 94 | tert-butyl 4-(4-(2-((1s,4S)-4-methylcyclohexylamino)-4-((R)-tetrahydrofuran-3-yloxy)pyrimidin-5-yl)phenyl)piperazine-1-carboxylate | 537.3 | 538.4 |
| 95 | (4-(2-((1s,4s)-4-methylcyclohexylamino)-4-((R)-tetrahydrofuran-3-yloxy)pyrimidin-5-yl)phenyl)(morpholino)methanone | 466.3 | 467.1 |
| 96 | 5-(1-isopropylindolin-5-yl)-N-((1s,4S)-4-methylcyclohexyl)-4-((R)-tetrahydrofuran-3-yloxy)pyrimidin-2-amine | 436.3 | 437.4 |
| 97 | N-((1s,4s)-4-methylcyclohexyl)-5-(4-morpholinophenyl)-4-(tetrahydro-2H-thiopyran-1,1-dioxide-4-yloxy-)pyrimidin-2-amine | 500.3 | 501.3 |
| 98 | N-((1s,4s)-4-methylcyclohexyl)-4-(tetrahydro-2H-pyran-4-yloxy)-5-(4-((S)-tetrahydrofuran-3-yloxy)phenyl)pyrimidin-2-amine | 453.3 | 454.2 |
| 99 | tert-butyl 3-(5-(4-hydroxyphenyl)-2-((1s,4s)-4-methylcyclohexylamino)pyrimidin-4-yloxy)azetidine-1-carboxylate | 454.3 | 455.3 |
| 100 | N-((1s,4S)-4-methylcyclohexyl)-5-(4-(piperazin-1-yl)phenyl)-4-((R)-tetrahydrofuran-3-yloxy)pyrimidin-2-amine | 437.3 | 438.3 |
| 101 | tert-butyl 4-(2-((1s,4S)-4-methylcyclohexylamino)-4-((R)-tetrahydrofuran-3-yloxy)pyrimidin-5-yl)phenylcarbamate | 468.3 | 469.4 |
| 102 | (S)-tert-butyl 3-(4-(2-((1s,4S)-4-methylcyclohexylamino)-4-((R)-tetrahydrofuran-3-yloxy)pyrimidin-5-yl)phenoxy)pyrrolidine-1-carboxylate | 538.3 | 539.4 |
| 103 | methyl 3-(4-(2-((1s,4S)-4-methylcyclohexylamino)-4-((R)-tetrahydrofuran-3-yloxy)pyrimidin-5-yl)phenoxy)pyrrolidine-1-carboxylate | 496.3 | 497.4 |
| 104 | N,N-dimethyl-3-(2-((1s,4S)-4-methylcyclohexylamino)-5-(4-morpholinophenyl)pyrimidin-4-yloxy)azetidine-1-sulfonamide | 530.3 | 531.3 |
| 105 | 5-(2,2-dimethyl-2,3-dihydrobenzofuran-5-yl)-N-((1s,4S)-4-methylcyclohexyl)-4-((R)-tetrahydrofuran-3-yloxy)pyrimidin-2-amine | 423.3 | 424.3 |
| 106 | 4-(4-(2-((1s,4S)-4-methylcyclohexylamino)-4-((R)-tetrahydrofuran-3-yloxy)pyrimidin-5-yl)phenyl)morpholin-3-one | 452.2 | 453.4 |
| 107 | tert-butyl 3-(4-(2-((1s,4S)-4-methylcyclohexylamino)-4-((R)-tetrahydrofuran-3-yloxy)pyrimidin-5-yl)phenoxy)pyrrolidine-1-carboxylate | 538.3 | 539.4 |
| 108 | 5-(3-methylbenzo[d]isoxazol-5-yl)-N-(1s,4S)-4-methylcyclohexyl)-4-((R)-tetrahydrofuran-3-yloxy)pyrimidin-2-amine | 408.2 | 409.3 |
| 109 | tert-butyl 3-(4-(2-((1s,4S)-4-methylcyclohexylamino)-4-((R)-tetrahydrofuran-3-yloxy)pyrimidin-5-yl)phenoxy)azetidine-1-carboxylate | 524.3 | 525.4 |
| 110 | N-((1s,4s)-4-methylcyclohexyl)-5-(4-morpholinophenyl)-4-(tetrahydro-2H-thiopyran-4-yloxy)pyrimidin-2-amine | 468.3 | 469.3 |
| 111 | (R)-N-isopropyl-5-(4-morpholinophenyl)-4-(tetrahydrofuran-3-yloxy)pyrimidin-2-amine | 384.2 | 385.3 |
| 112 | N,N-dimethyl-3-(4-(2-((1s,4S)-4-methylcyclohexylamino)-4-((R)-tetrahydrofuran-3-yloxy)pyrimidin-5-yl)phenoxy)pyrrolidine-1-carboxamide | 509.3 | 510.4 |
| 113 | N-((1s,4S)-4-methylcyclohexyl)-5-(4-(oxetan-3-yloxy)phenyl)-4-((R)-tetrahydrofuran-3-yloxy)pyrimidin-2-amine | 425.2 | 426.2 |
| 114 | N-((1s,4S)-4-methylcyclohexyl)-5-(4-(tetrahydro-2H-thiopyran-4-yloxy)phenyl)-4-((R)-tetrahydrofuran-3-yloxy)pyrimidin-2-amine | 469.2 | 470.2 |
| 115 | N-((1s,4S)-4-methylcyclohexyl)-5-(4-(morpholinomethyl)phenyl)-4-((R)-tetrahydrofuran-3-yloxy)pyrimidin-2-amine | 452.3 | 453.3 |
| 116 | tert-butyl 4-(5-(4-hydroxyphenyl)-2-((1s,4s)-4-methylcyclohexylamino)pyrimidin-4-yloxy)piperidine-1-carboxylate | 482.3 | 483.4 |
| 117 | N-((1s,4S)-4-methylcyclohexyl)-5-(4-(4-(methylsulfonyl)piperazin-1-yl)phenyl)-4-((R)-tetrahydrofuran-3-yloxy)pyrimidin-2-amine | 515.3 | 516.4 |
| 118 | methyl 4-(4-(2-((1s,4S)-4-methylcyclohexylamino)-4-((R)-tetrahydrofuran-3-yloxy)pyrimidin-5-yl)phenyl)piperazine-1-carboxylate | 495.3 | 496.4 |
| 119 | 4-(2-((1s,4s)-4-methylcyclohexylamino)-4-(oxetan-3-yloxy)pyrimidin-5-yl)phenol | 355.2 | 356.1 |
| 120 | N-((1s,4S)-4-methylcyclohexyl)-5-(4-(1-(methylsulfonyl)pyrrolidin-3-yloxy)phenyl)-4-((R)-tetrahydrofuran-3-yloxy)pyrimidin-2-amine | 516.2 | 517.2 |
| 121 | 1-(3-(4-(2-((1s,4S)-4-methylcyclohexylamino)-4-((R)-tetrahydrofuran-3-yloxy)pyrimidin-5-yl)phenoxy)pyrrolidin-1-yl)ethanone | 481.2 | 480.3 |
| 122 | cyclopropyl(3-(2-((1s,4s)-4-methylcyclohexylamino)-5-(4-morpholinophenyl)pyrimidin-4-yloxy)azetidin-1-yl)methanone | 491.3 | 492.4 |
| 123 | tert-butyl 3-(5-(4-(2-methoxyethoxy)phenyl)-2-((1s,4s)-4-methylcyclohexylamino)pyrimidin-4-yloxy)azetidine-1-carboxylate | 512.3 | 513.4 |
| 124 | tert-butyl 4-(2-((1s,4s)-4-methylcyclohexylamino)-5-(4-((S)-tetrahydrofuran-3-yloxy)phenyl)pyrimidin-4-yloxy)piperidine-1-carboxylate | 552.3 | 553.3 |
| 125 | 4-(1-(cyclopropylsulfonyl)azetidin-3-yloxy)-N-((1s,4s)-4-methylcyclohexyl)-5-(4-morpholinophenyl)pyrimidin-2-amine | 527.3 | 528.3 |

TABLE 2-continued

| Example No. | Compound Name | MS Calc: M+ | MS Found M+ +1 |
|---|---|---|---|
| 126 | (R)-N-isopropyl-4-(tetrahydrofuran-3-yloxy)-5-(4-(trifluoromethoxy)phenyl)pyrimidin-2-amine | 383.2 | 384.3 |
| 127 | N-(4-(2-((1s,4S)-4-methylcyclohexylamino)-4-((R)-tetrahydrofuran-3-yloxy)pyrimidin-5-yl)phenyl)isobutyramide | 438.3 | 439.5 |
| 128 | N-((1s,4S)-4-methylcyclohexyl)-5-(4-(pyrrolidin-3-yloxy)phenyl)-4-((R)-tetrahydrofuran-3-yloxy)pyrimidin-2-amine | 438.3 | 439.4 |
| 129 | 5-(4-((isopropylamino)methyl)phenyl)-N-((1s,4S)-4-methylcyclohexyl)-4-((R)-tetrahydrofuran-3-yloxy)pyrimidin-2-amine | 424.3 | 425.2 |
| 130 | 5-(4-((benzylamino)methyl)phenyl)-N-((1s,4S)-4-methylcyclohexyl)-4-((R)-tetrahydrofuran-3-yloxy)pyrimidin-2-amine | 472.3 | 473.5 |
| 131 | N-((1s,4S)-4-methylcyclohexyl)-5-(4-(piperidin-1-ylmethyl)phenyl)-4-((R)-tetrahydrofuran-3-yloxy)pyrimidin-2-amine | 450.3 | 451.4 |
| 132 | 1-(4-(4-(2-((1s,4S)-4-methylcyclohexyl-amino)-4-((R)-tetrahydrofuran-3-yloxy)pyrimidin-5-yl)phenyl)piperazin-1-yl)ethanone | 479.3 | 480.4 |
| 133 | 2-methoxy-1-(3-(2-((1s,4s)-4-methylcyclohexyl-amino)-5-(4-morpholinophenyl)pyrimidin-4-yloxy)azetidin-1-yl)ethanone | 495.3 | 496.4 |
| 134 | 4-(1-(ethylsulfonyl)azetidin-3-yloxy)-N-((1s,4s)-4-methylcyclohexyl)-5-(4-morpholinophenyl)pyrimidin-2-amine | 515.3 | 516.4 |
| 135 | N-((1s,4S)-4-methylcyclohexyl)-5-(4-(piperazin-1-ylmethyl)phenyl)-4-((R)-tetrahydrofuran-3-yloxy)pyrimidin-2-amine | 451.3 | 452.2 |
| 136 | N,N-dimethyl-3-(4-(2-((1s,4S)-4-methylcyclohexyl-amino)-4-((R)-tetrahydrofuran-3-yloxy)pyrimidin-5-yl)phenoxy)azetidine-1-carboxamide | 495.3 | 496.1 |
| 137 | N-((1s,4S)-4-methylcyclohexyl)-5-(4-(tetra-hydro-2H-pyran-3-yloxy)phenyl)-4-((R)-tetrahydrofuran-3-yloxy)pyrimidin-2-amine | 453.3 | 453.9 |
| 138 | methyl 3-(4-(2-((1s,4S)-4-methylcyclohexyl-amino)-4-((R)-tetrahydrofuran-3-yloxy)pyrimidin-5-yl)phenoxy)azetidine-1-carboxylate | 482.3 | 483.1 |
| 139 | 1-(3-(4-(2-((1s,4S)-4-methylcyclohexyl-amino)-4-((R)-tetrahydrofuran-3-yloxy)pyrimidin-5-yl)phenoxy)azetidin-1-yl)ethanone | 466.3 | 467.1 |
| 140 | (3-(2-((1s,4s)-4-methylcyclohexylamino)-5-(4-morpholinophenyl)pyrimidin-4-yloxy)azetidin-1-yl)(morpholino)methanone | 536.3 | 537.0 |
| 141 | N-((1s,4S)-4-methylcyclohexyl)-5-(4-((phenylamino)methyl)phenyl)-4-((R)-tetrahydrofuran-3-yloxy)pyrimidin-2-amine | 458.3 | 459.1 |
| 142 | 5-(4-(2-methoxyethoxy)phenyl)-N-((1s,4s)-4-methylcyclohexyl)-4-(tetrahydro-2H-pyran-4-yloxy)pyrimidin-2-amine | 441.3 | 442.1 |
| 143 | 5-(4-(2-methoxyethoxy)phenyl)-N-((1s,4s)-4-methylcyclohexyl)-4-(tetrahydro-2H-thiopyran-1,1-dioxide-4-yloxy)pyrimidin-2-amine | 489.2 | 490.4 |
| 144 | 4-(4-methoxyphenyl)-5-(2-methyl-2H-indazol-5-yl)-N-((1s,4s)-4-methylcyclohexyl)pyrimidin-2-amine | 427.2 | 427.8 |
| 145 | N-(2,6-dimethylcyclohexyl)-5-(4-morpholino-phenyl)-4-((R)-tetrahydrofuran-3-yloxy)pyrimidin-2-amine | 452.3 | 452.9 |
| 146 | (R)-N-methyl-5-(4-morpholinophenyl)-N-phenyl-4-(tetrahydrofuran-3-yloxy)pyrimidin-2-amine | 432.2 | 432.8 |
| 147 | N-((1s,4S)-4-methylcyclohexyl)-4-((R)-tetrahydro-furan-3-yloxy)-5-(4-(trifluoromethoxy)phenyl)pyrimidin-2-amine | 437.2 | 437.8 |
| 148 | methyl 4-(4-(2-((1s,4S)-4-methylcyclohexyl-amino)-4-((R)-tetrahydrofuran-3-yloxy)pyrimidin-5-yl)benzyl)piperazine-1-carboxylate | 509.3 | 509.8 |
| 149 | N-((1s,4S)-4-methylcyclohexyl)-5-(4-((4-(methylsulfonyl)piperazin-1-yl)methyl)phenyl)-4-((R)-tetrahydrofuran-3-yloxy)pyrimidin-2-amine | 529.3 | 529.8 |
| 150 | 1-(4-(4-(2-((1s,4S)-4-methylcyclohexyl-amino)-4-((R)-tetrahydrofuran-3-yloxy)pyrimidin-5-yl)benzyl)piperazin-1-yl)ethanone | 493.3 | 493.9 |
| 151 | tert-butyl 4-(4-(2-((1s,4S)-4-methylcyclohexyl-amino)-4-((R)-tetrahydrofuran-3-yloxy)pyrimidin-5-yl)benzyl)piperazine-1-carboxylate | 551.4 | 552.2 |
| 152 | N-((1s,4s)-4-methylcyclohexyl)-4-(1-(methylsulfonyl)piperidin-4-yloxy)-5-(4-((S)-tetrahydrofuran-3-yloxy)phenyl)pyrimidin-2-amine | 530.3 | 530.8 |
| 153 | 5-(4-(2-methoxyethoxy)phenyl)-N-((1s,4s)-4-methylcyclohexyl)-4-(1-(methylsulfonyl)azetidin-3-yloxy)pyrimidin-2-amine | 490.2 | 490.8 |
| 154 | N-((1s,4S)-4-methylcyclohexyl)-5-(4-(pyrrolidin-1-yl)phenyl)-4-((R)-tetrahydrofuran-3-yloxy)pyrimidin-2-amine | 422.3 | 422.9 |
| 155 | N-(4-(2-((1s,4S)-4-methylcyclohexylamino)-4-((R)-tetrahydrofuran-3-yloxy)pyrimidin-5-yl)phenylsulfonyl)acetamide | 474.2 | 475.2 |
| 156 | methyl 4-(5-(4-(2-methoxyethoxy)phenyl)-2-((1s,4s)-4-methylcyclohexylamino)pyrimidin-4-yloxy)piperidine-1-carboxylate | 498.3 | 499.4 |
| 157 | N-(2,4-dimethoxybenzyl)-N-(4-(2-((1s,4S)-4-methylcyclohexylamino)-4-((R)-tetrahydrofuran-3-yloxy)pyrimidin-5-yl)benzyl)acetamide | 574.3 | 575.4 |
| 158 | 5-(4-((2,4-dimethoxybenzylamino)methyl)phenyl)-N-((1s,4S)-4-methylcyclohexyl)-4-((R)-tetrahydrofuran-3-yloxy)pyrimidin-2-amine | 532.3 | 532.8 |
| 159 | N-((1s,4S)-4-methylcyclohexyl)-5-(3-((tetrahydro-2H-pyran-4-yl)methoxy)phenyl)-4-((R)-tetrahydrofuran-3-yloxy)pyrimidin-2-amine | 467.3 | 468.3 |
| 160 | N-((1s,4S)-4-methylcyclohexyl)-4-((R)-tetrahydro-furan-3-yloxy)-5-(3-((R)-tetrahydrofuran-3-yloxy)phenyl)pyrimidin-2-amine | 439.3 | 440.3 |
| 161 | N-((1s,4s)-4-methylcyclohexyl)-4-(methylthio)-5-(4-morpholinophenyl)pyrimidin-2-amine | 398.2 | 398.8 |
| 162 | tert-butyl 4-(5-(4-(2-methoxyethoxy)phenyl)-2-((1s,4s)-4-methylcyclohexylamino)pyrimidin-4-yloxy)piperidine-1-carboxylate | 540.3 | 541.4 |
| 163 | 5-(4-(2-methoxyethoxy)phenyl)-N-((1s,4s)-4-methylcyclohexyl)-4-(piperidin-4-yloxy)pyrimidin-2-amine hydrochloride | 476.3 | 443.1 (—HCl) |
| 164 | 4-(2-(2,6-dimethylcyclohexylamino)-4-((R)-tetrahydrofuran-3-yloxy)pyrimidin-5-yl)phenol | 383.2 | 384.2 |
| 165 | N-((1s,4S)-4-methylcyclohexyl)-4-((R)-tetrahydrofuran-3-yloxy)-5-(3-((S)-tetrahydrofuran-3-yloxy)phenyl)pyrimidin-2-amine | 439.3 | 440.2 |
| 166 | 5-(4-(2-methoxyethoxy)phenyl)-N-((1s,4s)-4-methylcyclohexyl)-4-(oxetan-3-yloxy)pyrimidin-2-amine | 413.2 | 414.2 |
| 167 | 5-(4-(2-methoxyethoxy)phenyl)-N-((1s,4s)-4-methylcyclohexyl)-4-(tetrahydro-2H-thiopyran-4-yloxy)pyrimidin-2-amine | 457.2 | 458.2 |
| 168 | N-((1s,4s)-4-methylcyclohexyl)-4-(oxetan-3-yloxy)-5-(4-((S)-tetrahydrofuran-3-yloxy)phenyl)pyrimidin-2-amine | 425.2 | 426.2 |
| 169 | tert-butyl methyl(4-(2-((1s,4S)-4-methylcyclohexyl-amino)-4-((R)-tetrahydrofuran-3-yloxy)pyrimidin-5-yl)phenyl)carbamate | 482.3 | 483.2 |
| 170 | N-(2,6-dimethylcyclohexyl)-4-((R)-tetrahydrofuran-3-yloxy)-5-(4-((S)-tetrahydrofuran-3-yloxy)phenyl)pyrimidin-2-amine | 453.3 | 454.4 |
| 171 | 4-(2-((1s,4S)-4-methylcyclohexylamino)-4-((R)-tetrahydrofuran-3-yloxy)pyrimidin-5-yl)benzamide | 396.2 | 397.1 |
| 172 | 5-(biphenyl-4-yl)-N-((1s,4S)-4-methylcyclo-hexyl)-4-((R)-tetrahydrofuran-3-yloxy)pyrimidin-2-amine | 429.2 | 430.2 |
| 173 | N-((1s,4S)-4-methylcyclohexyl)-5-(4-phenoxy-phenyl)-4-((R)-tetrahydrofuran-3-yloxy)pyrimidin-2-amine | 445.2 | 446.2 |
| 174 | 4-(2-((1s,4S)-4-methylcyclohexylamino)-4-((R)-tetrahydrofuran-3-yloxy)pyrimidin-5-yl)benzenesulfonamide | 432.2 | 433.1 |
| 175 | isopropyl 4-(2-((1s,4s)-4-methylcyclohexyl-amino)-5-(4-((S)-tetrahydrofuran-3-yloxy)phenyl)pyrimidin-4-yloxy)piperidine-1-carboxylate | 538.3 | 539.3 |

TABLE 2-continued

| Example No. | Compound Name | MS Calc: M+ | MS Found M+ +1 |
|---|---|---|---|
| 176 | ethyl 2-(2-((1s,4s)-4-methylcyclohexylamino)-5-(4-morpholinophenyl)pyrimidin-4-yloxy)acetate | 454.3 | 455.5 |
| 177 | N-((1s,4s)-4-methylcyclohexyl)-4-(piperidin-4-yloxy)-5-(4-((S)-tetrahydrofuran-3-yloxy)phenyl)pyrimidin-2-amine hydrochloride | 488.3 | 453.3 (—HCl) |
| 178 | 5-(4-(2-methoxyethyl)phenyl)-N-((1s,4s)-4-methylcyclohexyl)-4-(oxetan-3-yloxy)pyrimidin-2-amine | 397.2 | 398.1 |
| 179 | 4-(isopropylthio)-N-((1s,4s)-4-methylcyclohexyl)-5-(4-morpholinophenyl)pyrimidin-2-amine | 426.3 | 427.2 |
| 180 | 4-(2-((1s,4S)-4-methylcyclohexylamino)-4-((R)-tetrahydrofuran-3-yloxy)pyrimidin-5-yl)benzonitrile | 378.2 | 379.2 |
| 181 | N-((1s,4s)-4-methylcyclohexyl)-5-(4-(tetrahydro-2H-thiopyran-1,1-dioxide-4-yloxy)phenyl)-4-((R)-tetrahydrofuran-3-yloxy)pyrimidin-2-amine | 501.2 | 501.8 |
| 182 | methyl 3-(5-(4-(2-methoxyethyl)phenyl)-2-((1s,4s)-4-methylcyclohexylamino)pyrimidin-4-yloxy)azetidine-1-carboxylate | 454.3 | 455.4 |
| 183 | 5-(4-(1H-tetrazol-5-yl)phenyl)-N-((1s,4S)-4-methylcyclohexyl)-4-((R)-tetrahydrofuran-3-yloxy)pyrimidin-2-amine | 421.2 | 422.3 |
| 184 | tert-butyl 3-(5-(4-(2-methoxyethyl)phenyl)-2-((1s,4s)-4-methylcyclohexylamino)pyrimidin-4-yloxy)azetidine-1-carboxylate | 496.3 | 497.3 |
| 185 | N-((1s,4S)-4-methylcyclohexyl)-4-((R)-tetrahydrofuran-3-yloxy)-5-(3-(tetrahydrofuran-3-yloxy)phenyl)pyrimidin-2-amine | 439.3 | 440.3 |
| 186 | N-((1s,4s)-4-methylcyclohexyl)-5-(4-morpholinophenyl)-4-(tetrahydro-2H-thiopyran-1-oxide-4-yloxy-)pyrimidin-2-amine | 484.3 | 485.2 |
| 187 | 3-(2-((1s,4S)-4-methylcyclohexylamino)-4-((R)-tetrahydrofuran-3-yloxy)pyrimidin-5-yl)benzoic acid | 397.2 | 398.2 |
| 188 | 4-(2-((1s,4S)-4-methylcyclohexylamino)-4-((R)-tetrahydrofuran-3-yloxy)pyrimidin-5-yl)-N-(methylsulfonyl)benzamide | 474.2 | 475.3 |
| 189 | N-(N,N-dimethylsulfamoyl)-4-(2-((1s,4S)-4-methylcyclohexylamino)-4-((R)-tetrahydrofuran-3-yloxy)pyrimidin-5-yl)benzamide | 503.2 | 504.3 |
| 190 | N-cyano-4-(2-((1s,4S)-4-methylcyclohexylamino)-4-((R)-tetrahydrofuran-3-yloxy)pyrimidin-5-yl)benzamide | 421.2 | 422.3 |
| 191 | methyl 3-(5-(4-(2-methoxyethoxy)phenyl)-2-((1s,4s)-4-methylcyclohexylamino)pyrimidin-4-yloxy)azetidine-1-carboxylate | 470.3 | 471.1 |
| 192 | N-(2,4-dimethoxybenzyl)-N-(4-(2-((1s,4S)-4-methylcyclohexylamino)-4-((R)-tetrahydrofuran-3-yloxy)pyrimidin-5-yl)benzyl)benzamide | 636.3 | 637.1 |
| 193 | tert-butyl 3-(2-((1s,4s)-4-methylcyclohexylamino)-5-(4-(morpholinosulfonyl)phenyl)pyrimidin-4-yloxy)azetidine-1-carboxylate | 587.3 | 588.2 |
| 194 | N-(4-(2-((1s,4S)-4-methylcyclohexylamino)-4-((R)-tetrahydrofuran-3-yloxy)pyrimidin-5-yl)benzyl)acetamide | 424.3 | 425.3 |
| 195 | N-(4-(2-((1s,4S)-4-methylcyclohexylamino)-4-((R)-tetrahydrofuran-3-yloxy)pyrimidin-5-yl)benzyl)benzamide | 486.3 | 487.2 |
| 196 | 2-(2-((1s,4s)-4-methylcyclohexylamino)-5-(4-morpholinophenyl)pyrimidin-4-yloxy)acetic acid | 426.2 | 427.1 |
| 197 | 5-(4-(2-methoxyethyl)phenyl)-N-((1s,4s)-4-methylcyclohexyl)-4-(tetrahydro-2H-pyran-4-yloxy)pyrimidin-2-amine | 425.3 | 426.2 |
| 198 | 5-(4-(2-methoxyethyl)phenyl)-N-((1S,4S)-4-methylcyclohexyl)-4-(tetrahydro-2H-thiopyran-1,1-dioxide-4-yloxy)pyrimidin-2-amine | 473.2 | 474.1 |
| 199 | tert-butyl 4-(5-(4-(2-methoxyethyl)phenyl)-2-((1s,4s)-4-methylcyclohexylamino)pyrimidin-4-yloxy)piperidine-1-carboxylate | 524.3 | 525.3 |
| 200 | 5-(4-(2-methoxyethoxy)phenyl)-4-(1-methylazetidin-3-yloxy)-N-((1s,4s)-4-methylcyclohexyl)pyrimidin-2-amine | 426.3 | 427.2 |
| 201 | 5-(4-(2-methoxyethyl)phenyl)-4-(1-methylazetidin-3-yloxy)-N-((1s,4s)-4-methylcyclohexyl)pyrimidin-2-amine | 410.3 | 411.2 |
| 202 | tert-butyl 3-((5-(4-hydroxyphenyl)-2-((1s,4s)-4-methylcyclohexylamino)pyrimidin-4-yloxy)methyl)azetidine-1-carboxylate | 468.3 | 469.2 |
| 203 | (R)-tert-butyl 3-((5-(4-hydroxyphenyl)-2-((1s,4S)-4-methylcyclohexylamino)pyrimidin-4-yloxy)methyl)pyrrolidine-1-carboxylate | 482.3 | 483.2 |
| 204 | tert-butyl 4-((5-(4-hydroxyphenyl)-2-((1s,4S)-4-methylcyclohexylamino)pyrimidin-4-yloxy)methyl)piperidine-1-carboxylate | 496.3 | 497.2 |
| 205 | 2-(2-((1s,4S)-4-methylcyclohexylamino)-5-(4-morpholinophenyl)pyrimidin-4-yloxy)-N-(methylsulfonyl)acetamide | 503.2 | 504.2 |
| 206 | methyl 4-(5-(4-(2-methoxyethyl)phenyl)-2-((1s,4s)-4-methylcyclohexylamino)pyrimidin-4-yloxy)piperidine-1-carboxylate | 482.3 | 483.4 |
| 207 | N,N-dimethyl-3-(2-((1s,4s)-4-methylcyclohexylamino)-5-(4-((R)-tetrahydrofuran-3-yloxy)phenyl)pyrimidin-4-yloxy)azetidine-1-sulfonamide | 531.3 | 532.4 |
| 208 | tert-butyl 4-((2-((1s,4s)-4-methylcyclohexylamino)-5-(4-((S)-tetrahydrofuran-3-yloxy)phenyl)pyrimidin-4-yloxy)methyl)piperidine-1-carboxylate | 566.4 | 567.3 |
| 209 | tert-butyl 4-((2-((1s,4s)-4-methylcyclohexylamino)-5-(4-((R)-tetrahydrofuran-3-yloxy)phenyl)pyrimidin-4-yloxy)methyl)piperidine-1-carboxylate | 566.4 | 567.3 |
| 210 | (R)-tert-butyl 3-((2-((1s,4S)-4-methylcyclohexylamino)-5-(4-((S)-tetrahydrofuran-3-yloxy)phenyl)pyrimidin-4-yloxy)methyl)pyrrolidine-1-carboxylate | 552.3 | 553.3 |
| 211 | (R)-tert-butyl 3-((2-((1s,4S)-4-methylcyclohexylamino)-5-(4-((R)-tetrahydrofuran-3-yloxy)phenyl)pyrimidin-4-yloxy)methyl)pyrrolidine-1-carboxylate | 552.3 | 553.3 |
| 212 | (R)-tert-butyl 3-(4-(2-((1s,4S)-4-methylcyclohexylamino)-4-((R)-tetrahydrofuran-3-yloxy)pyrimidin-5-yl)phenoxy)pyrrolidine-1-carboxylate | 538.3 | 539.3 |
| 213 | tert-butyl 3-(2-((1s,4s)-4-methylcyclohexylamino)-5-(4-((R)-tetrahydrofuran-3-yloxy)phenyl)pyrimidin-4-yloxy)azetidine-1-carboxylate | 524.3 | 525.5 |
| 214 | N,N-dimethyl-3-(2-((1s,4s)-4-methylcyclohexylamino)-5-(4-((S)-tetrahydrofuran-3-yloxy)phenyl)pyrimidin-4-yloxy)azetidine-1-sulfonamide | 531.3 | 532.5 |
| 215 | 4-(1-(cyclopropylsulfonyl)azetidin-3-yloxy)-N-((1s,4s)-4-methylcyclohexyl)-5-(4-((S)-tetrahydrofuran-3-yloxy)phenyl)pyrimidin-2-amine | 528.2 | 529.4 |
| 216 | N,N-dimethyl-3-(2-((1s,4s)-4-methylcyclohexylamino)-5-(4-(morpholinosulfonyl)phenyl)pyrimidin-4-yloxy)azetidine-1-sulfonamide | 594.2 | 595.4 |
| 217 | N,N-dimethyl-3-(2-((1s,4s)-4-methylcyclohexylamino)-5-(4-(morpholinosulfonyl)phenyl)pyrimidin-4-yloxy)azetidine-1-sulfonamide | 412.3 | 413.4 |
| 218 | 4-(4-methoxyphenyl)-5-(2-methyl-2H-indazol-6-yl)-N-((1s,4s)-4-methylcyclohexyl)pyrimidin-2-amine | 427.2 | 428.4 |
| 219 | N-((1s,4S)-4-methylcyclohexyl)-4-((R)-pyrrolidin-3-ylmethoxy)-5-(4-((R)-tetrahydrofuran-3-yloxy)phenyl)pyrimidin-2-amine | 452.3 | 453.2 |
| 220 | tert-butyl 3-(2-((1s,4s)-4-methylcyclohexylamino)-5-(4-((S)-tetrahydrofuran-3-yloxy)phenyl)pyrimidin-4-yloxy)azetidine-1-carboxylate | 524.3 | 525.5 |
| 221 | N-((1s,4s)-4-methylcyclohexyl)-4-((1-(methylsulfonyl)azetidin-3-yl)methoxy)-5-(4-((S)-tetrahydrofuran-3-yloxy)phenyl)pyrimidin-2-amine | 516.2 | 517.3 |
| 222 | N,N-dimethyl-4-((2-((1s,4s)-4-methylcyclohexylamino)-5-(4-((S)-tetrahydrofuran-3-yloxy)phenyl)pyrimidin-4-yloxy)methyl)piperidine-1-sulfonamide | 573.3 | 574.5 |
| 223 | 2-methyl-6-(2-((1s,4S)-4-methylcyclohexylamino)-4-((R)-tetrahydrofuran-3-yloxy)ypyrimidin-5-yl)isoindolin-1-one | 422.2 | 423.2 |
| 224 | N,N-dimethyl-3-42-((1s,4s)-4-methylcyclohexylamino)-5-(4-((R)-tetrahydrofuran-3-yloxy)phenyl)pyrimidin-4-yloxy)methyl)azetidine-1-sulfonamide | 545.3 | 546.4 |

TABLE 2-continued

| Example No. | Compound Name | MS Calc: M+ | MS Found M+ +1 |
|---|---|---|---|
| 225 | N-((1s,4s)-4-methylcyclohexyl)-4-((1-(methylsulfonyl)azetidin-3-yl)methoxy)-5-(4-((R)-tetrahydrofuran-3-yloxy)phenyl)pyrimidin-2-amine | 516.2 | 517.3 |
| 226 | N,N-dimethyl-3-((2-((1s,4s)-4-methylcyclohexylamino)-5-(4-((S)-tetrahydrofuran-3-yloxy)phenyl)pyrimidin-4-yloxy)methyl)azetidine-1-sulfonamide | 545.3 | 546.7 |
| 227 | 5-(2-(methoxymethyl)-1-methyl-1H-benzo[d]imidazol-5-yl)-N-((1s,4s)-4-methylcyclohexyl)-4-(oxetan-3-yloxy)pyrimidin-2-amine | 437.2 | 48.4 |
| 228 | N-((1s,4s)-4-methylcyclohexyl)-4-(piperidin-4-ylmethoxy)-5-(4-((R)-tetrahydrofuran-3-yloxy)phenyl)pyrimidin-2-amine | 466.3 | 467.4 |
| 229 | N-((1s,4s)-4-methylcyclohexyl)-4-(1-(methylsulfonyl)azetidin-3-yloxy)-5-(4-(morpholinosulfonyl)phenyl)pyrimidin-2-amine | 565.2 | 566.2 |
| 230 | N-((1s,4S)-4-methylcyclohexyl)-4-(((R)-1-(methylsulfonyl)pyrrolidin-3-yl)methoxy)-5-(4-((R)-tetrahydrofuran-3-yloxy)phenyl)pyrimidin-2-amine | 530.3 | 531.4 |
| 231 | 2-(2-((1s,4s)-4-methylcyclohexylamino)-5-(4-morpholinophenyl)pyrimidin-4-yloxy)propane-1,3-diol | 442.3 | 443.4 |
| 232 | 2-(2-((1s,4s)-4-methylcyclohexylamino)-5-(4-morpholinophenyl)pyrimidin-4-yloxy)acetamide | 425.2 | 426.2 |
| 233 | N-((1s,4s)-4-methylcyclohexyl)-4-(1-(methylsulfonyl)azetidin-3-yloxy)-5-(4-((R)-1-(methylsulfonyl)pyrrolidin-3-yloxy)phenyl)pyrimidin-2-amine | 579.2 | 580.2 |
| 234 | N-((1s,4s)-4-methylcyclohexyl)-4-(1-(methylsulfonyl)azetidin-3-yloxy)-5-(4-((S)-1-(methylsulfonyl)pyrrolidin-3-yloxy)phenyl)pyrimidin-2-amine | 579.2 | 580.2 |
| 235 | tert-butyl 3-((2-((1s,4s)-4-methylcyclohexylamino)-5-(4-((R)-tetrahydrofuran-3-yloxy)phenyl)pyrimidin-4-yloxy)methyl)azetidine-1-carboxylate | 538.3 | 539.5 |
| 236 | N,N-dimethyl-4-((2-((1s,4s)-4-methylcyclohexylamino)-5-(4-((R)-tetrahydrofuran-3-yloxy)phenyl)pyrimidin-4-yloxy)methyl)piperidine-1-sulfonamide | 573.3 | 574.3 |
| 237 | tert-butyl 3-((2-((1s,4s)-4-methylcyclohexylamino)-5-(4-((S)-tetrahydrofuran-3-yloxy)phenyl)pyrimidin-4-yloxy)methyl)azetidine-1-carboxylate | 538.3 | 539.3 |
| 238 | N1,N1-dimethyl-N2-(4-(2-((1s,4S)-4-methylcyclohexylamino)-4-((R)-tetrahydrofuran-3-yloxy)pyrimidin-5-yl)benzyl)ethane-1,2-diamine | 453.3 | 454.5 |
| 239 | (R)-N,N-dimethyl-3-((2-((1s,4S)-4-methylcyclohexylamino)-5-(4-((S)-tetrahydrofuran-3-yloxy)phenyl)pyrimidin-4-yloxy)methyl)pyrrolidine-1-sulfonamide | 559.3 | 560.4 |
| 240 | N,N-dimethyl-2-(2-((1s,4s)-4-methylcyclohexylamino)-5-(4-morpholinophenyl)pyrimidin-4-yloxy)acetamide | 453.3 | 454.5 |
| 241 | N-methyl-2-(2-((1s,4s)-4-methylcyclohexylamino)-5-(4-morpholinophenyl)pyrimidin-4-yloxy)acetamide | 439.3 | 440.4 |
| 242 | N-((1s,4S)-4-methylcyclohexyl)-4-(((R)-1-(methylsulfonyl)pyrrolidin-3-yl)methoxy)-5-(4-((S)-tetrahydrofuran-3-yloxy)phenyl)pyrimidin-2-amine | 530.3 | 531.5 |
| 243 | 4-(azetidin-3-ylmethoxy)-N-((1s,4s)-4-methylcyclohexyl)-5-(4-((S)-tetrahydrofuran-3-yloxy)phenyl)pyrimidin-2-amine | 438.3 | 439.4 |
| 244 | (R)-N,N-dimethyl-3-((2-((1s,4S)-4-methylcyclohexylamino)-5-(4-((R)-tetrahydrofuran-3-yloxy)phenyl)pyrimidin-4-yloxy)methyl)pyrrolidine-1-sulfonamide | 559.3 | 560.4 |
| 245 | N-((1s,4S)-4-methylcyclohexyl)-4-((R)-pyrrolidin-3-ylmethoxy)-5-(4-((S)-tetrahydrofuran-3-yloxy)phenyl)pyrimidin-2-amine | 452.3 | 453.5 |
| 246 | 4-(methoxymethyl)-N-((1s,4s)-4-methylcyclohexyl)-5-(4-morpholinophenyl)-6-(oxetan-3-yloxy)pyrimidin-2-amine | 468.3 | 469.3 |
| 247 | N-((1s,4R)-4-methylcyclohexyl)-5-(4-morpholinophenyl)-4-phenyl-6-((S)-tetrahydrofuran-3-yloxy)pyrimidin-2-amine | 514.3 | 515.3 |
| 248 | N-((1s,4R)-4-methylcyclohexyl)-4-phenyl-6-((S)-tetrahydrofuran-3-yloxy)-5-(4-((S)-tetrahydrofuran-3-yloxy)phenyl)pyrimidin-2-amine | 515.3 | 516.3 |

Example 249

Preparation of 4-(methoxymethyl)-N-((1s,4s)-4-methylcyclohexyl)-5-(4-morpholinophenyl)-6-(oxetan-3-yloxy)pyrimidin-2-amine

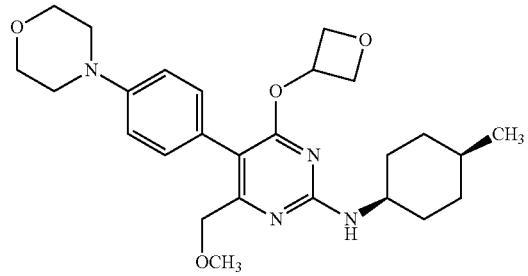

Synthetic Overview:

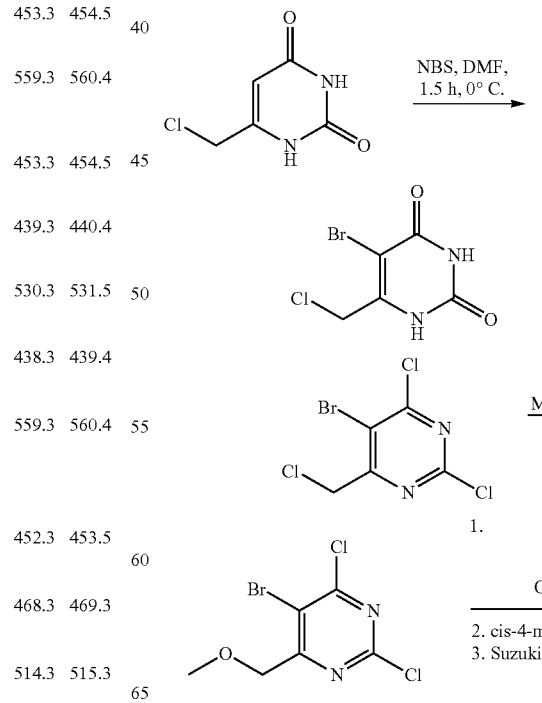

1.
2. cis-4-methylclohexyl amine
3. Suzuki coupling condition

93

-continued

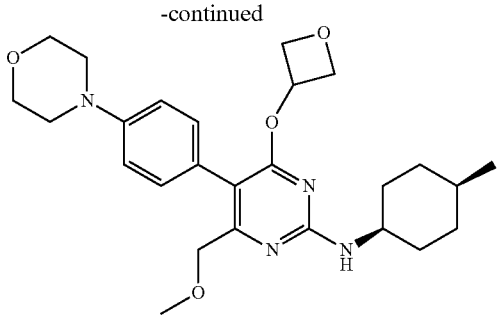

Step 1: Preparation of 5-Bromo-6-(Chloromethyl)uracil (1)

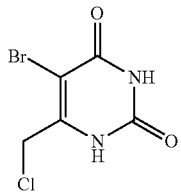

(1)

To a solution of 6-(chloromethyl)uracil (2.0 g, 12.5 mmol) in DMF (15 mL) at 0° C. was added NBS (recrystallized, 2.44 g, 13.7 mmol). The mixture was stirred at 0° C. for 1.5 h, and then quenched by ice water. The precipitate was collected by filtration and washed with AcOH and water to give the title compound (2.35 g, 69%) as a white solid. $^1$H NMR (DMSO, 500 MHz) δ 1.66 (s, 1H), δ 11.61 (s, 1H), δ 4.47 (s, 2H). MS (Multimode, M+H$^+$) $C_5H_5BrClN_2O_2$, calcd. 238.9. found 238.9.

Step 2: Preparation 5-Bromo-2,4-dichloro-6-(Chloromethyl)pyrimidine (2)

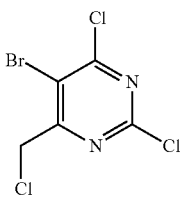

(2)

To a suspension of 5-bromo-6-(chloromethyl)uracil (1) (3.47 g, 14.64 mmol) in POCl$_3$ (30 mL) at room temperature was added one drop of DMF. The mixture was stirred and heated at 110° C. overnight. Then reaction was cooled and concentrated in vacuo, and the residue was purified using ISCO chromatography (80 g silica gel, 0-20% EtOAc in hexanes in 40 min) to give the title compound (3.46 g, 88%)

94 as a white solid. $^1$H NMR (DMSO, 500 MHz) δ 4.88 (s, 2H). MS (ESI, M+H$^+$) $C_5H_3BrCl_3N_2$, calcd. 274.8. found 274.8.

Step 3: Preparation 5-Bromo-2,4-dichloro-6-(methoxymethyl)pyrimidine (3)

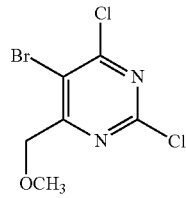

(3)

To a solution of 5-bromo-2,4-dichloro-6-(chloromethyl) pyrimidine (2) (600 mg, 2.19 mmol) in anhydrous MeOH (15 mL) at 0° C. was added NaOMe (25% wt in MeOH, 521 mg, 2.41 mmol). The mixture was stirred at 0° C. for 30 min and then allow warm to room temperature and stirred overnight. After this time the reaction mixture was concentrated in vacuo. The residue was purified using ISCO chromatography (24 g silica gel, 0-1.5% EtOAc in hexanes in 40 min) to give the title compound (480 mg, 81%) as a white solid. $^1$H NMR (DMSO, 300 MHz) δ 4.77 (s, 2H), 4.04 (s, 3H).

Step 4: Preparation of 5-Bromo-2-chloro-4-(methoxymethyl)-6-(oxetan-3-yloxy)pyrimidine (4)

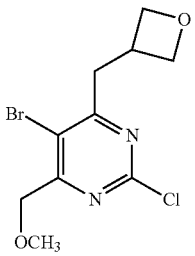

(4)

To a solution of 3-hydroxyoxetane (76 mg, 1.02 mmol) in anhydrous THF (8 mL) at r.t. was added NaH (60% in mineral oil, 39 mg, 0.97 mmol). The mixture was stirred at r.t. for 5 min until there was no hydrogen bubbles generated. 5-bromo-2,4-dichloro-6-(methoxymethyl)pyrimidine (3) (250 mg, 0.93 mmol) was added and the resulting reaction mixture was stirred at r.t. overnight. The reaction was quenched with aqueous NH$_4$Cl and extracted with EtOAc. The organic layer was separated, washed with aqueous NaHCO$_3$, dried (Na$_2$SO$_4$) and concentrated in vacuo. The residue was purified using ISCO chromatography (24 g silica gel, 0-20% EtOAc in hexanes in 40 min) to give the title compound (207 mg, 73%)

as a white solid. $^1$H NMR (DMSO, 500 MHz) δ 5.57-5.52 (m, 1H), 4.91-4.86 (m, 2H), 4.68 (s, 2H), 4.61-4.57 (m, 2H), 3.98 (s, 3H).

Step 5: Preparation of 5-Bromo-4-(methoxymethyl)-N-((1s,4s)-4-methylcyclohexyl)-6-(oxetan-3-yloxy)pyrimidin-2-amine (5)

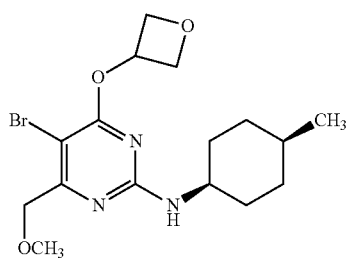

(5)

To a solution of 5-bromo-2-chloro-4-(methoxymethyl)-6-(oxetan-3-yloxy)pyrimidine (4) (195 mg, 0.51 mmol) in EtOH (6 mL) was added cis-4-methylcyclohexylamine hydrochloride (113 mg, 0.76 mmol), followed by triethylamine (0.21 mL). The mixture was refluxed with an oil bath at 80° C. for 8 h. After cooling to room temperature, the reaction mixture was diluted with CH$_2$Cl$_2$ and washed with H$_2$O. The organic layer was separated, dried (Na$_2$SO$_4$) and concentrated in vacuo. The residue was purified by ISCO chromatography (12 g silica gel, 0-25% EtOAc in hexanes in 40 min) to give the title compound (100 mg, 41%) as a colorless gel. $^1$H NMR (CDCl$_3$, 500 MHz) δ 5.61 (m, 1H), 4.98-4.93 (m, 2H), 4.84-4.79 (m, 2H), 4.03 (s, 3H), 3.91 (s, 2H), 2.73-2.64 (m 1H), 1.71-1.51 (m, 9H), 0.94 (d, 3H). MS (Multimode, M+H$^+$) C$_{16}$H$_{24}$N$_3$O$_3$, calcd. 386.3. found 386.1.

Step 6: Preparation of 4-(methoxymethyl)-N-((1s,4s)-4-methylcyclohexyl)-5-(4-morpholinophenyl)-6-(oxetan-3-yloxy)pyrimidin-2-amine

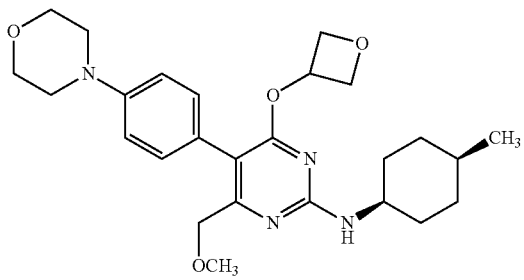

To a mixture of 5-bromo-4-(methoxymethyl)-N-((1s,4s)-4-methylcyclohexyl)-6-(oxetan-3-yloxy)pyrimidin-2-amine (5) (60.0 mg, 0.16 mmol), 4-morpholinophenyl boronic acid (143.0 mg, 0.31 mmol), Pd(dppf)$_2$Cl$_2$ (13.0 mg, 0.016 mmol) and Cs$_2$CO$_3$ (156 mg, 0.48 mmol) was added 1,4-dioxane (1 mL), DMF (1 mL) and H$_2$O (1 mL). The mixture was purged with argon, and heated with an oil bath at 100° C. for 5 minutes. After cooling to room temperature, the reaction mixture was diluted with EtOAc, and filtered. The organic layer was separated, washed with brine and 5% aqueous LiCl, dried (Na$_2$SO$_4$) and concentrated in vacuo. The residue was purified by ISCO chromatography (24 g silica gel, 0-2.5% MeOH/CH$_2$Cl$_2$ in 40 min) to give the title compound (18.0 mg, 25%) as a white foam. $^1$H NMR (DMSO, 500 MHz) 7.10 (d, 2H), 6.97 (d, 2H), 5.58 (bd, 1H), 4.91 (t, 2H), 4.63 (t, 2H), 3.81 (s, 3H), 3.75 (t, 4H), 3.44 (s, 2H), 3.15 (t, 4H), 1.79-1.69 (m, 1H), 1.44-1.14 (m, 10H), 0.83 (d, 3H); MS (Multimode, M+H$^+$) C$_{26}$H$_{37}$N$_4$O$_4$, calcd. 469.3. found 469.3.

Example 250

Preparation of 4-(methoxymethyl)-N-((1s,4s)-4-methylcyclohexyl)-6-(oxetan-3-yloxy)-5-(4-((S)-tetrahydrofuran-3-yloxy)phenyl)pyrimidin-2-amine

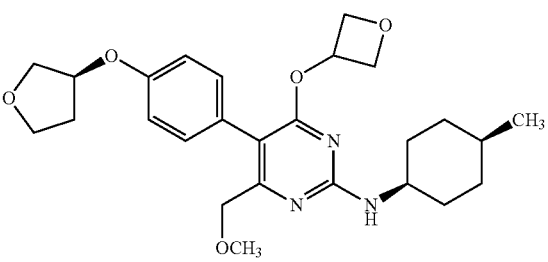

Step 1: Preparation 5-Bromo-2,4-dichloro-6-(methoxymethyl)pyrimidine (1)

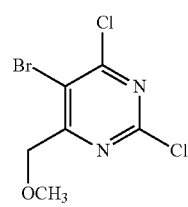

(1)

To a solution of 5-bromo-2,4-dichloro-6-(chloromethyl)pyrimidine (600 mg, 2.19 mmol) in anhydrous MeOH (15 mL) at 0° C. was added NaOMe (25% wt in MeOH, 521 mg, 2.41 mmol). The mixture was stirred at 0° C. for 30 min and then allow warm to room temperature and stirred overnight. After this time the reaction mixture was concentrated in vacuo. The residue was purified using ISCO chromatography (24 g silica gel, 0-1.5% EtOAc in hexanes in 40 min) to give the title compound (480 mg, 81%) as a white solid. $^1$H NMR (DMSO, 300 MHz) δ 4.77 (s, 2H), 4.04 (s, 3H).

Step 2: Preparation of 5-Bromo-2-chloro-4-(methoxymethyl)-6-(oxetan-3-yloxy)pyrimidine (2)

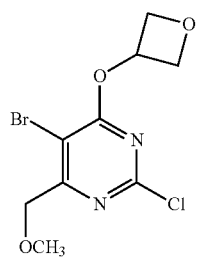

(2)

To a solution of 3-hydroxyoxetane (76 mg, 1.02 mmol) in anhydrous THF (8 mL) at r.t. was added NaH (60% in mineral oil, 39 mg, 0.97 mmol). The mixture was stirred at r.t. for 5 min until there was no hydrogen bubbles generated. 5-bromo-2,4-dichloro-6-(methoxymethyl)pyrimidine (1) (250 mg, 0.93 mmol) was added and the resulting reaction mixture was stirred at r.t. overnight. The reaction was quenched with aqueous NH$_4$Cl and extracted with EtOAc. The organic layer was separated, washed with aqueous NaHCO$_3$, and dried (Na$_2$SO$_4$) and concentrated in vacuo. The residue was purified using ISCO chromatography (24 g silica gel, 0-20% EtOAc in hexanes in 40 min) to give the title compound (207 mg, 73%) as a white solid. $^1$H NMR (DMSO, 500 MHz) δ 5.57-5.52 (m, 1H), 4.91-4.86 (m, 2H), 4.68 (s, 2H), 4.61-4.57 (m, 2H), 3.98 (s, 3H).

Step 3: Preparation of 5-Bromo-4-(methoxymethyl)-N-((1s,4s)-4-methylcyclohexyl)-6-(oxetan-3-yloxy)pyrimidin-2-amine (3)

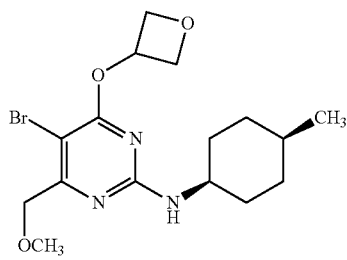

(3)

To a solution of 5-bromo-2-chloro-4-(methoxymethyl)-6-(oxetan-3-yloxy)pyrimidine (2) (195 mg, 0.51 mmol) in EtOH (6 mL) was added cis-4-methylcyclohexylamine hydrochloride (113 mg, 0.76 mmol), followed by triethylamine (0.21 mL). The mixture was refluxed with an oil bath at 80° C. for 8 h. After cooling to room temperature, the reaction mixture was diluted with CH$_2$Cl$_2$, and washed with H$_2$O. The organic layer was separated, dried (Na$_2$SO$_4$) and concentrated in vacuo. The residue was purified by ISCO chromatography (12 g silica gel, 0-25% EtOAc/hexanes in 40 min) to give the title compound (3) (100 mg, 41%) as a colorless gel. $^1$H NMR (CDCl$_3$, 500 MHz) δ 5.61 (m, 1H), 4.98-4.93 (m, 2H), 4.84-4.79 (m, 2H), 4.03 (s, 3H), 3.91 (s, 2H), 2.73-2.64 (m, 1H), 1.71-1.51 (m, 9H), 0.94 (d, 3H). MS (Multimode, M+H$^+$) C$_{16}$H$_{25}$N$_3$O$_3$, calcd. 386.1. found 386.1.

Step 4: Preparation of 4-(4-(methoxymethyl)-2-((1s,4s)-4-methylcyclohexylamino)-6-(oxetan-3-yloxy)pyrimidin-5-yl)phenol (4)

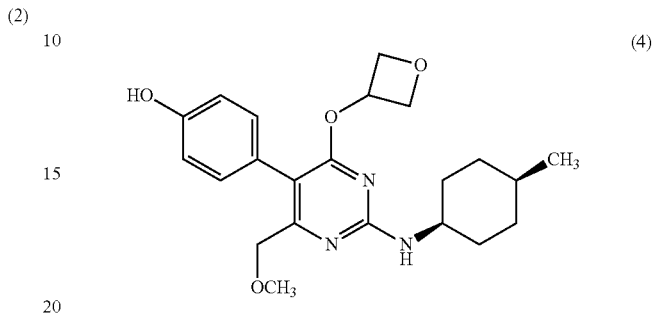

(4)

To a mixture of 5-bromo-4-(methoxymethyl)-N-((1s,4s)-4-methylcyclohexyl)-6-(oxetan-3-yloxy)pyrimidin-2-amine (3) (100.0 mg, 0.26 mmol), 4-hydroxyphenyl boronic acid (43.0 mg, 0.31 mmol), Pd(dppf)$_2$Cl$_2$ (21.0 mg, 0.026 mmol) and Cs$_2$CO$_3$ (254 mg, 0.78 mmol) was added 1,4-dioxane (1 mL), DMF (1 mL) and H$_2$O (1 mL). The mixture was purged with argon, and heated with an oil bath at 100° C. for 10 min. After cooling to room temperature, the reaction mixture was diluted with EtOAc, and filtered. The organic layer was separated, washed with brine and 5% aqueous LiCl, dried (Na$_2$SO$_4$) and concentrated in vacuo. The residue was purified by ISCO chromatography (12 g silica gel, 0-4% MeOH in CH$_2$Cl$_2$ in 40 min) to give the title compound (26.0 mg, 25%) as a white foam. $^1$H NMR (DMSO, 500 MHz) δ 9.52 (s, 1H), 7.04 (d, 2H), 6.79 (d, 2H), 5.58 (bd, 1H), 4.90 (t, 2H), 4.63 (t, 2H), 3.81 (s, 3H), 3.41 (s, 2H), 1.75-1.67 (m, 1H), 1.44-1.13 (m, 10H), 0.83 (d, 3H).

Step 5: Preparation of 4-(methoxymethyl)-N-((1s,4s)-4-methylcyclohexyl)-6-(oxetan-3-yloxy)-5-(4-((S)-tetrahydrofuran-3-yloxy)phenyl)pyrimidin-2-amine

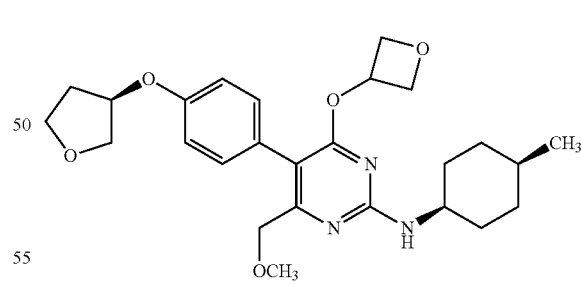

To a solution of 4-(4-(methoxymethyl)-2-((1s,4s)-4-methylcyclohexylamino)-6-(oxetan-3-yloxy)pyrimidin-5-yl)phenol (4) (26.0 mg, 0.065 mmol) in anhydrous DMF (1 mL) at r.t. was added Cs$_2$CO$_3$ (63.0 mg, 0.20 mmol). The mixture was stirred at r.t. for 10 min followed by (R)-tetrahydrofuran-3-yl 4-methylbenzenesulfonate (27.0 mg, 0.11 mmol). The reaction mixture was stirred at r.t. overnight, and then heated with an oil bath at 40° C. for 6 h. After this time the reaction was quenched with H$_2$O and extracted with EtOAc. The organic layer was separated, dried (Na$_2$SO$_4$) and concentrated in vacuo. The residue was purified using ISCO chromatography (12 g silica gel, 0-4% MeOH in CH$_2$Cl$_2$ in 40 min) to give the title compound (16 mg, 52%) as a colorless gel. $^1$H NMR (DMSO, 500 MHz) δ 7.17 (d, 2H), 6.95 (d, 2H), 5.59 (bd, 1H), 5.07-5.03 (m, 1H), 4.91 (t, 2H), 4.63 (t, 2H), 3.93-3.89 (m, 1H), 3.88-3.74 (m, 6H), 3.41 (s, 2H), 2.28-2.20 (m, 1H), 2.02-1.95 (m, 1H), 1.77-1.66 (m, 1H), 1.45-1.11 (m, 10H), 0.82 (d, 3H); MS (Multimode, M+H$^+$) C$_{26}$H$_{36}$N$_3$O$_5$, calcd. 470.3. found 470.2.

Example 251

Preparation of 4-methyl-N-((1s,4s)-4-methylcyclohexyl)-6-(oxetan-3-yloxy)-5-(4-((S)-tetrahydrofuran-3-yloxy)phenyl)pyrimidin-2-amine

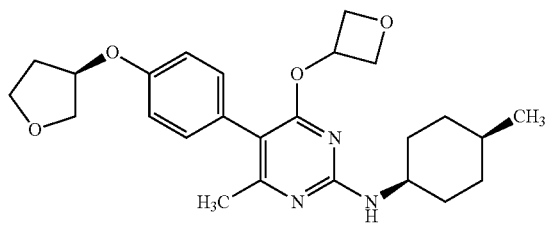

Step 1: Preparation of 5-bromo-2-chloro-4-methyl-6-(oxetan-3-yloxy)pyrimidine (1)

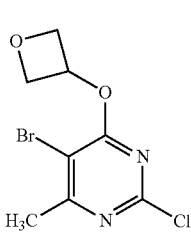

(1)

To a solution of oxetan-3-ol (0.368 g, 4.96 mmol) in anhydrous THF (16 mL) at 0° C. was added NaH (60% in mineral oil, 213 mg, 5.32 mmol). The mixture was stirred at 0° C. for 20 min, then 5-bromo-2,4-dichloro-6-methylpyrimidine (0.800 g, 3.30 mmol) was added to the mixture at 0° C. and stirred for 5 min. After this time the reaction was quenched with saturated aqueous NH$_4$Cl and extracted with EtOAc. The organic layer was separated, dried (Na$_2$SO$_4$) and concentrated in vacuo. The residue was purified using ISCO chromatography (24 g silica gel, 1-25% EtOAc in hexanes in 40 min) to give the title compound (0.566 g, 61%) as a white oil. $^1$H NMR (CDCl$_3$, 500 MHz) δ 5.71-5.66 (m, 1H), 5.030-4.99 (m, 2H), 4.79-4.76 (m, 2H), 2.59 (s, 3H).

Step 2: Preparation of 5-bromo-4-methyl-N-((1s,4s)-4-methylcyclohexyl)-6-(oxetan-3-yloxy)pyrimidin-2-amine (2)

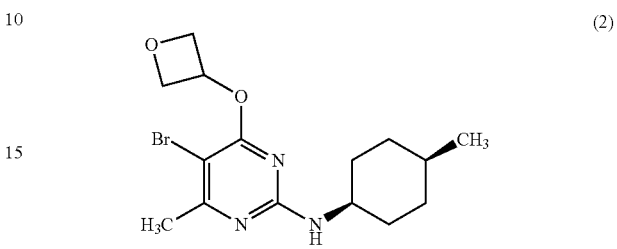

(2)

To a solution of 5-bromo-2-chloro-4-methyl-6-(oxetan-3-yloxy)pyrimidine (1) (554 mg, 1.97 mmol) in n-BuOH (16 mL) was added cis-4-methylcyclohexylamine hydrochloride (412 mg, 2.75 mmol), followed by triethylamine (0.78 mL). The mixture was heated with an oil bath at 115° C. for 4 h. After this time, additional cis-4-methylcyclohexylamine hydrochloride (250 mg, 1.67 mmol) and triethylamine (0.40 mL) was added. The reaction was stirred at 115° C. for another 1 h and then cooled and concentrated in vacuo. The residue was partitioned between water and EtOAc. The organic layer was separated, dried (Na$_2$SO$_4$) and concentrated in vacuo. The residue was purified by ISCO chromatography (24 g silica gel, 0-10% EtOAc in hexanes in 40 min) to give the title compound (2) (381 mg, 52%) as a yellow solid. $^1$H NMR (CDCl$_3$, 500 MHz) δ 5.58-5.52 (m, 1H), 4.94-4.91 (m, 2H), 54.81-4.78 (m, 2H), 3.87 (bs, 1H), 2.40 (s, 3H), 1.76-1.69 (m, 2H), 1.63-1.52 (m, 6H), 1.23-1.15 (m, 1H), 0.92 (d, 3H).

Step 3: 4-(4-methyl-2-((1s,4s)-4-methylcyclohexylamino)-6-(oxetan-3-yloxy)pyrimidin-5-yl)phenol (3)

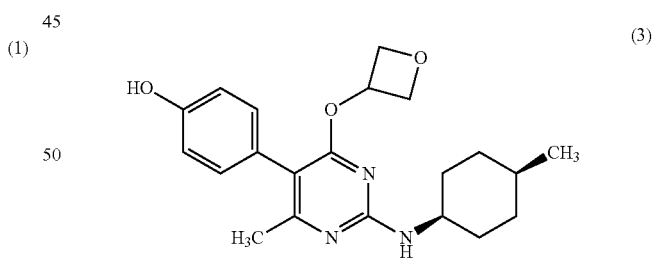

(3)

To a solution of 5-bromo-4-methyl-N-((1s,4s)-4-methylcyclohexyl)-6-(oxetan-3-yloxy)pyrimidin-2-amine (2) (180 mg, 0.50 mmol) in DMF/dioxane/water (1 mL/1 mL/1 mL) was added 4-hydroxyphenylboronic acid (84 mg, 0.60 mmol) followed by Pd(dppf)$_2$Cl$_2$ (41 mg, 0.05 mmol) and Cs$_2$CO$_3$ (489 mg, 1.5 mmol). The mixture was heated with an oil bath at 100° C. for 20 minutes. After this time the reaction was cooled and concentrated in vacuo, then purified by ISCO chromatography (12 g silica gel, 0-25% EtOAc in hexanes in 40 min) to give the title compound (130 mg, 70%) as a yellow solid. $^1$H NMR (CH$_3$OD, 300 MHz) δ 7.06-7.01 (m, 2H), 6.83-6.78 (m, 2H), 5.54-5.48 (m, 1H), 4.91-4.86 (m, 2H), 4.59-4.54 (m, 2H), 3.96-3.90 (m, 1H), 2.09 (s, 3H), 1.82-1.54 (m, 7H), 1.38-1.20 (m, 2H), 0.96 (d, 3H).

Step 4: 4-methyl-N-((1s,4s)-4-methylcyclohexyl)-6-(oxetan-3-yloxy)-5-(4-((S)-tetrahydrofuran-3-yloxy)phenyl)pyrimidin-2-amine

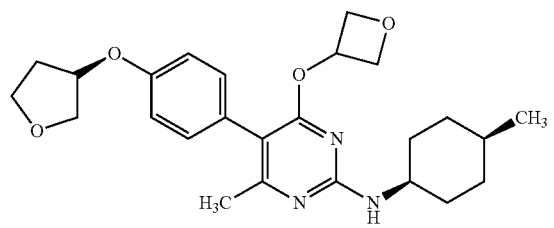

To a solution of 4-(4-methyl-2-((1s,4s)-4-methylcyclohexylamino)-6-(oxetan-3-yloxy)pyrimidin-5-yl)phenol (3) (130 mg, 0.35 mmol) in anhydrous DMF (4 mL) at r.t. was added Cs$_2$CO$_3$ (344 mg, 1.06 mmol), KI (12 mg, 0.07 mmol) and (R)-tetrahydrofuran-3-yl 4-methylbenzenesulfonate (256 mg, 1.06 mmol). The mixture was stirred at r.t. for 4 h, and then was heated at 90° C. for another 0.5 h. After this time the mixture was cooled and extracted with EtOAc. The organic layer was separated, and dried (Na$_2$SO$_4$) and concentrated in vacuo. The residue was purified using ISCO chromatography (12 g silica gel, 0-25% EtOAc in hexanes in 40 min) to give the title compound (46 mg, 30%) as a white solid. $^1$H NMR (CDCl$_3$, 500 MHz) δ 7.16-7.14 (m, 2H), 6.90-6.85 (m, 2H), 5.95-5.51 (m, 1H), 4.97-4.95 (m, 1H), 4.90-4.84 (m, 2H), 4.62-4.66 (m, 2H), 4.05-3.90 (m, 5H), 2.24-2.18 (m, 2H), 2.15 (s, 3H), 1.79-1.75 (m, 2H), 1.51-1.65 (m, 6H), 1.27-1.21 (m, 2H), 0.93 (d, 3H). MS (ESI, M+H$^+$) C$_{25}$H$_{34}$N$_3$O$_4$, calcd. 440.2. found 440.2

Example 252

Preparation of methyl 2-((1s,4R)-4-methylcyclohexylamino)-5-(4-morpholinophenyl)-6-((S)-tetrahydrofuran-3-yloxy)pyrimidine-4-carboxylate and 2-((1s,4R)-4-methylcyclohexylamino)-5-(4-morpholinophenyl)-6-((S)-tetrahydrofuran-3-yloxy)pyrimidine-4-carboxylic acid

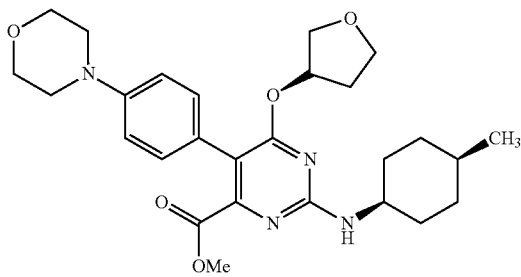

Step 1: Preparation of (R)-methyl 2-chloro-5-iodo-6-(tetrahydrofuran-3-yloxy)pyrimidine-4-carboxylate (1)

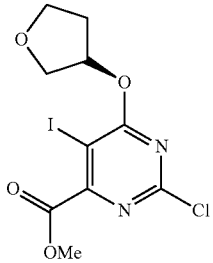

To a solution of (R)-(−)-3-hydroxy-tetrahydrofuran (0.214 g, 2.42 mmol) in anhydrous THF (10 mL) at 0° C. was added NaH (60% in mineral oil, 103 mg, 2.58 mmol). The mixture was stirred at 0° C. for 30 min, then methyl 2,6-dichloro-5-iodopyrimidine-4-carboxylate (0.539 g, 1.62 mmol) was added to the mixture at −10° C. The reaction mixture was stirred at the same temperature for 30 min, and then allow warm to r.t. for 4 h. The reaction was then diluted with EtOAc and acidified with 2 N HCl. The aqueous layer was extracted with EtOAc. The organic layer was dried (Na$_2$SO$_4$) and concentrated in vacuo. The residue was dissolved in ether (8 mL) and MeOH (2 mL), and then trimethylsilyldiazomethane (2 M, 2 mL, 4 mmol) was added at 0° C. The reaction was stirred at r.t. for 1 h, and then quenched by 2 N HCl and concentrated in vacuo. The residue was purified by ISCO chromatography (24 g silica gel, 1-10% EtOAc in hexanes in 40 min) to give the title compound (0.140 g, 26%) as a colorless oil. $^1$H NMR (CDCl$_3$, 500 MHz) δ 5.69-5.66 (m, 1H), 4.10 (dd, 1H), 4.05-3.92 (m, 6H), 2.38-2.30 (m, 1H), 2.24-2.18 (m, 1H).

Step 2: Preparation of methyl 5-iodo-2-((1s,4S)-4-methylcyclohexylamino)-6-((R)-tetrahydrofuran-3-yloxy)pyrimidine-4-carboxylate (2)

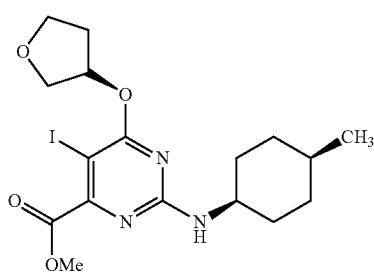

To a solution of (R)-methyl 2-chloro-5-iodo-6-(tetrahydrofuran-3-yloxy)pyrimidine-4-carboxylate (1) (140 mg, 0.36 mmol) in n-BuOH (6 mL) was added cis-4-methylcyclohexylamine hydrochloride (85 mg, 0.55 mmol), followed by triethylamine (0.15 mL, 1.08 mmol). The mixture was heated with an oil bath at 130° C. for 2 h. After this time the mixture was cooled and concentrated in vacuo. The residue was purified by ISCO chromatography (12 g silica gel, 0-25% EtOAc in hexanes in 40 min) to give the title compound (2) (111 mg, 66%) as a yellow oil. $^1$H NMR (CDCl$_3$, 300 MHz) δ 5.53-

5.47 (m, 1H), 4.11-3.88 (m, 8H), 2.20-2.18 (m, 2H), 1.85-1.71 (m, 2H), 1.67-1.47 (m, 5H), 1.23-1.05 (m, 2H), 0.92 (d, 3H).

Step 3: Preparation of methyl 2-((1s,4R)-4-methyl-cyclohexylamino)-5-(4-morpholinophenyl)-6-((S)-tetrahydrofuran-3-yloxy)pyrimidine-4-carboxylate

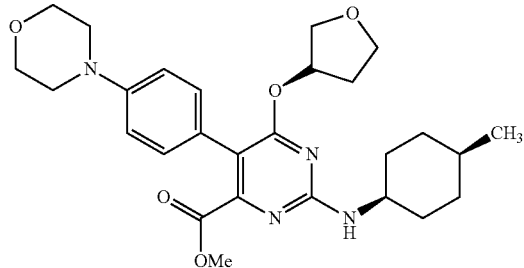

To a solution of methyl 5-iodo-2-((1s,4S)-4-methylcyclohexylamino)-6-((R)-tetrahydrofuran-3-yloxy)pyrimidine-4-carboxylate (2) (129 mg, 0.28 mmol) in DMF/dioxane/water (1 mL/1 mL/1 mL) was added 4-morpholinophenylboronic acid (70 mg, 0.33 mmol) followed by $Pd(dppf)_2Cl_2$ (23 mg, 0.028 mmol) and $Cs_2CO_3$ (274 mg, 0.84 mmol). The mixture was heated with an oil bath at 100° C. for 10 min. The reaction the was cooled and concentrated in vacuo, and then purified by ISCO chromatography (12 g silica gel, 0-50% EtOAc in hexanes in 40 min) to give the title compound (61 mg, 44%) as a white solid. $^1$H NMR ($CD_3OD$, 300 MHz) δ 7.12 (d, 2H), 6.94 (d, 2H), 5.60-5.56 (m, 1H), 4.01-3.96 (m, 2H), 3.84-3.79 (m, 7H), 3.60 (s, 3H), 3.16 (t, 4H), 2.26-2.06 (m, 1H), 2.06-2.00 (m, 1H), 1.85-1.77 (m, 2H), 1.72-1.56 (m, 5H), 1.39-1.28 (m, 2H), 0.97 (d, 3H). MS (ESI, M+H$^+$) $C_{27}H_{37}N_4O_5$, calcd. 497.3 found 497.2.

Step 4: Preparation of 2-((1s,4R)-4-methylcyclohexylamino)-5-(4-morpholinophenyl)-6-((S)-tetrahydrofuran-3-yloxy)pyrimidine-4-carboxylic acid

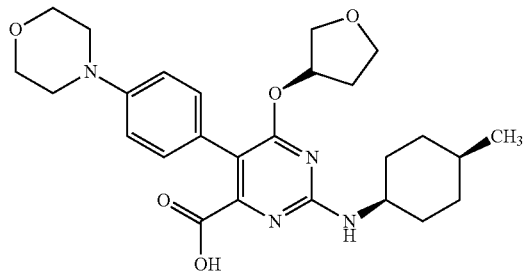

To a solution of methyl 2-((1s,4R)-4-methylcyclohexylamino)-5-(4-morpholinophenyl)-6-((S)-tetrahydrofuran-3-yloxy)pyrimidine-4-carboxylate (37 mg, 0.074 mmol) in anhydrous THF (3 mL) and water (3 mL) was added LiOH aqueous solution (1 M, 1.5 mL) at r.t. The mixture was stirred for overnight. After this time the reaction was heated at 50° C. and stirred for another 16 h. The mixture was diluted with EtOAc and the aqueous layer was acidified by 2 N HCl. The aqueous layer was extracted with EtOAc. The organic layers were separated, and dried ($Na_2SO_4$) and concentrated in vacuo. The residue was purified by trituration using MeOH and dichloromethane to give the title compound (14 mg, 39%) as a off-white solid. $^1$H NMR ($CD_3OD$, 500 MHz) δ 7.26 (d, 2H), 7.17 (d, 2H), 5.71-5.67 (m, 1H), 4.28 (bs, 1H), 3.96 (d, 1H), 3.90 (t, 4H), 3.85 (dd, 1H), 3.82-3.73 (m, 2H), 3.36-3.32 (m, 4H), 2.32-2.24 (m, 1H), 2.06-2.01 (m, 1H), 1.95-1.86 (m, 2H), 1.81-1.73 (m, 2H), 1.75-1.65 (m, 2H), 1.59 (bs, 1H), 1.32-1.22 (m, 2H), 1.00 (d, 3H). MS (ESI, M+H$^+$) $C_{26}H_{35}N_4O_5$, calcd. 483.3. found 483.1.

Example 253

Dual Corrector Potentiator Assay

The ability of exemplary compounds to correct the processing defect of ΔF508 CTFR, i.e. increase the surface expression of CFTR channels, and potentiate existing channels was demonstrated in an FRT cell electrophysiological (Ussing chamber) assay. For use in the corrector assay, FRT epithelial cell monolayers are grown on Snapwell filter inserts and optionally treated with a compound of invention, vehicle (DMSO) or reference corrector N-(2-(5-chloro-2-methoxyphenylamino)-4'-methyl-4,5'-bithiazol-2'-yl)pivalamide (C17). Cells are exposed to compound, vehicle (negative control) or reference corrector (positive control) in a cell/tissue incubator at 37° C. for 24 hours prior to the assay. The inserts are then transferred to a Physiologic Instruments Ussing chamber (P2302) and superfused with 5 ml of a HEPES buffered physiological saline (HB-PS) as the serosal solution with composition (in mM): NaCl, 137; KCl, 4.0; $CaCl_2$, 1.8; $MgCl_2$, 1; HEPES, 10; Glucose, 10; pH adjusted to 7.4 with NaOH. The mucosal solution will be 5 ml of 10CF—PS with composition (in mM): Na-gluconate, 137; KCl, 4; $CaCl_2$, 1.8; $MgCl_2$, 1; HEPES, 10; Glucose, 10; pH adjusted to 7.4 with N-methyl-D-glucamine to create a transepithelial Cl ion gradient. Transepithelial voltage is clamped to 0 mV and the short circuit current (ISC)—reflecting the net ion (Cl—) transport across the epithelial cell monolayer—is measured using a Physiologic Instruments VCC MC8 epithelial voltage clamp (Physiologic Instruments, Inc., San Diego, Calif.). The assay is carried out at 27° C.

After acquisition of at least 10 minutes of baseline current, agonists (final concentrations: 10 μM forskolin, 100 μM 3-isobutyl-1-methylxanthine [IBMX] and 20 μM genistein) and antagonist (final concentration: 20 μM CFTRinh-172) will be applied sequentially and cumulatively at ~10-15 minute intervals to both serosal and mucosal epithelial surfaces. On occasion where a 10-15 min interval is not sufficient for ISC to reach a new steady-state after compound addition, the interval between compound additions may have been extended.

Agonists are added as 200×-1000× stock solutions to both the serosal and mucosal sides. Transepithelial resistance is monitored every 20 s. In a potentiator assay, appropriate volumes from 10 mM compound stock solution in DMSO are added to the mucosal side (i.e. the 10CF—PS solution containing half chamber) of vehicle treated inserts. Compound is added acutely after activation of CFTR by Forskolin and prior to additions of IBMX, genistein, and CFTRinh-172.

Corrector efficacy—as given in Table 3—is measured as the total change in ISC (i.e. the difference in ISC before and after addition of all agonists) obtained from cells treated with 3 μM compound of invention and normalized to the total change in ISC obtained from the same batch of cells treated contemporaneously with 10 μM reference corrector C17. Potentiator efficacy—as given in Table 3—is measured as the change in ISC after acute addition of 1 μM compound to the mucosal side of vehicle treated cells divided by the total change in ISC after sequential additions of 1 µM compound, 100 µM IBMX, and 20 µM genistein.

Table 3 provides results for exemplary compounds. Corrector efficacy ranges correspond to: +=<0.3, ++=0.3-0.6, and +++=>0.6. Potentiator efficacy ranges correspond to +=<0.1, ++=0.1-0.25, and +++=>0.25.

TABLE 3

| Example No. | Compound Name | Corrector Efficacy | Potentiator Efficacy |
|---|---|---|---|
| 1 | N,N-dimethyl-3-(2-((1s,4s)-4-methylcyclohexylamino)-5-(4-morpholinophenyl)-pyrimidin-4-yloxy)azetidine-1-sulfonamide | +++ | ++ |
| 6 | 4-((R)-tetrahydrofuran-3-yloxy)-5-(4-((S)-tetrahydrofuran-3-yloxy)phenyl)-N-(cis-4-methylcyclohexyl)pyrimidin-2-amine hydrochloride salt | ++ | ++ |
| 43 | 4-methyl-N-((1s,4S)-4-methylcyclohexyl)-5-(4-morpholinophenyl)-6-((R)-tetrahydrofuran-3-yloxy)pyrimidin-2-amine | ++ | + |
| 59 | N-((1s,4s)-4-methylcyclohexyl)-4-(1-(methylsulfonyl)azetidin-3-yloxy)-5-(4-morpholinophenyl)pyrimidin-2-amine | ++ | + |
| 78 | N-((1s,4S)-4-methylcyclohexyl)-4-((R)-1-(methylsulfonyl)pyrrolidin-3-yl)methoxy)-5-(4-morpholinophenyl)pyrimidin-2-amine | ++ | + |
| 80 | N-((1s,4s)-4-methylcyclohexyl)-4-((1-(methylsulfonyl)azetidin-3-yl)methoxy)-5-(4-morpholinophenyl)pyrimidin-2-amine | ++ | +++ |
| 93 | N-((1s,4s)-4-methylcyclohexyl)-4-(tetrahydro-2H-pyran-4-yloxy)-5-(4-((R)-tetrahydrofuran-3-yloxy)phenyl)pyrimidin-2-amine | +++ | ++ |
| 103 | methyl 3-(4-(2-((1s,4S)-4-methylcyclohexylamino)-4-((R)-tetrahydrofuran-3-yloxy)pyrimidin-5-yl)phenoxy)pyrrolidine-1-carboxylate | ++ | + |
| 112 | N,N-dimethyl-3-(4-(2-((1s,4S)-4-methylcyclohexylamino)-4-((R)-tetrahydrofuran-3-yloxy)pyrimidin-5-yl)phenoxy)pyrrolidine-1-carboxamide | ++ | + |
| 152 | N-((1s,4s)-4-methylcyclohexyl)-4-(1-(methylsulfonyl)piperidin-4-yloxy)-5-(4-((S)-tetrahydrofuran-3-yloxy)phenyl)pyrimidin-2-amine | +++ | +++ |
| 153 | 5-(4-(2-methoxyethoxy)phenyl)-N-((1s,4s)-4-methylcyclohexyl)-4-(1-(methylsulfonyl)azetidin-3-yloxy)pyrimidin-2-amine | ++ | + |
| 170 | N-(2,6-dimethylcyclohexyl)-4-((R)-tetrahydrofuran-3-yloxy)-5-(4-((S)-tetrahydrofuran-3-yloxy)phenyl)pyrimidin-2-amine | +++ | + |
| 206 | methyl 4-(5-(4-(2-methoxyethyl)phenyl)-2-((1s,4s)-4-methylcyclohexylamino)pyrimidin-4-yloxy)piperidine-1-carboxylate | ++ | + |
| 207 | N,N-dimethyl-3-(2-((1s,4s)-4-methylcyclohexylamino)-5-(4-((R)-tetrahydrofuran-3-yloxy)phenyl)pyrimidin-4-yloxy)azetidine-1-sulfonamide | +++ | + |
| 214 | N,N-dimethyl-3-(2-((1s,4s)-4-methylcyclohexylamino)-5-(4-((S)-tetrahydrofuran-3-yloxy)phenyl)pyrimidin-4-yloxy)azetidine-1-sulfonamide | +++ | + |
| 215 | 4-(1-(cyclopropylsulfonyl)azetidin-3-yloxy)-N-((1s,4s)-4-methylcyclohexyl)-5-(4-((S)-tetrahydrofuran-3-yloxy)phenyl)pyrimidin-2-amine | +++ | +++ |

REFERENCES

All publications and patents mentioned herein, including those items listed below, are hereby incorporated by reference in their entirety as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

I claim:
1. A compound represented by Formula I:

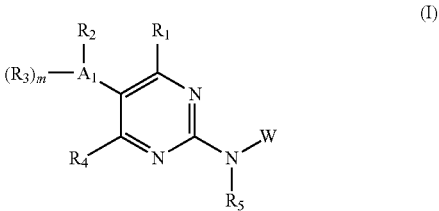

or a pharmaceutically acceptable salt or N-oxide thereof, wherein:

$R_1$ is —O—$(CR_6R_7)_n$-$A_2$, —N($R_6$)$(CR_6R_7)_n$-$A_2$, —S—$(CR_6R_7)_n$-$A_2$, or heterocycloalkyl, wherein said heterocycloalkyl is optionally substituted with one or more substituents independently selected from the group consisting of halogen, $C_1$-$C_6$alkyl, $C_3$-$C_6$cycloalkyl, $C_2$-$C_4$alkenyl, $C_2$-$C_4$alkynyl, $C_1$-$C_6$alkoxyl, hydroxyl, —$CF_3$, —$CH_2F$, —$CHF_2$, —N($R_8$)$R_9$, —CN, —C(O)$R_{10}$, —$CO_2R_8$, —OC(O)$R_9$, —CON($R_8$)$R_9$, —N($R_8$)COR$_{10}$, —N($R_8$)$SO_2R_{10}$, —$SO_2N(R_8)R_9$, —N($R_8$)$SO_2N(R_8)R_9$, and —$SO_2R_{10}$;

$R_2$ is —O-heterocycloalkyl, —O-heterocycloalkenyl, —Y-heterocycloalkyl, —Y-heterocycloalkenyl, heterocycloalkyl, -heterocycloalkenyl, -cycloalkyl, -cycloalkenyl, —$(CR_6R_7)_n$—$C_1$-$C_6$alkoxyl, —O—$(CR_6R_7)_n$—$C_1$-$C_6$alkoxyl, $C_1$-$C_6$alkoxyl, halogen, —$CF_3$, —$CH_2F$, —$CHF_2$, —$OCF_3$, —$OCH_2F$, hydroxyl, or $C_1$-$C_6$alkyl, wherein said heterocycloalkyl, heterocycloalkenyl, cycloalkyl, and cycloalkenyl are optionally substituted with one or more substituents independently selected from the group consisting of halogen, $C_1$-$C_6$alkyl, $C_3$-$C_6$cycloalkyl, $C_2$-$C_4$alkenyl, $C_2$-$C_4$alkynyl, $C_1$-$C_6$alkoxyl, hydroxyl, —$CF_3$, —$CH_2F$, —$CHF_2$, —$OCF_3$, —N($R_8$)$R_9$, —CN, —C(O)$R_{10}$, —$CO_2R_8$, —OC(O)$R_9$, —CON($R_8$)$R_9$, —N($R_8$)COR$_{10}$, —N($R_8$)$SO_2R_{10}$, —$SO_2N(R_8)R_9$, —N($R_8$)$SO_2N(R_8)R_9$, and —$SO_2R_{10}$;

$R_3$ is hydrogen, halogen, $C_1$-$C_6$alkyl, $C_3$-$C_6$cycloalkyl, $C_2$-$C_4$alkenyl, $C_2$-$C_4$alkynyl, $C_1$-$C_6$alkoxyl, hydroxyl, —$CF_3$, —$CH_2F$, —$CHF_2$, —$OCF_3$, —$OCH_2F$, —N($R_8$)

R$_9$, —CN, —C(O)R$_{10}$, —CO$_2$R$_8$, —CON(R$_8$)R$_9$, —N(R$_8$)COR$_{10}$, —N(R$_8$)SO$_2$R$_{10}$, —SO$_2$N(R$_8$)R$_9$, or —SO$_2$R$_{10}$;

R$_4$ is hydrogen, halogen, C$_1$-C$_4$alkyl, cyclopropyl, —CN, or —CF$_3$;

R$_5$ is hydrogen or C$_1$-C$_4$alkyl;

R$_6$ and R$_7$ each represent independently for each occurrence hydrogen or alkyl, or when R$_6$ and R$_7$ are attached to the same atom, R$_6$ and R$_7$ are optionally taken together with the atom to which they are attached to form a 3-6 membered cycloalkyl or heterocycloalkyl group;

R$_8$ and R$_9$ each represent independently for each occurrence hydrogen, alkyl, cycloalkyl, heterocycloalkyl, aryl, heteroaryl, aralkyl, or heteroaralkyl; or when R$_8$ and R$_9$ are attached to the same atom, R$_8$ and R$_9$ are optionally taken together with the atom to which they are attached to form a 3-6 membered cycloalkyl or heterocycloalkyl group;

R$_{10}$ represents independently for each occurrence alkyl, cycloalkyl, heterocycloalkyl, aryl, heteroaryl, aralkyl, or heteroaralkyl;

A$_1$ is phenylene or a monocyclic heteroarylene group;

A$_2$ is a heterocycloalkyl group containing at least one nitrogen or sulfur atom, and wherein said heterocycloalkyl group is optionally substituted with one or more substituents independently selected from the group consisting of halogen, C$_1$-C$_6$alkyl, C$_2$-C$_4$alkenyl, C$_2$-C$_4$alkynyl, C$_1$-C$_6$alkoxyl, C$_3$-C$_6$cycloalkyl, hydroxyl, —CF$_3$, —CH$_2$F, —CHF$_2$, —N(R$_8$)R$_9$, —CN, —C(O)R$_{10}$, —CO$_2$R$_8$, —OC(O)R$_9$, —CON(R$_8$)R$_9$, —N(R$_8$)COR$_{10}$, —N(R$_8$)SO$_2$R$_{10}$, —SO$_2$N(R$_8$)R$_9$, —N(R$_8$)SO$_2$N(R$_8$)R$_9$, and —SO$_2$R$_{10}$;

W is C$_1$-C$_6$alkyl or C$_4$-C$_{10}$cycloalkyl, each of which are optionally substituted with one, two, or three substituents independently selected from the group consisting of C$_1$-C$_6$alkyl, C$_1$-C$_6$haloalkyl, cycloalkyl, —OC$_1$-C$_6$alkyl, —O-cycloalkyl, —OH, —CF$_3$, and fluoro;

Y is —N(R$_8$)—, —S—, —S(O)—, or —S(O)$_2$—;

m is 1 or 2; and n is 0, 1, 2, 3, or 4.

2. The compound of claim 1, wherein R$_1$ is —O—(CR$_6$R$_7$)$_n$-A$_2$ or a heterocycloalkyl group optionally substituted with one or more substituents independently selected from the group consisting of halogen, C$_1$-C$_6$alkyl, C$_3$-C$_6$cycloalkyl, —C(O)R$_{10}$, —CO$_2$R$_8$, —OC(O)R$_9$, —CON(R$_8$)R$_9$, —N(R$_8$)COR$_{10}$, —N(R$_8$)SO$_2$R$_{10}$, —SO$_2$N(R$_8$)R$_9$, —N(R$_8$)SO$_2$N(R$_8$)R$_9$, and —SO$_2$R$_{10}$.

3. The compound of claim 1, wherein R$_1$ is —O—(CR$_6$R$_7$)$_n$-A$_2$.

4. The compound of claim 3, wherein A$_2$ is a heterocycloalkyl group containing at least one nitrogen or sulfur atom, and wherein said heterocycloalkyl group is optionally substituted with one or more substituents independently selected from the group consisting of halogen, C$_1$-C$_6$alkyl, C$_3$-C$_6$cycloalkyl, —C(O)R$_{10}$, —CO$_2$R$_8$, —OC(O)R$_9$, —CON(R$_8$)R$_9$, —N(R$_8$)COR$_{10}$, —N(R$_8$)SO$_2$R$_{10}$, —SO$_2$N(R$_8$)R$_9$, —N(R$_8$)SO$_2$N(R$_8$)R$_9$, and —SO$_2$R$_{10}$.

5. The compound of claim 3, wherein A$_2$ is a heterocycloalkyl group containing at least one nitrogen or sulfur atom, and wherein said heterocycloalkyl group is substituted with one or more substituents independently selected from the group consisting of —CO$_2$R$_8$, —CON(R$_8$)R$_9$, —SO$_2$N(R$_8$)R$_9$, and —SO$_2$R$_{10}$.

6. The compound of claim 3, wherein A$_2$ is azetidinyl, pyrrolidinyl, or piperidinyl, each substituted with —CON(R$_8$)R$_9$, —CO$_2$R$_8$, —SO$_2$N(R$_8$)R$_9$, or —SO$_2$R$_{10}$.

7. The compound of claim 3, wherein A$_2$ is one of the following:

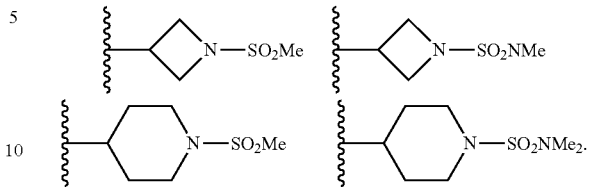

8. The compound of claim 1, wherein R$_2$ is —O-heterocycloalkyl or —O—(CR$_6$R$_7$)$_n$—C$_1$-C$_6$alkoxyl; wherein said heterocycloalkyl is optionally substituted with one or more substituents independently selected from the group consisting of halogen, C$_1$-C$_6$alkyl, —CO$_2$R$_8$, —CON(R$_8$)R$_9$, —SO$_2$N(R$_8$)R$_9$, and —SO$_2$R$_{10}$.

9. The compound of claim 1, wherein R$_2$ is —O-heterocycloalkyl; wherein said heterocycloalkyl is optionally substituted with one or more substituents independently selected from the group consisting of —CO$_2$R$_8$, —CON(R$_8$)R$_9$, —SO$_2$N(R$_8$)R$_9$, and —SO$_2$R$_{10}$.

10. The compound of claim 1, wherein R$_2$ is morpholinyl, —O-tetrahydrofuranyl, O-tetrahydropyranyl, —O-pyrrolidinyl, O-azetidinyl or —O-piperidinyl; wherein said pyrrolidinyl, azetidinyl or piperidinyl each independently is optionally substituted with one or more substituents independently selected from the group consisting of —CO$_2$R$_8$, —CON(R$_8$)R$_9$, —SO$_2$N(R$_8$)R$_9$, and —SO$_2$R$_{10}$.

11. The compound of claim 1, wherein R$_2$ is —O-tetrahydrofuranyl.

12. The compound of claim 1, wherein R$_3$ is hydrogen, halogen, —OCF$_3$, —OCH$_2$F, —CF$_3$, C$_1$-C$_6$alkyl, or C$_1$-C$_6$alkoxyl.

13. The compound of claim 1, wherein R$_8$ and R$_9$ each represent independently for each occurrence hydrogen, methyl, ethyl or cyclopropyl.

14. The compound of claim 1, wherein R$_{10}$ is methyl, ethyl, n-propyl, isopropyl, butyl, cyclopropyl, cyclobutyl, phenyl, or benzyl.

15. The compound of claim 1, wherein A$_1$ is phenylene.

16. The compound of claim 1, wherein W is C$_5$-C$_{10}$cycloalkyl optionally substituted with one or two substituents independently selected from the group consisting of C$_1$-C$_6$alkyl, —CF$_3$, and fluoro.

17. The compound of claim 1, wherein W is cyclohexyl substituted with one or two substituents independently selected from the group consisting of C$_1$-C$_6$alkyl, —CF$_3$, and fluoro.

18. The compound of claim 1, wherein the compound is selected from the group consisting of: N,N-dimethyl-3-(2-((1s,4S)-4-methylcyclohexylamino)-5-(4-morpholinophenyl)pyrimidin-4-yloxy)azetidine-1-sulfonamide; N-(cis-4-methylcyclohexyl)-4-(1-(methylsulfonyl)azetidin-3-yloxy)-5-(4-((R)-tetrahydrofuran-3-yloxy)phenyl)pyrimidin-2-amine; N-(cis-4-methylcyclohexyl)-4-(1-(methylsulfonyl)azetidin-3-yloxy)-5-(4-((S)-tetrahydrofuran-3-yloxy)phenyl)pyrimidin-2-amine; methyl 4-(2-((1s,4s)-4-methylcyclohexylamino)-5-(4-morpholinophenyl)pyrimidin-4-yloxy)piperidine-1-carboxylate; N-((1s,4s)-4-methylcyclohexyl)-4-(1-(methylsulfonyl)piperidin-4-yloxy)-5-(4-((S)-tetrahydrofuran-3-yloxy)phenyl)pyrimidin-2-amine; N,N-dimethyl-3-(2-((1s,4s)-4-methylcyclohexylamino)-5-(4-((R)-tetrahydrofuran-3-yloxy)phenyl)pyrimidin-4-yloxy)azetidine-1-sulfonamide;

N,N-dimethyl-3-(2-((1s,4s)-4-methylcyclohexylamino)-5-(4-((S)-tetrahydrofuran-3-yloxy)phenyl)pyrimidin-4-yloxy)azetidine-1-sulfonamide; and 4-(1-(cyclopropylsulfonyl)azetidin-3-yloxy)-N-((1s,4s)-4-methylcyclohexyl)-5-(4-((S)-tetrahydrofuran-3-yloxy)phenyl)pyrimidin-2-amine; or a pharmaceutically acceptable salt or N-oxide thereof.

19. A pharmaceutical composition comprising a compound of claim 1 and a pharmaceutically acceptable carrier.

20. A method of treating cystic fibrosis, comprising administering to a subject in need thereof a therapeutically effective amount of a compound of claim 1.

\* \* \* \* \*